(12) United States Patent
Zhang et al.

(10) Patent No.: US 11,124,523 B2
(45) Date of Patent: Sep. 21, 2021

(54) 2,6-DIOXASPIRO [4,5] DECANE DERIVATIVES AND PREPARATION METHOD THEREFOR AND PHARMACEUTICAL APPLICATIONS THEREOF

(71) Applicant: SHANDONG LUYE PHARMACEUTICAL CO., LTD., Shandong (CN)

(72) Inventors: Yang Zhang, Shanghai (CN); Wentao Wu, Shanghai (CN); Guangwen Yang, Shanghai (CN); Zhixiang Li, Shanghai (CN); Jikui Sun, Shanghai (CN); Jie Li, Shanghai (CN); Jian Li, Shanghai (CN); Shuhui Chen, Shanghai (CN)

(73) Assignee: SHANDONG LUYE PHARMACEUTICAL CO., LTD.

( * ) Notice: Subject to any disclaimer, the term of this patent is extended or adjusted under 35 U.S.C. 154(b) by 0 days.

(21) Appl. No.: 16/755,551

(22) PCT Filed: Oct. 12, 2018

(86) PCT No.: PCT/CN2018/110021
§ 371 (c)(1),
(2) Date: Apr. 10, 2020

(87) PCT Pub. No.: WO2019/072235
PCT Pub. Date: Apr. 18, 2019

(65) Prior Publication Data
US 2020/0255444 A1 Aug. 13, 2020

(30) Foreign Application Priority Data

Oct. 13, 2017 (CN) .......................... 201710954727.7
Dec. 19, 2017 (CN) .......................... 201711377788.8
Apr. 26, 2018 (CN) .......................... 201810387066.9
Aug. 9, 2018 (CN) .......................... 201810904945.4

(51) Int. Cl.
*C07D 493/10* (2006.01)
*A61P 23/00* (2006.01)

(52) U.S. Cl.
CPC ............ *C07D 493/10* (2013.01); *A61P 23/00* (2018.01)

(58) Field of Classification Search
CPC ............................... C07D 493/10; A61P 23/00
See application file for complete search history.

(56) References Cited

U.S. PATENT DOCUMENTS

2017/0326124 A1* 11/2017 Yamashita .............. A61P 29/00
2018/0362482 A1   12/2018 Han et al.

FOREIGN PATENT DOCUMENTS

WO    2012/129495 A1    9/2012
WO    2017/063509 A1    4/2017

OTHER PUBLICATIONS

English Translation of International Search Report and Written Opinion, dated Jan. 14, 2019, for International Application No. PCT/CN2018/110021, 6 pages.

* cited by examiner

*Primary Examiner* — Timothy R Rozof
(74) *Attorney, Agent, or Firm* — Seed IP Law Group LLP

(57) ABSTRACT

The present invention relates to a series of 2,6-dioxaspiro [4,5] decane derivatives and applications thereof in preparation of opiate receptor μ agonist related drugs; and in particular relates to the derivative compounds shown in formula (I), tautomers thereof or pharmaceutically acceptable compositions thereof.

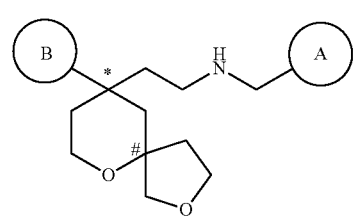

(I)

18 Claims, 1 Drawing Sheet

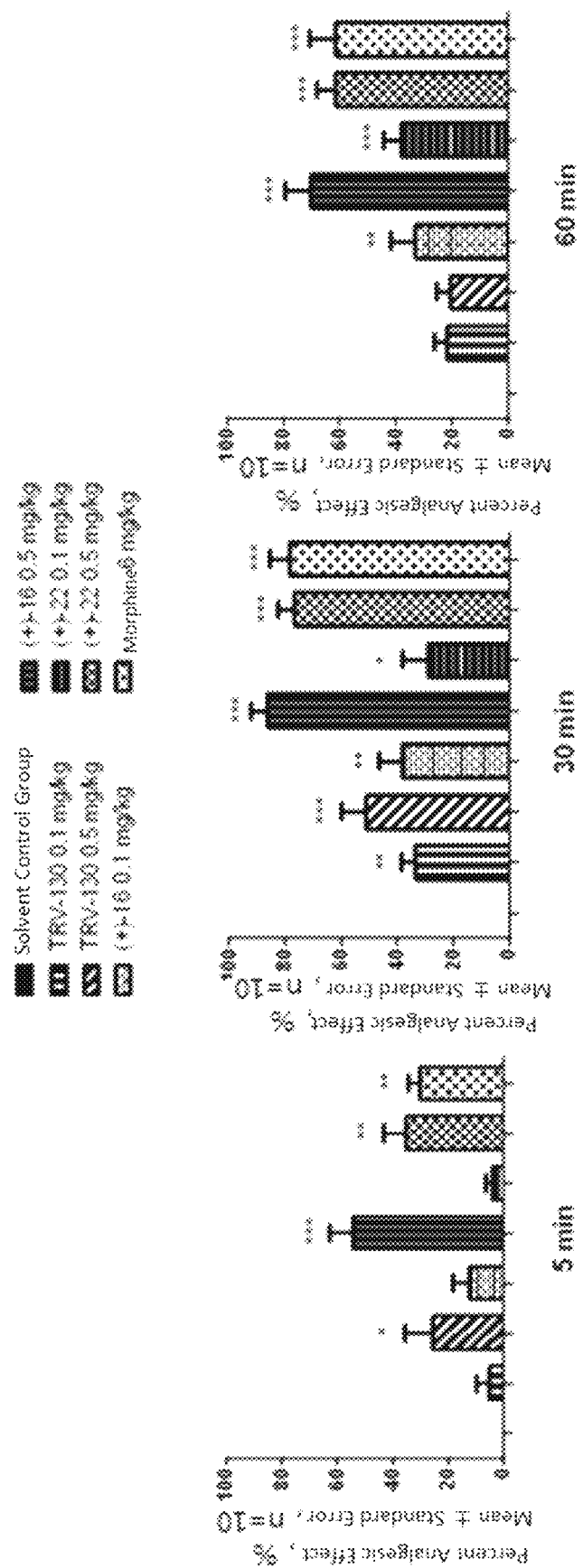

2,6-DIOXASPIRO [4,5] DECANE DERIVATIVES AND PREPARATION METHOD THEREFOR AND PHARMACEUTICAL APPLICATIONS THEREOF

CROSS-REFERENCE TO RELATED APPLICATIONS

This application claims priority to Chinese Patent Application Nos:
CN201710954727.7, filed on Oct. 13, 2017;
CN201711377788.8, filed on Dec. 19, 2017;
CN201810387066.9, filed on Apr. 26, 2018; and
CN201810904945.4, filed on Aug. 9, 2018.

TECHNICAL FIELD

The present disclosure relates to a series of 2,6-dioxaspiro [4,5] decane compounds, and use thereof in the preparation of medicaments for treating diseases associated with agonists for μ-receptor which is an opioid receptor. Specifically, the present disclosure relates to derivative compounds represented by formula (I), tautomers thereof, or pharmaceutically acceptable compositions thereof.

BACKGROUND ART

The 2,6-dioxaspiro [4,5] decane compounds of the present disclosure are agonists for μ receptor which is a Gi protein-"biased" opioid receptor, and have been used in numerous therapeutic applications, especially for treating pain and pain-related disorders.

Opioid receptors are a class of G protein-coupled receptors with opioid peptides acting as ligands, and μ, κ, and δ receptors are the classic three types of opioid receptors. Opioid receptors are widely distributed in the body, but unevenly distributed in the nervous system. Opioid receptors are distributed at higher density in the brain, medial thalamus, ventricles, and periaqueductal gray, and these structures are related to the integration and perception of pain.

Opioids are currently the most effective analgesics in clinical practice, but they are often likely to cause some target-related side effects, such as respiratory depression, constipation, etc. The binding of opioid GPCR receptors to ligands can simultaneously affect multiple downstream signaling pathways, including Gi protein signaling pathway and β-Arrestin signaling pathway. Current researches show that the analgesic effect of opioids is derived from the Gi protein signaling pathway of μ receptors, and the related side effects, such as respiratory depression, constipation, etc., are associated with the β-Arrestin signaling pathway downstream of μ receptors. An enhanced analgesic effect, a prolonged duration of efficacy, and reduced related adverse reactions are observed in β-Arrestin-2-knockout mice injected with morphine, compared with wild-type mice. Therefore, the Gi protein-biased μ-receptor agonists can selectively activate the Gi signaling pathway and have no or little effect on the β-Arrestin pathway. Hence, the Gi protein-biased μ-receptor agonists can be expected to have a better analgesic effect in clinical use and show a great reduction in opioid-related adverse reactions.

For Gi protein-biased μ-receptor agonist TRV-130 (Oliceridine) developed by Travena, Inc., Phase 3 clinical trials have been completed currently. In the published Phase 2 clinical trial data, TRV-130 has exhibited a good analgesic effect and shown a significant reduction in side effects compared to morphine. The structures of TRV-130 (comparative compound 1) and comparative compound 2 are disclosed in Patent Publication No. WO2012129495A1.

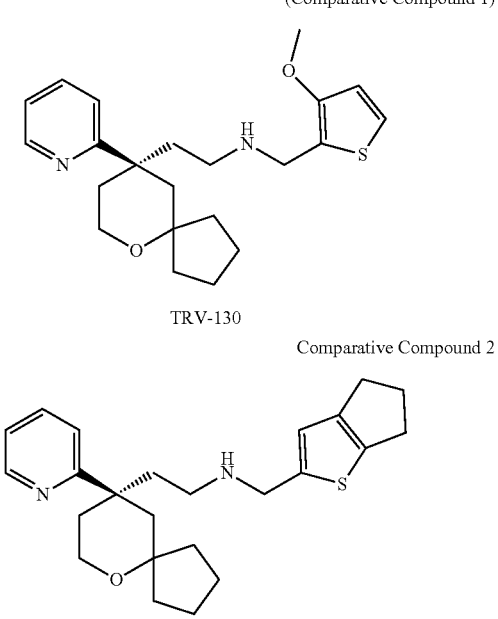

TRV-130

SUMMARY

The present disclosure provides a compound represented by formula (I), an isomer thereof, or a pharmaceutically acceptable salt thereof,

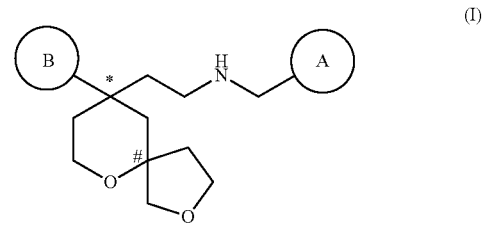

wherein
ring A is selected from a 6-10 membered aryl group and a 5-10 membered heterocyclic group, wherein the 6-10 membered aryl group or 5-10 membered heterocyclic group is optionally substituted with 1, 2, or 3 R;
ring B is selected from phenyl and pyridyl, wherein the phenyl or pyridyl is optionally substituted with 1, 2, or 3 R,
wherein R is each independently selected from H, F, Cl, Br, I, OH, $NH_2$, $C_{1-3}$ alkyl, and $C_{1-3}$ alkoxy, wherein the $C_{1-3}$ alkyl or $C_{1-3}$ alkoxy is optionally substituted with 1, 2, or 3 R',
R' is selected from: F, Cl, Br, I, OH, and $NH_2$;
a carbon atom with "*" is a chiral carbon atom, which exists in the form of a single (R) or (S) enantiomer or in the form enriched in one enantiomer;
a carbon atom with "#" is a chiral carbon atom, which exists in the form of a single (R) or (S) enantiomer or in the form enriched in one enantiomer; and the 5-10 membered heterocyclic group contains 1, 2, 3, or 4 heteroatoms or heteroatomic groups independently selected from —NH—, —O—, —S—, and N.

In some solutions of the present disclosure, the R is each independently selected from H, F, Cl, Br, I, OH, NH$_2$, Me, Et, and

wherein the Me, Et, or

is optionally substituted with 1, 2, or 3 R', and other variables are as defined in the present disclosure.

In some solutions of the present disclosure, the R is each independently selected from H, F, Cl, Br, I, OH, NH$_2$, CN, Me, CH$_2$F, CHF$_2$, CF$_3$, Et, and

and other variables are as defined in the present disclosure.

In some solutions of the present disclosure, the ring A is selected from phenyl, thienyl, 5,6-dihydro-4H-cyclopenta[c]thienyl, 1,3-dihydrothieno[3,4-c]furanyl, 4,5,6,7-tetrahydrobenzo[c]thiophene, and 1,2,3,4-tetrahydronaphthyl, wherein the phenyl, thienyl, 5,6-dihydro-4H-cyclopenta[c]thienyl, 1,3-dihydrothieno[3,4-c]furanyl, 4,5,6,7-tetrahydrobenzo[c]thiophene, and 1,2,3,4-tetrahydronaphthyl are optionally substituted with 1, 2, or 3 R, and other variables are as defined in the present disclosure.

In some solutions of the present disclosure, the ring A is selected from

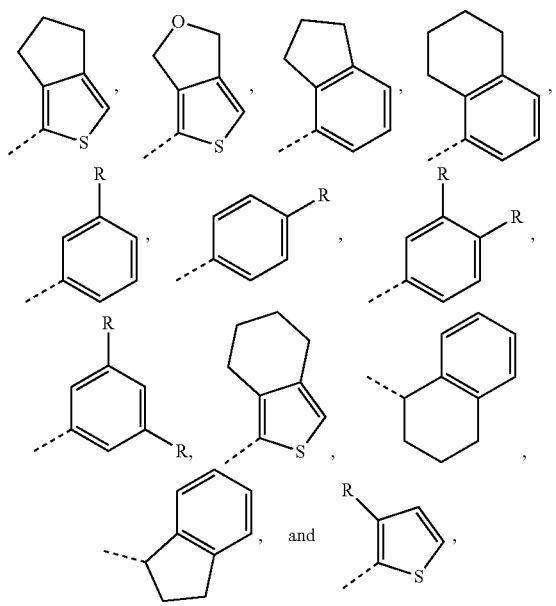

and other variables are as defined in the present disclosure.

In some solutions of the present disclosure, the ring A is selected from

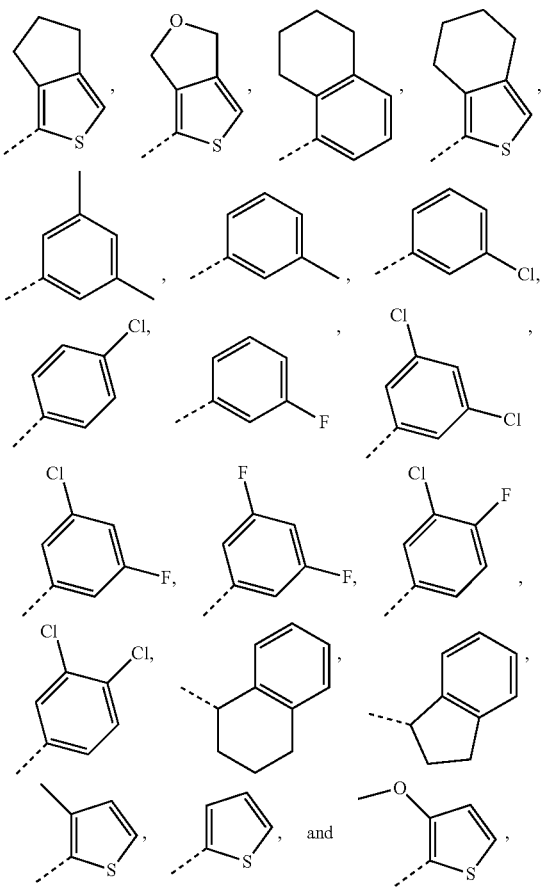

and other variables are as defined in the present disclosure.

In some solutions of the present disclosure, the ring B is selected from

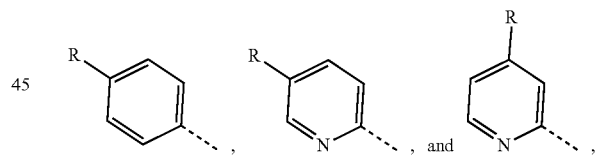

and other variables are as defined in the present disclosure.

In some solutions of the present disclosure, the ring B is selected from

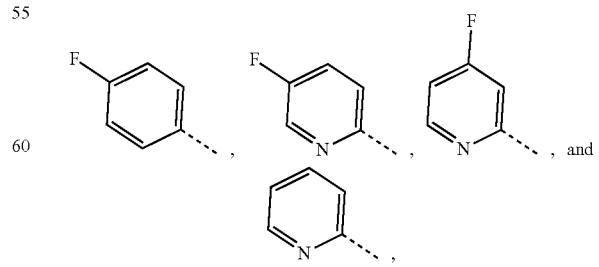

and other variables are as defined in the present disclosure.

The present disclosure provides a compound represented by formula (I), an isomer thereof, or a pharmaceutically acceptable salt thereof,

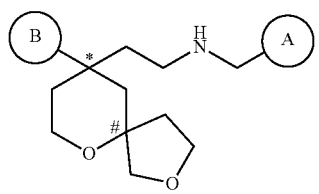

(I)

wherein ring A is selected from phenyl and a 5-10 membered heterocyclic group, wherein the phenyl or 5-10 membered heterocyclic group is optionally substituted with 1, 2, or 3 R;

ring B is selected from phenyl and pyridyl, wherein the phenyl or pyridyl is optionally substituted with 1, 2, or 3 R, wherein R is each independently selected from H, F, Cl, Br, I, OH, $NH_2$, $C_{1-3}$ alkyl, and $C_{1-3}$ alkoxy, wherein the $C_{1-3}$ alkyl or $C_{1-3}$ alkoxy is optionally substituted with 1, 2, or 3 R';

R' is selected from: F, Cl, Br, I, OH, and $NH_2$;

a carbon atom with "*" is a chiral carbon atom, which exists in the form of a single (R) or (S) enantiomer or in the form enriched in one enantiomer;

a carbon atom with "#" is a chiral carbon atom, which exists in the form of a single (R) or (S) enantiomer or in the form enriched in one enantiomer; and the 5-10 membered heterocyclic group contains 1, 2, 3, or 4 heteroatoms or heteroatomic groups independently selected from —NH—, —O—, —S—, and N.

In some solutions of the present disclosure, the R is each independently selected from H, F, Cl, Br, I, OH, $NH_2$, Me, Et, and

wherein the Me, Et, or

is optionally substituted with 1, 2, or 3 R', and other variables are as defined in the present disclosure.

In some solutions of the present disclosure, the R is each independently selected from H, F, Cl, Br, I, OH, $NH_2$, CN, Me, $CH_2F$, $CHF_2$, $CF_3$, Et, and

and other variables are as defined in the present disclosure.

In some solutions of the present disclosure, the ring A is selected from phenyl, thienyl, 5,6-dihydro-4H-cyclopenta[c]thienyl, 1,3-dihydrothieno[3,4-c]furanyl, and 1,2,3,4-tetrahydronaphthyl, wherein the phenyl, thienyl, 5,6-dihydro-4H-cyclopenta[c]thienyl, 1,3-dihydrothieno[3,4-c]furanyl, and 1,2,3,4-tetrahydronaphthyl are optionally substituted with 1, 2, or 3 R, and other variables are as defined in the present disclosure.

In some solutions of the present disclosure, the ring A is selected from

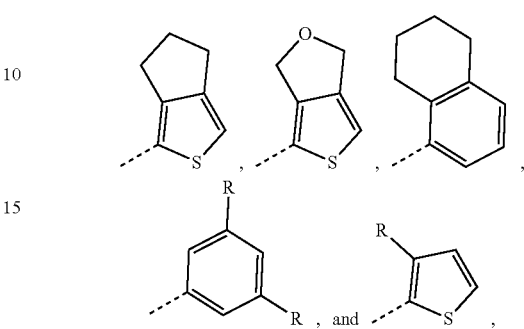

and other variables are as defined in the present disclosure.

In some solutions of the present disclosure, the ring A is selected from

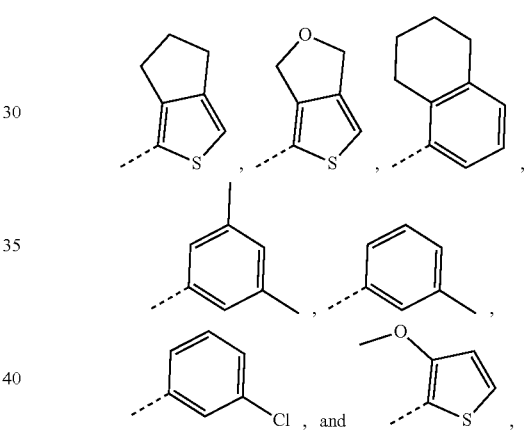

and other variables are as defined in the present disclosure.

In some solutions of the present disclosure, the ring B is selected from

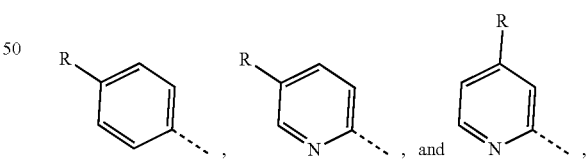

and other variables are as defined in the present disclosure.

In some solutions of the present disclosure, the ring B is selected from

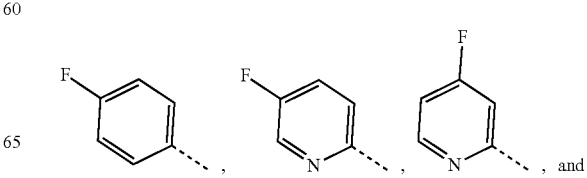

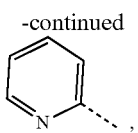

and other variables are as defined in the present disclosure.

The present disclosure provides a compound represented by formula (I), an isomer thereof, or a pharmaceutically acceptable salt thereof,

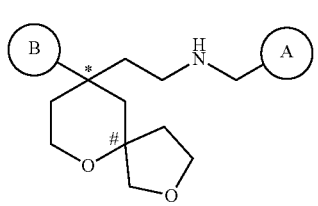

(I)

wherein ring A is selected from phenyl and a 5-10 membered heterocyclic group, wherein the phenyl or 5-10 membered heterocyclic group is optionally substituted with 1, 2, or 3 R;

ring B is selected from phenyl and pyridyl, wherein the phenyl or pyridyl is optionally substituted with 1, 2, or 3 R, wherein R is each independently selected from H, F, Cl, Br, I, OH, $NH_2$, $C_{1-3}$ alkyl, and $C_{1-3}$ alkoxy, wherein the $C_{1-3}$ alkyl or $C_{1-3}$ alkoxy is optionally substituted with 1, 2, or 3 R';

R' is selected from: F, Cl, Br, I, OH, and $NH_2$;

a carbon atom with "*" is a chiral carbon atom, which exists in the form of a single (R) or (S) enantiomer or in the form enriched in one enantiomer;

a carbon atom with "#" is a chiral carbon atom, which exists in the form of a single (R) or (S) enantiomer or in the form enriched in one enantiomer; and the 5-10 membered heterocyclic group contains 1, 2, 3, or 4 heteroatoms or heteroatomic groups independently selected from —NH—, —O—, —S—, and N.

In some solutions of the present disclosure, the R is each independently selected from H, F, Cl, Br, I, OH, $NH_2$, Me, Et, and

wherein the Me, Et, or

is optionally substituted with 1, 2, or 3 R', and other variables are as defined in the present disclosure.

In some solutions of the present disclosure, the R is each independently selected from H, F, Cl, Br, I, OH, $NH_2$, CN, Me, $CH_2F$, $CHF_2$, $CF_3$, Et, and

and other variables are as defined in the present disclosure.

In some solutions of the present disclosure, the ring A is selected from phenyl, thienyl, 5,6-dihydro-4H-cyclopenta[c]thienyl, 1,3-dihydrothieno[3,4-c]furanyl, 4,5,6,7-tetrahydrobenzo[c]thiophene, and 1,2,3,4-tetrahydronaphthyl, wherein the phenyl, thienyl, 5,6-dihydro-4H-cyclopenta[c]thienyl, 1,3-dihydrothieno[3,4-c]furanyl, 4,5,6,7-tetrahydrobenzo[c]thiophene, and 1,2,3,4-tetrahydronaphthyl are optionally substituted with 1, 2, or 3 R, and other variables are as defined in the present disclosure.

In some solutions of the present disclosure, the ring A is selected from

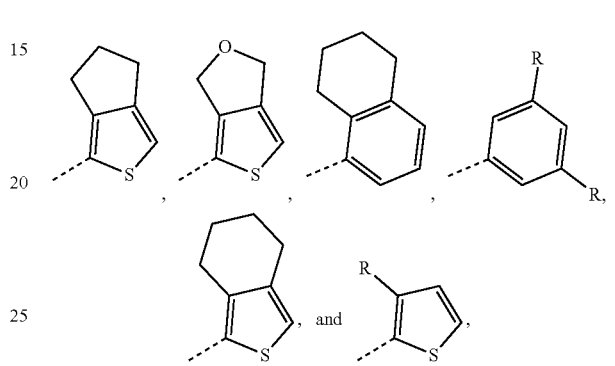

and other variables are as defined in the present disclosure.

In some solutions of the present disclosure, the ring A is selected from

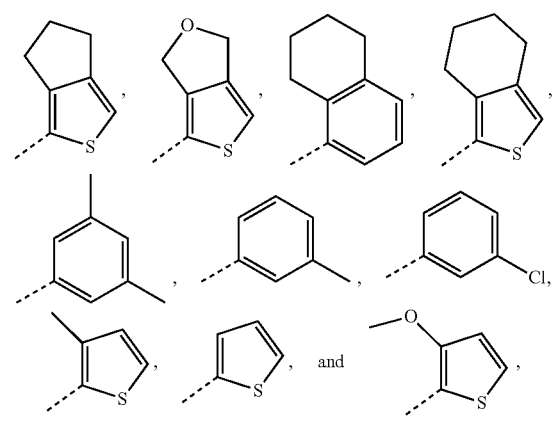

and other variables are as defined in the present disclosure.

In some solutions of the present disclosure, the ring B is selected from

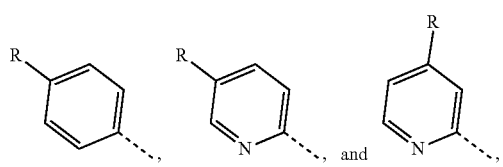

and other variables are as defined in the present disclosure.

In some solutions of the present disclosure, the ring B is selected from

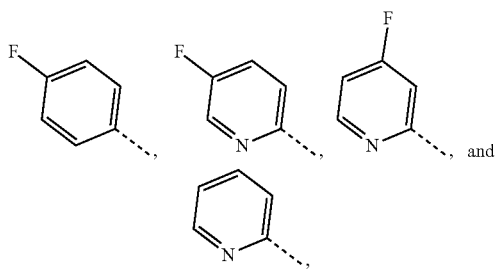

and other variables are as defined in the present disclosure.

The present disclosure provides a compound represented by formula (I), an isomer thereof, or a pharmaceutically acceptable salt thereof,

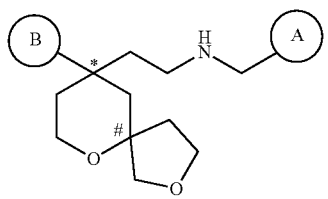

(I)

wherein ring A is selected from a 6-10 membered aryl group and a 5-10 membered heterocyclic group, wherein the 6-10 membered aryl group or 5-10 membered heterocyclic group is optionally substituted with 1, 2, or 3 R;

ring B is selected from phenyl and pyridyl, wherein the phenyl or pyridyl is optionally substituted with 1, 2, or 3 R, wherein R is each independently selected from H, F, Cl, Br, I, OH, $NH_2$, $C_{1-3}$ alkyl, and $C_{1-3}$ alkoxy, wherein the $C_{1-3}$ alkyl or $C_{1-3}$ alkoxy is optionally substituted with 1, 2, or 3 R';

R' is selected from: F, Cl, Br, I, OH, and $NH_2$;

a carbon atom with "*" is a chiral carbon atom, which exists in the form of a single (R) or (S) enantiomer or in the form enriched in one enantiomer;

a carbon atom with "#" is a chiral carbon atom, which exists in the form of a single (R) or (S) enantiomer or in the form enriched in one enantiomer; and the 5-10 membered heterocyclic group contains 1, 2, 3, or 4 heteroatoms or heteroatomic groups independently selected from —NH—, —O—, —S—, and N.

In some solutions of the present disclosure, the R is each independently selected from H, F, Cl, Br, I, OH, $NH_2$, Me, Et, and

wherein the Me, Et, or

is optionally substituted with 1, 2, or 3 R', and other variables are as defined in the present disclosure.

In some solutions of the present disclosure, the R is each independently selected from H, F, Cl, Br, I, OH, $NH_2$, CN, Me, $CH_2F$, $CHF_2$, $CF_3$, Et, and

and other variables are as defined in the present disclosure.

In some solutions of the present disclosure, the ring A is selected from phenyl, thienyl, 5,6-dihydro-4H-cyclopenta[c]thienyl, 1,3-dihydrothieno[3,4-c]furanyl, 1,3-dihydrothieno[3,4-c]furanyl, 2,3-dihydro-1H-indene, 4,5,6,7-tetrahydrobenzo[c]thiophene, and 1,2,3,4-tetrahydronaphthyl, wherein the phenyl, thienyl, 5,6-dihydro-4H-cyclopenta[c]thienyl, 1,3-dihydrothieno[3,4-c]furanyl, 1,3-dihydrothieno[3,4-c]furanyl, 2,3-dihydro-1H-indene, 4,5,6,7-tetrahydrobenzo[c]thiophene, and 1,2,3,4-tetrahydronaphthyl are optionally substituted with 1, 2, or 3 R, and other variables are as defined in the present disclosure.

In some solutions of the present disclosure, the ring A is selected from

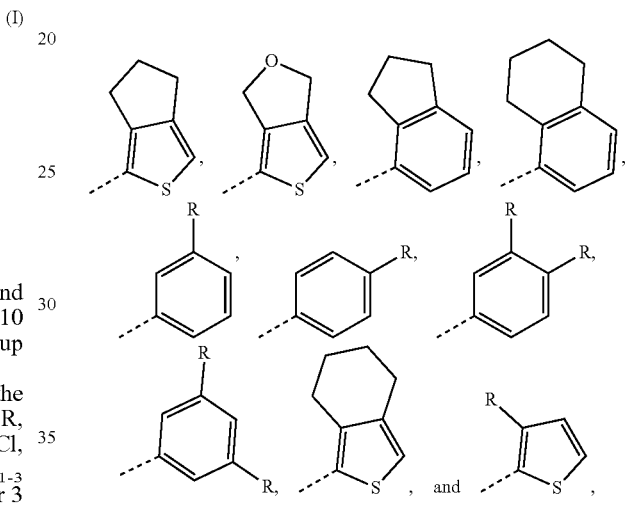

and other variables are as defined in the present disclosure.

In some solutions of the present disclosure, the ring A is selected from

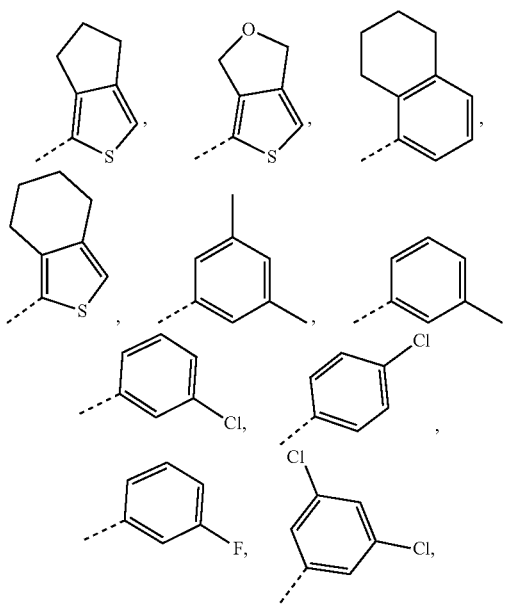

-continued

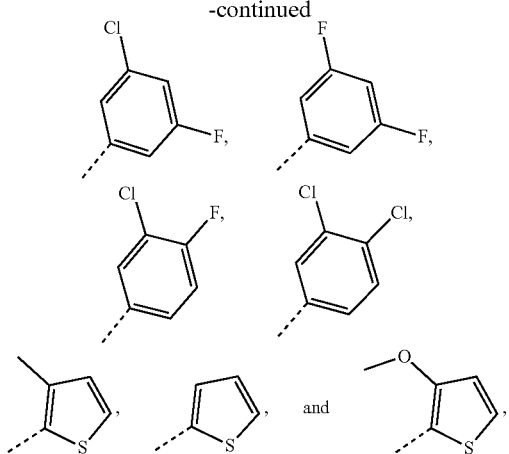

and other variables are as defined in the present disclosure.

In some solutions of the present disclosure, the ring B is selected from

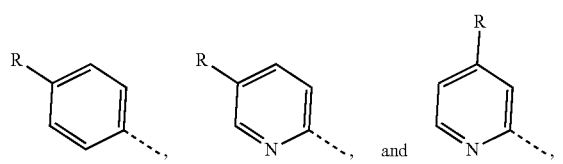

and other variables are as defined in the present disclosure.

In some solutions of the present disclosure, the ring B is selected from

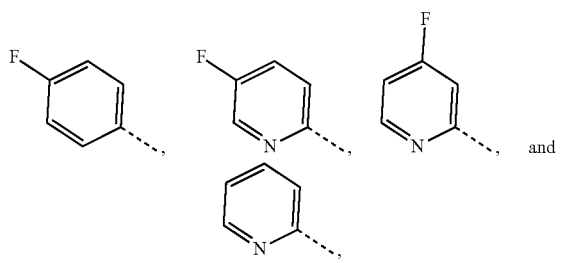

and other variables are as defined in the present disclosure.

The present disclosure provides a compound represented by formula (I), an isomer thereof, or a pharmaceutically acceptable salt thereof,

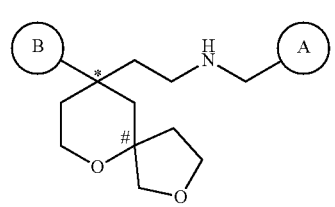 (I)

wherein ring A is selected from phenyl and a 5-10 membered heterocyclic group, wherein the phenyl or 5-10 membered heterocyclic group is optionally substituted with 1, 2, or 3 R;

ring B is selected from phenyl and pyridyl, wherein the phenyl or pyridyl is optionally substituted with 1, 2, or 3 R, wherein R is each independently selected from H, F, Cl, Br, I, OH, $NH_2$, $C_{1-3}$ alkyl, and $C_{1-3}$ alkoxy, wherein the $C_{1-3}$ alkyl or $C_{1-3}$ alkoxy is optionally substituted with 1, 2, or 3 R', R' is selected from: F, Cl, Br, I, OH, and $NH_2$;

a carbon atom with "*" is a chiral carbon atom, which exists in the form of a single (R) or (S) enantiomer or in the form enriched in one enantiomer;

a carbon atom with "#" is a chiral carbon atom, which exists in the form of a single (R) or (S) enantiomer or in the form enriched in one enantiomer; and the 5-10 membered heterocyclic group contains 1, 2, 3, or 4 heteroatoms or heteroatomic groups independently selected from —NH—, —O—, —S—, and N.

In some solutions of the present disclosure, the R is each independently selected from H, F, Cl, Br, I, OH, $NH_2$, Me, Et, and

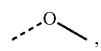

wherein the Me, Et, or

is optionally substituted with 1, 2, or 3 R', and other variables are as defined in the present disclosure.

In some solutions of the present disclosure, the R is each independently selected from H, F, Cl, Br, I, OH, $NH_2$, CN, Me, $CH_2F$, $CHF_2$, $CF_3$, Et, and

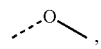

and other variables are as defined in the present disclosure.

In some solutions of the present disclosure, the ring A is selected from phenyl, thienyl, 5,6-dihydro-4H-cyclopenta[c]thienyl, 1,3-dihydrothieno[3,4-c]furanyl, 4,5,6,7-tetrahydrobenzo[c]thiophene, and 1,2,3,4-tetrahydronaphthyl, wherein the phenyl, thienyl, 5,6-dihydro-4H-cyclopenta[c]thienyl, 1,3-dihydrothieno[3,4-c]furanyl, 4,5,6,7-tetrahydrobenzo[c]thiophene, and 1,2,3,4-tetrahydronaphthyl are optionally substituted with 1, 2, or 3 R, and other variables are as defined in the present disclosure.

In some solutions of the present disclosure, the ring A is selected from

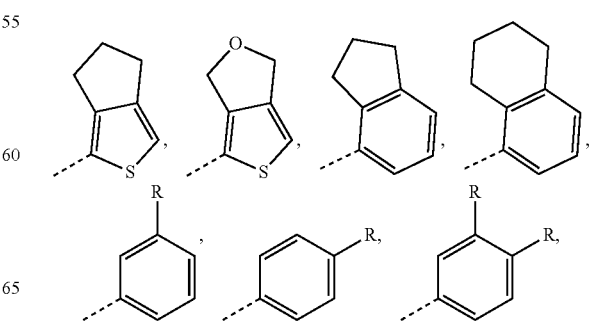

-continued

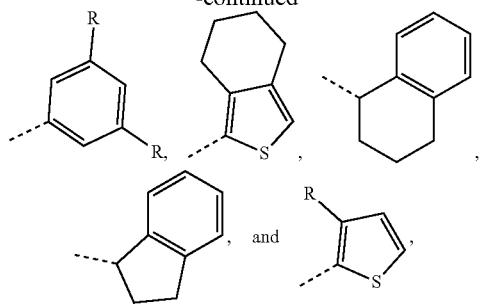

and other variables are as defined in the present disclosure.

In some solutions of the present disclosure, the ring A is selected from

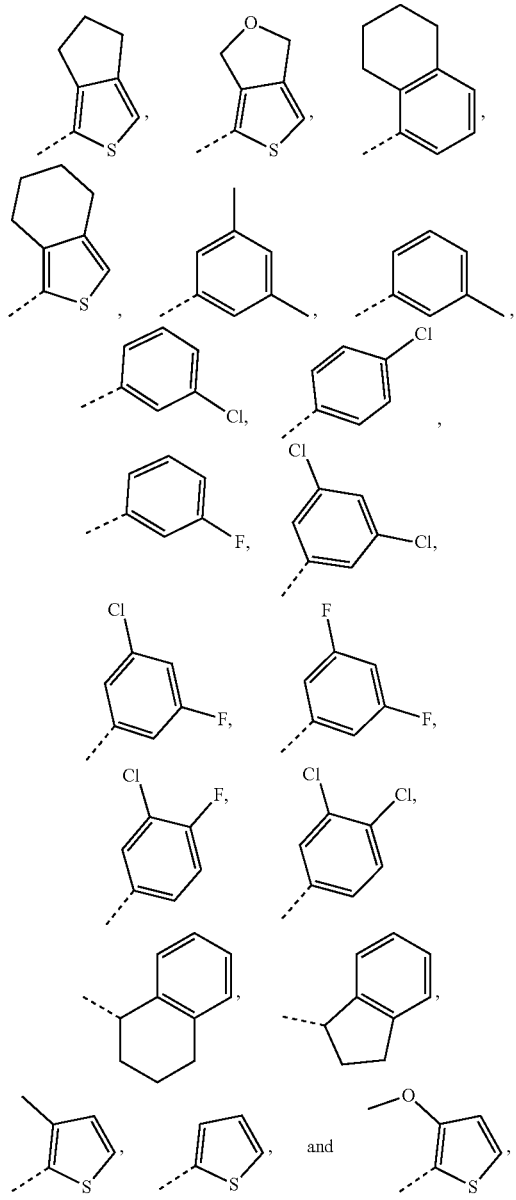

and other variables are as defined in the present disclosure.

In some solutions of the present disclosure, the ring B is selected from

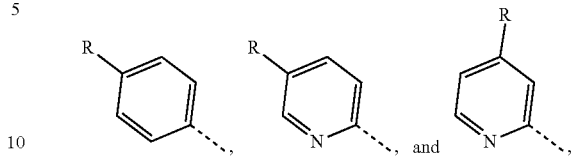

and other variables are as defined in the present disclosure.

In some solutions of the present disclosure, the ring B is selected from

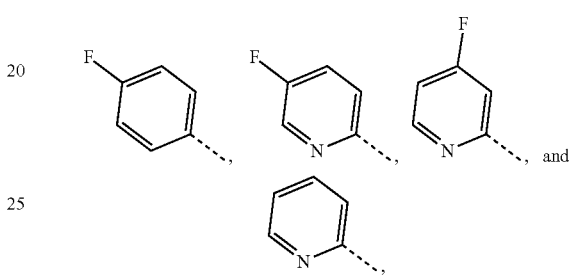

and other variables are as defined in the present disclosure.

Some further solutions of the present disclosure are derived from any combinations of the variables described above.

In some solutions of the present disclosure, the compound, isomer thereof, or pharmaceutically acceptable salt thereof is selected from

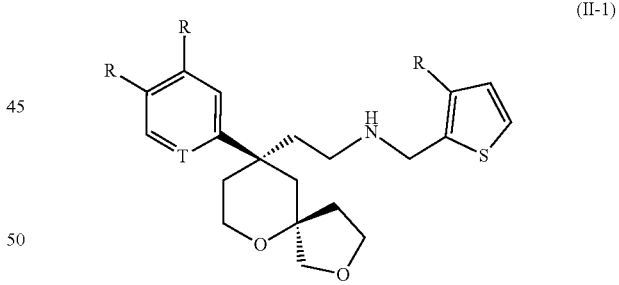

(II-1)

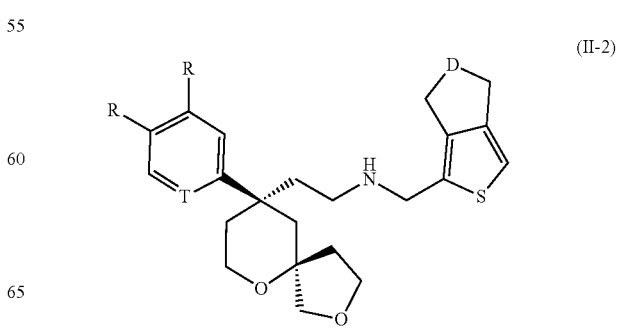

(II-2)

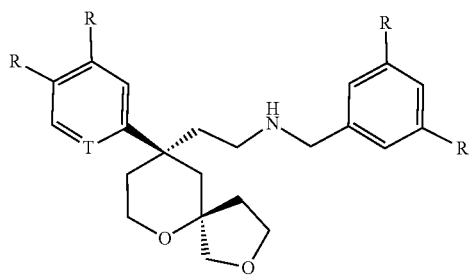
(II-3)
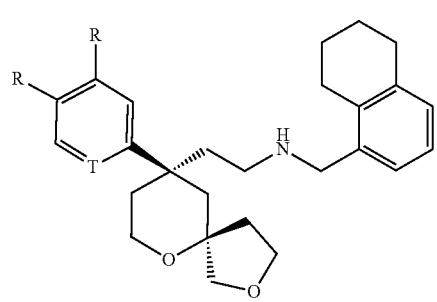
(II-4)
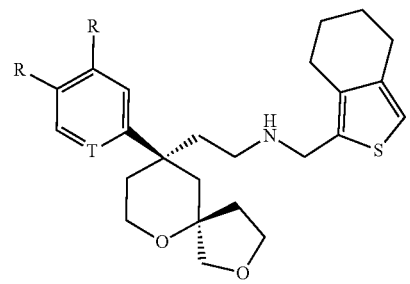
(II-5)
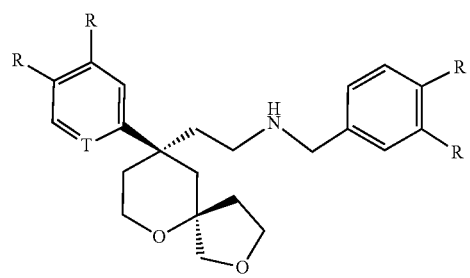
(II-6)
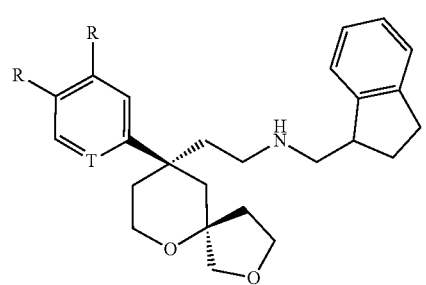
(II-7)
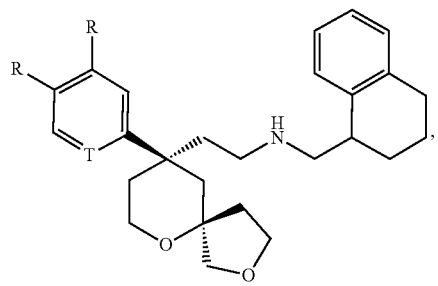
(II-8)
wherein
T is selected from N and CH;
D is selected from O and $CH_2$;
R is as defined in the present disclosure.
In some solutions of the present disclosure, the compound, isomer thereof, or pharmaceutically acceptable salt thereof is selected from
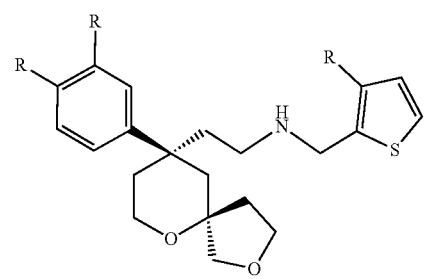
(II-1a)
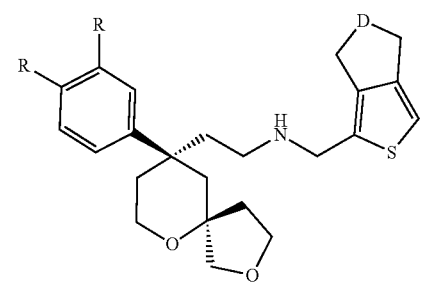
(II-2a)
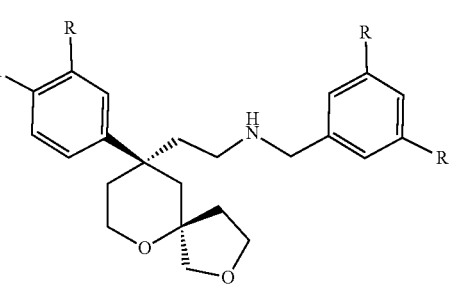
(II-3a)

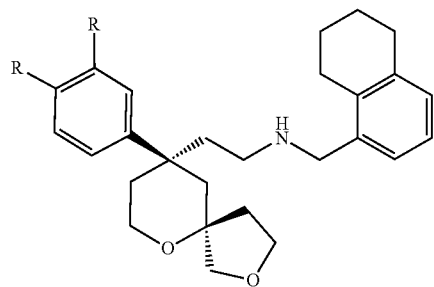
(II-4a)
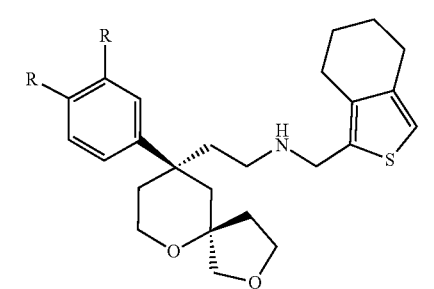
(II-5a)
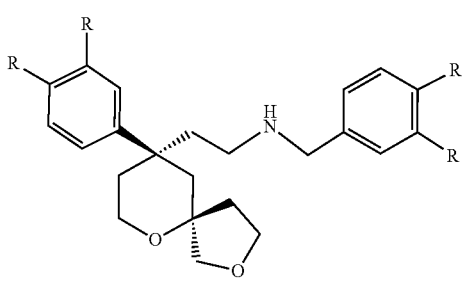
(II-6a)
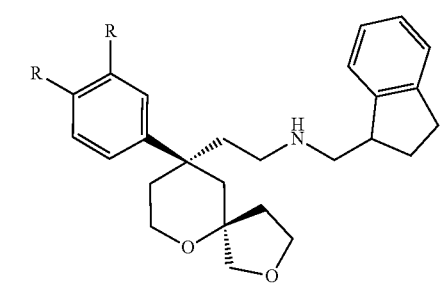
(II-7a)
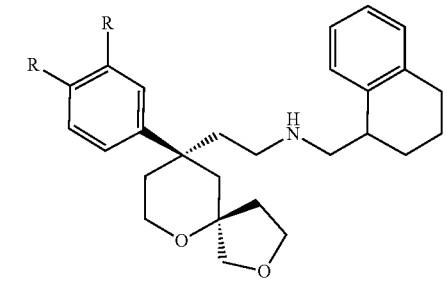
(II-8a)
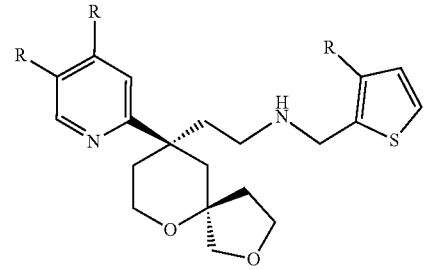
(II-1b)
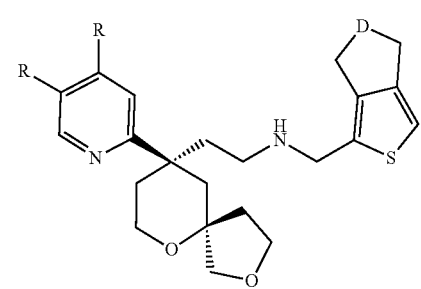
(II-2b)
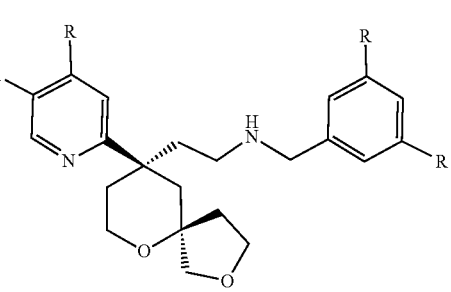
(II-3b)
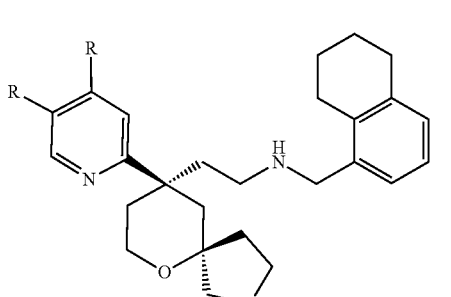
(II-4b)
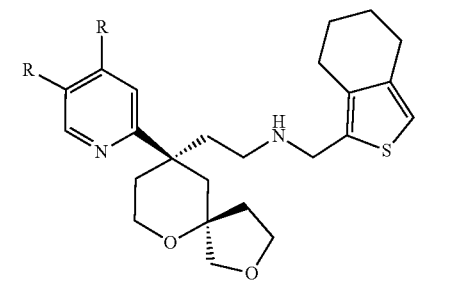
(II-5b)

(II-6b)
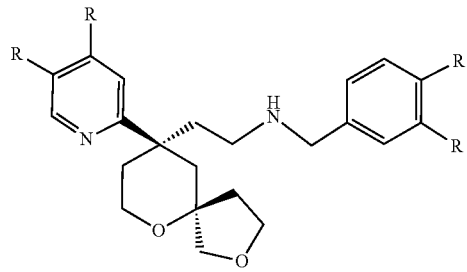
(II-7b)
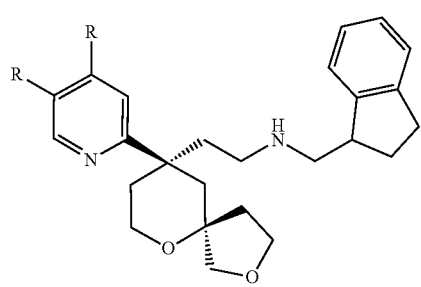
(II-8b)
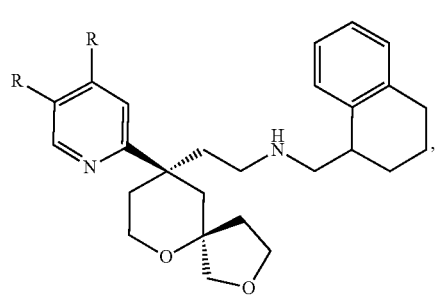
wherein
D is selected from O and $CH_2$;
R is as defined in the present disclosure.
The present disclosure further provides the following compound, isomer thereof, or pharmaceutically acceptable salt thereof, which is selected from
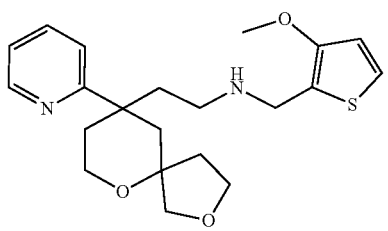
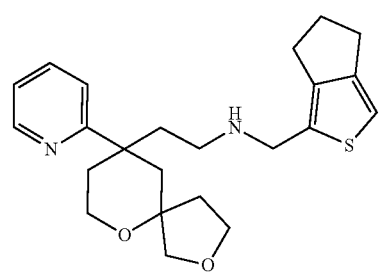
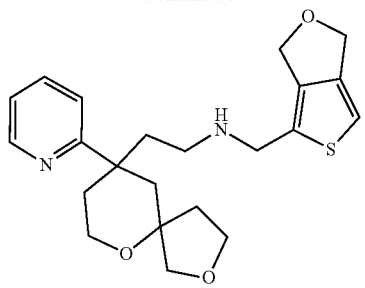
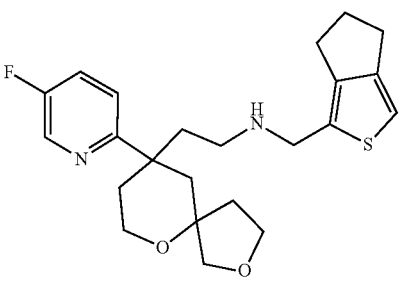
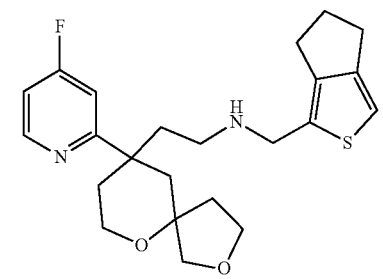
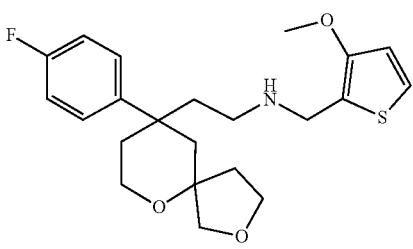
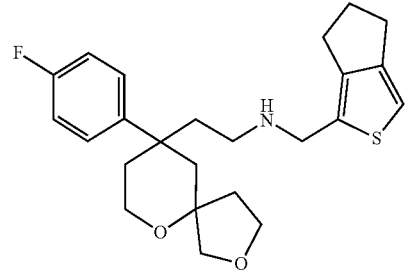
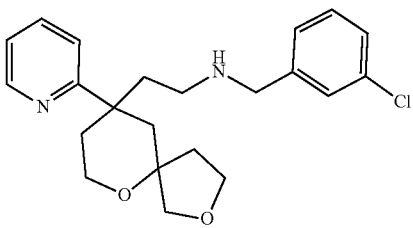

-continued
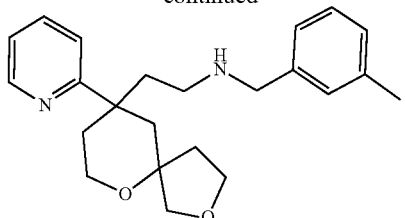
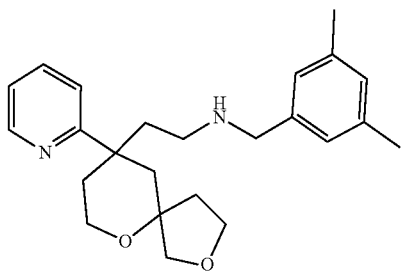
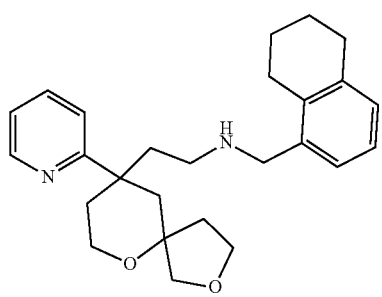
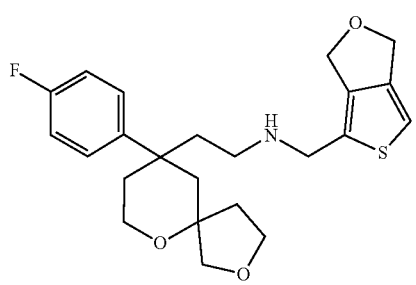
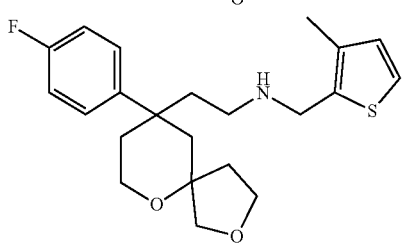
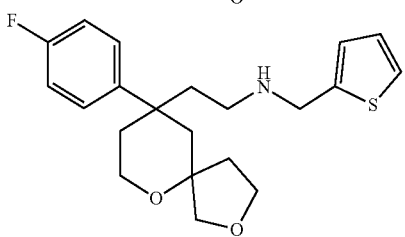
-continued
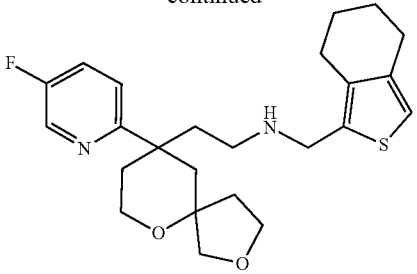
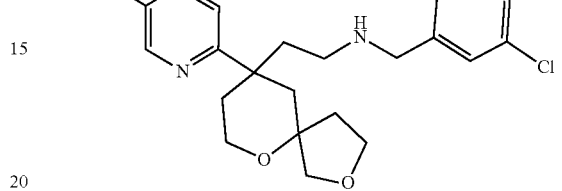
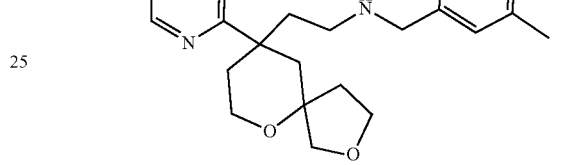
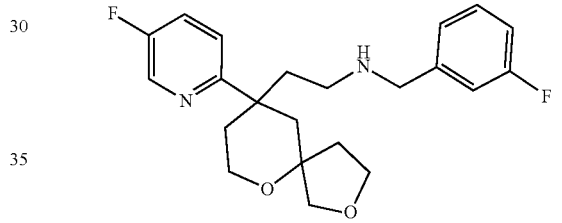
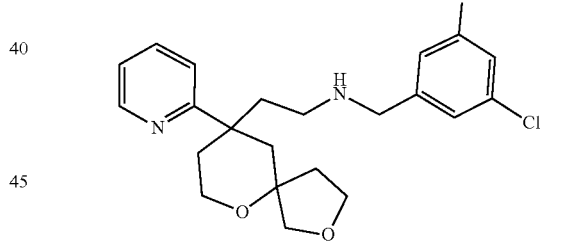
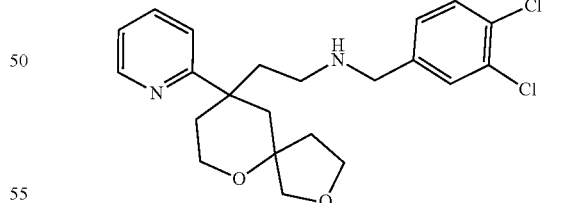
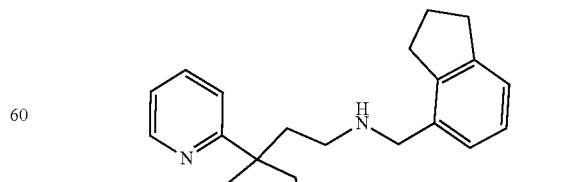
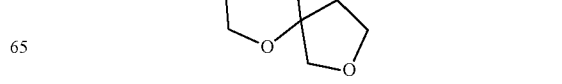

23
-continued
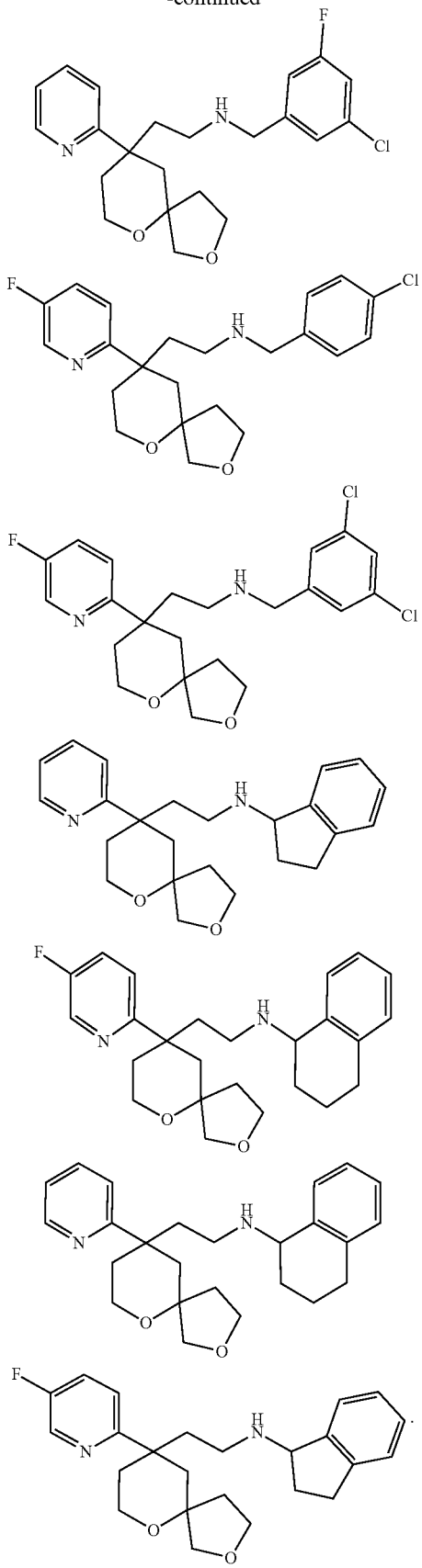
24
In some solutions of the present disclosure, the compound, isomer thereof, or pharmaceutically acceptable salt thereof is selected from
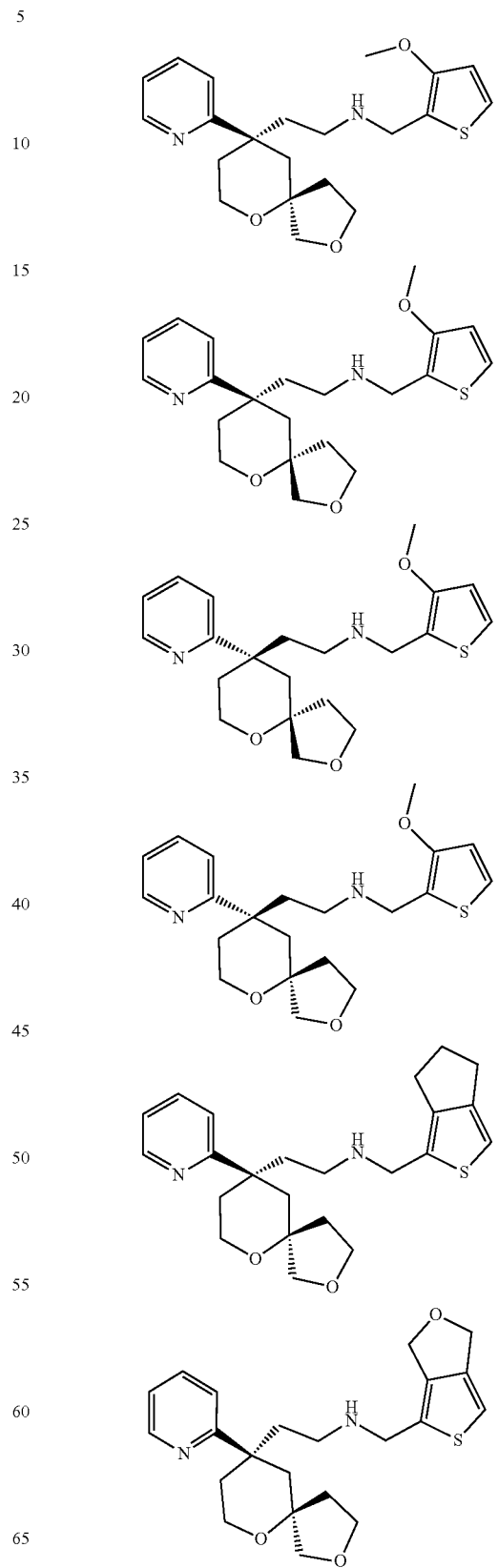

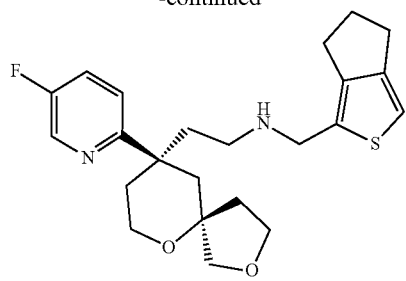
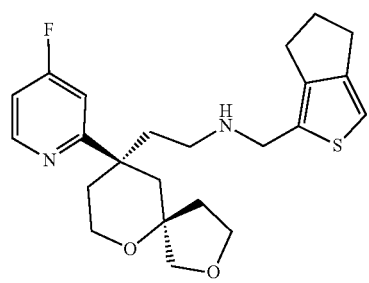
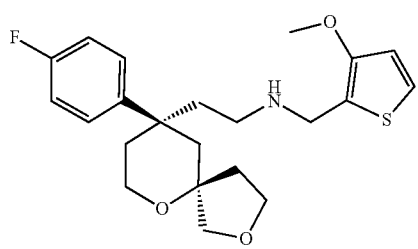
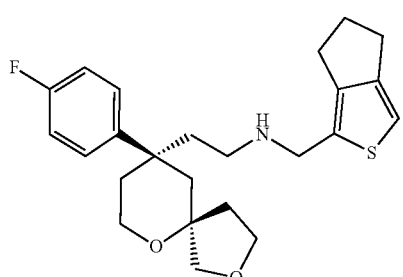
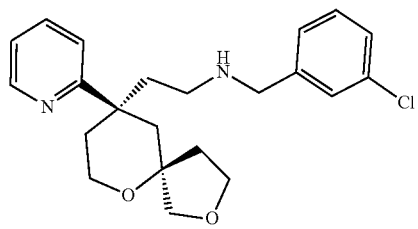
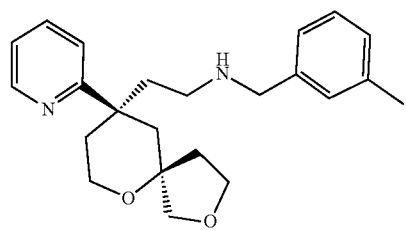
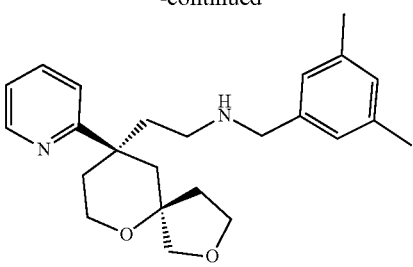
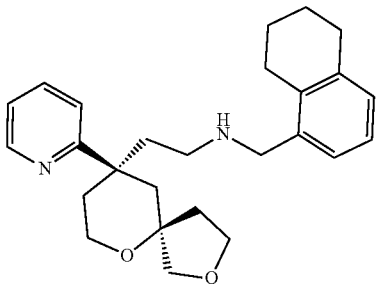
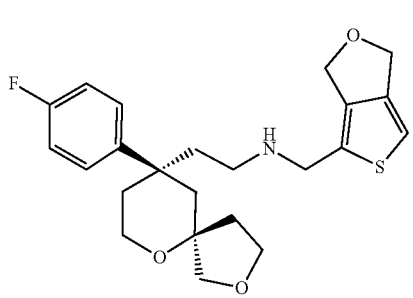
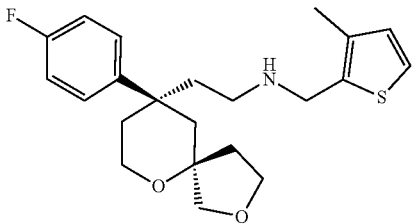
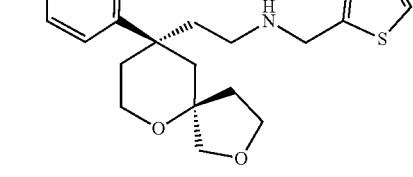
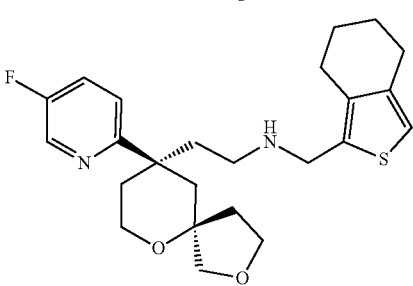

-continued
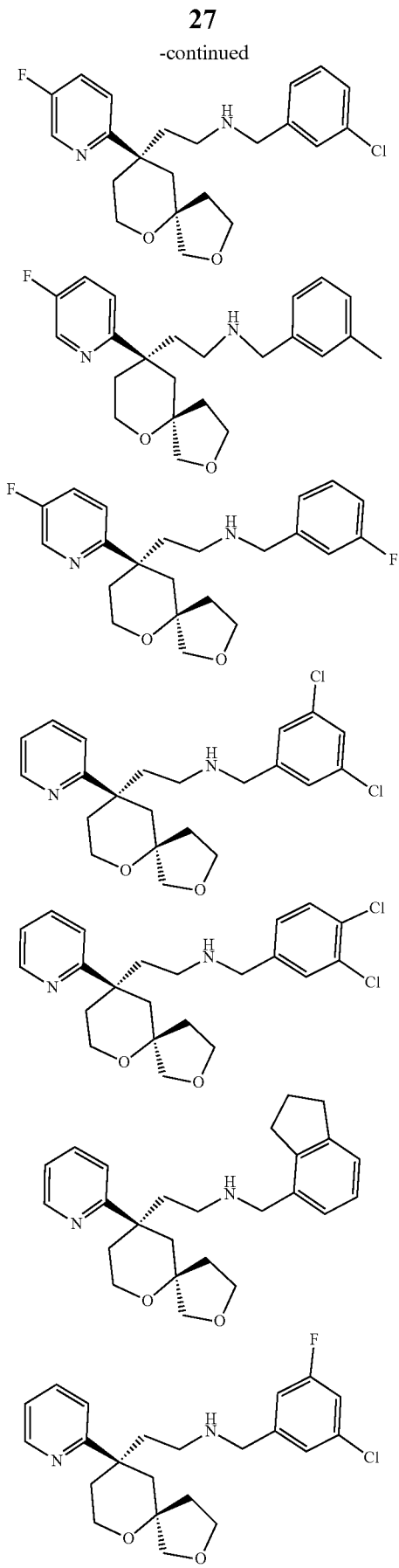
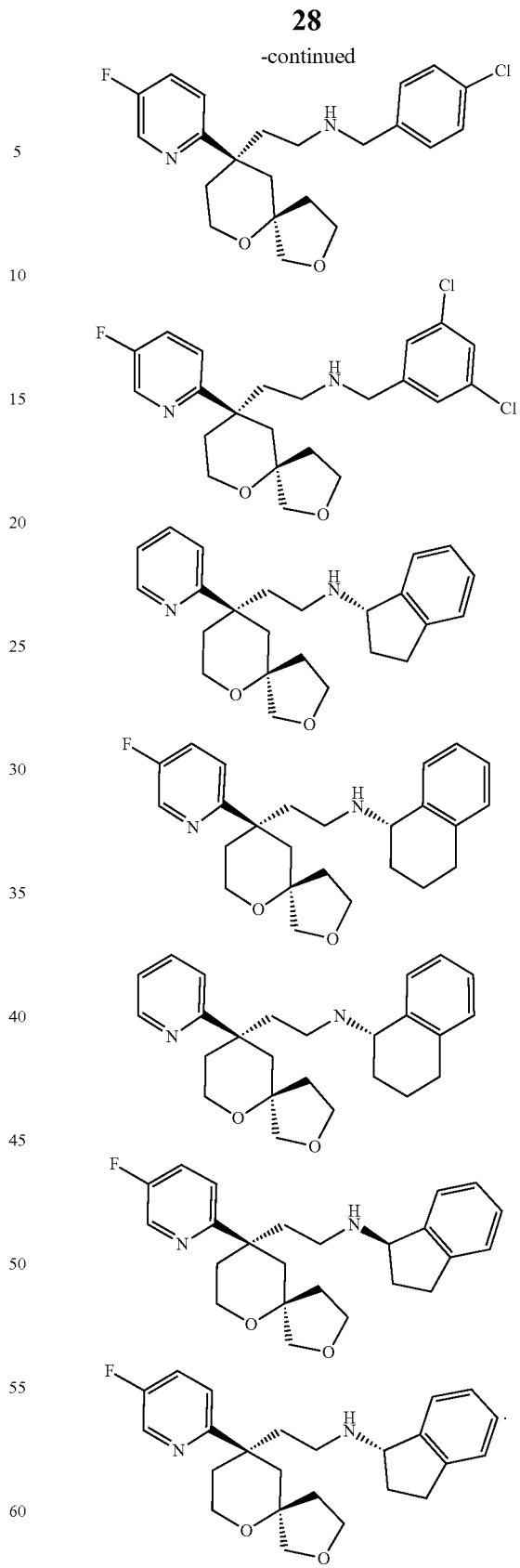
The present disclosure further provides a pharmaceutical composition, comprising a therapeutically effective amount of a compound or a pharmaceutically acceptable salt thereof described above acting as an active ingredient, and a pharmaceutically acceptable carrier.

The present disclosure further provides use of a compound, an isomer thereof, or a pharmaceutically acceptable salt thereof described above or a composition described above in the preparation of a medicament associated with an agonist for μ receptor which is an opioid receptor.

In some solutions of the present disclosure, the medicament associated with an agonist for μ receptor which is an opioid receptor is a medicament for treating pain and pain-related disorders.

Definition and Description

Unless otherwise stated, the following terms and phrases used herein are intended to have the following meanings. A particular term or phrase should not be considered indefinite or unclear in the absence of a special definition, but should be understood in its ordinary sense. When a trade name appears herein, it is intended to refer to its corresponding commercial product or its active ingredient. The term "pharmaceutically acceptable" is used herein in terms of those compounds, materials, compositions, and/or dosage forms, which are, within the scope of sound medical judgment, suitable for use in contact with the tissues of humans and animals without undue toxicity, irritation, allergic response, or other problems or complications, and commensurate with a reasonable benefit/risk ratio.

The term "pharmaceutically acceptable salt" refers to a salt of a compound of the present disclosure, which is prepared from a compound having particular substituent(s) found in the present disclosure and a relatively non-toxic acid or base. When the compounds of the present disclosure contain relatively acidic functional groups, base-addition salts can be obtained by means of contacting a sufficient amount of a base with a neutral form of such compounds in a pure solution or a suitable inert solvent. Pharmaceutically acceptable base-addition salts include sodium, potassium, calcium, ammonium, organic ammonia or magnesium salts or similar salts. When the compounds of the present disclosure contain relatively basic functional groups, acid-addition salts can be obtained by means of contacting a sufficient amount of an acid with the neutral form of such compounds in a pure solution or a suitable inert solvent. Examples of pharmaceutically acceptable acid-addition salts include: salts of inorganic acids including, for example, hydrochloric acid, hydrobromic acid, nitric acid, carbonic acid, bicarbonate radicals, phosphoric acid, monohydrogen phosphate radicals, dihydrogen phosphate radicals, sulfuric acid, hydrogen sulfate radicals, hydroiodic acid, phosphorous acid, etc.; and salts of organic acids including, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid, and other similar acids; and also include salts of amino acids (such as arginine and the like), and salts of organic acids such as glucuronic acid. Certain particular compounds of the present disclosure contain basic and acidic functional groups, and thus can be converted into any base- or acid-addition salts.

Certain compounds of the present disclosure may exist in non-solvated forms or solvated forms, including hydrated forms. In general, the solvated forms and the non-solvated forms are equivalent and are encompassed within the scope of the present disclosure.

The compounds of the present disclosure may have particular geometrically isomeric or stereoisomeric forms. The present disclosure contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures, such as mixtures enriched in enantiomers or diastereomers, all of which fall within the scope of the present disclosure. Additional asymmetric carbon atoms may be present in a substituent such as an alkyl group. All such isomers as well as mixtures thereof are intended to be included in the scope of the present disclosure.

Unless otherwise stated, the term "enantiomers" or "optical isomers" refers to stereoisomers having a mirror-image relationship to each other.

Unless otherwise stated, the term "cis-trans isomer" or "geometric isomer" is caused by a double bond or single bonds of ring-forming carbon atoms which is/are not freely rotatable.

Unless otherwise stated, the term "diastereomers" refers to stereoisomers in which two or more chiral centers are present in their molecules and there is no mirror-image relationship between the molecules.

Unless otherwise stated, "(D)" or "(+)" means dextrorotary, "(L)" or "(−)" means levorotary, and "(DL)" or "(±)" means racemic.

Unless otherwise stated, an absolute configuration of a stereocenter is represented by a wedged solid line bond (⬧) and a wedged dotted line bond (⬧), a relative configuration of the stereocenter is represented by a straight solid line bond (⬧) and a straight dotted line bond (⬧), and the wedged solid line bond (⬧) or the wedged dotted line bond (⬧) is represented by a wavy line (⬧), or the straight solid line bond (⬧) and the straight dotted line bond (⬧) are represented by wavy line (⬧).

The compounds of the present disclosure may exist in particular forms. Unless otherwise stated, the term "tautomers" or "tautomeric forms" refers to isomers having different functional groups which are in dynamic equilibrium and can be quickly converted to each other at room temperature. If tautomers are possible (e.g., in a solution), the chemical equilibrium of the tautomers can be reached. For example, proton tautomers (also known as prototropic tautomers) include interconversions via migration of a proton, such as keto-enol isomerization and imine-enamine isomerization. Valence tautomers include interconversions by reorganization of some of the bonding electrons. A specific example of the keto-enol tautomerization is the interconversion between two tautomers, pentane-2,4-dione and 4-hydroxypent-3-en-2-one.

Unless otherwise stated, the term "enriched in one isomer", "isomerically enriched", "enriched in one enantiomer", or "enantiomerically enriched" means that the content of one of the isomers or the enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise stated, the term "isomeric excess" or "enantiomeric excess" refers to a difference between relative percentages of two isomers or two enantiomers. For example, if one of the isomers or enantiomers is contained in an amount of 90% and the other isomer or enantiomer is contained in an amount of 10%, the isomeric or enantiomeric excess (ee value) is 80%.

Optically active (R)- and (S)-isomers and D and L isomers can be prepared by chiral synthesis or chiral reagents or other conventional techniques. If one enantiomer of a certain compound of the present disclosure is desired, it can be prepared by asymmetric synthesis or derivatization with a chiral auxiliary, wherein the resulting diastereomeric mixtures are separated and the auxiliary groups are cleaved to provide a pure desired enantiomer. Alternatively, when the molecule contains a basic functional group (such as an amino group) or an acidic functional group (such as a carboxyl group), a diastereomeric salt is formed with an appropriate optically active acid or base, and then diastereomers are resolved by a conventional method well known in the art, and then a pure enantiomer is collected. In addition, the separation of enantiomers and diastereomers is usually accomplished by using chromatography, in which a chiral stationary phase is used and which is optionally combined with chemical derivatization (e.g., the generation of carbamate salt from amine). The compound of the present disclosure may contains an unnatural proportion of an atomic isotope at one or more of the atoms constituting the compound. For example, the compound may be labeled with a radioisotope, such as tritium ($^3H$), iodine-125 ($^{125}I$), or C-14 ($^{14}C$). For another example, hydrogen may be replaced with deuterium to form a deuterated medicament. A bond constituted by deuterium and carbon is stronger than a bond constituted by ordinary hydrogen and carbon. The deuterated medicaments have advantages such as reduced toxic and side effects, increased medicament stability, enhanced therapeutic efficacy, and extended biological half-life of medicaments, compared with non-deuterated medicaments. All isotopic composition variations of the compounds of the present disclosure, whether radioactive or not, are included within the scope of the present disclosure. The term "pharmaceutically acceptable carrier" refers to any formulation or carrier medium capable of delivering an effective amount of the active substance of the present disclosure without interfering with the biological activity of the active substance and without causing toxic and side effects to the host or patient. Representative carriers include water, oils (vegetable and mineral oils), cream base, lotion base, ointment base, and the like. These bases include suspending agents, thickeners, penetration enhancers, and the like. Their formulations are well known to those skilled in the art of cosmetics or topical pharmaceuticals.

"Optional" or "optionally" means that the subsequently described event or circumstance may, but is not necessary to, occur, and that the description includes instances where the event or circumstance occurs and instances where the event or circumstance does not occur.

The term "substituted" means that any one or more hydrogen atoms on a particular atom is replaced with a substituent, which may include deuterium and variants of hydrogen, provided that the valency of the particular atom is normal and that the substituted compound is stable. When a substituent is oxygen (i.e., =O), it means that two hydrogen atoms are substituted. Oxygen substitution does not occur on aromatic groups. The term "optionally substituted" means that it may or may not be substituted, and the type and number of substituents may be arbitrary on the basis that they are chemically achievable, unless otherwise specified.

When any variable (e.g., R) occurs more than once in the composition or structure of the compound, its definition in each case is independent. Thus, for example, if a group is substituted with 0 to 2 R, the group may optionally be substituted with up to two R, and R in each case has its own individual option. In addition, combinations of substituents and/or variants thereof are permissible only if such combinations will result in stable compounds.

When the number of a linking group is 0, such as —(CRR)$_0$—, this indicates that the linking group is a single bond.

When one of the variables is selected from a single bond, this indicates that the two groups connected thereto are directly attached. For example, when L denotes a single bond in A-L-Z, the structure is actually A-Z.

When a substituent is vacant, this indicates that the substituent is absent. For example, when X is vacant in A-X, the structure is actually A. When it is not specified by which atom a listed substituent is connected to the substituted group, such substituent may be bonded by any of its atoms. For example, a pyridyl group acting as a substituent may be connected to a substituted group by any carbon atom in the pyridine ring. When there is no indication of a linking direction for a listed linking group, the linking direction is arbitrary. For example, when a linking group L is -M-W— in

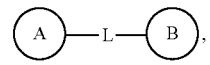

-M-W— may connect ring A and ring B in a direction the same as the reading order from left to right to form

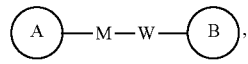

or may connect ring A and ring B in a direction opposite to the reading order from left to right to form

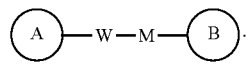

Combinations of the linking groups, substituents, and/or variants thereof are permissible only if such combinations will result in stable compounds.

Unless otherwise specified, the term "hetero" refers to a heteroatom or a heteroatomic group (i.e., an atomic group containing a heteroatom), including atoms other than carbon (C) and hydrogen (H), as well as atomic groups containing such heteroatoms, including, for example, oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)—, or —S(=O)N(H)—.

Unless otherwise specified, "ring" refers to substituted or unsubstituted cycloalkyl, heterocycloalkyl, cycloalkenyl, heterocycloalkenyl, cycloalkynyl, heterocycloalkynyl, aryl, or heteroaryl. The so-called rings include single rings, joined rings, spiro rings, fused rings, or bridged rings. The number of atoms in a ring is usually defined as the member number of the ring. For example, a "5- to 7-membered ring" refers to a ring in which 5 to 7 atoms are arranged. Unless otherwise specified, the ring optionally contains 1 to 3 heteroatoms. Thus, the "5- to 7-membered ring" includes, for example, phenyl, pyridyl, and piperidinyl; on the other hand, the term "5- to 7-membered heterocycloalkyl ring" includes pyridyl and piperidinyl, but excludes phenyl. The term "ring" also includes a ring system containing at least one ring, each "ring" of which independently conforms to the above definition.

Unless otherwise specified, the term "heterocycle" or "heterocyclyl" means stable monocyclic, bicyclic, or tricyclic rings containing heteroatoms or heteroatomic groups, which may be saturated, partially unsaturated, or unsaturated (aromatic) and which contain carbon atoms and 1, 2, 3, or 4 heteroatoms in the ring independently selected from N, O, and S, wherein any of the above heterocycles may be fused to a benzene ring to form a bicyclic ring. Nitrogen and sulfur heteroatoms may optionally be oxidized (i.e., NO and S(O) p, where p is 1 or 2). The nitrogen atom may be substituted or unsubstituted (i.e., N or NR, where R is selected from H or other substituents that have been defined herein). The heterocycle may be attached to the pendant group of any heteroatom or carbon atom, so as to form a stable structure. If the resulting compound is stable, the heterocycle described herein may undergo substitution at the carbon or nitrogen position. The nitrogen atom in the heterocycle is optionally quaternized. In a preferred solution, when the total number of S and O atoms in the heterocycle exceeds 1, these heteroatoms are not adjacent to each other. In another preferred solution, the total number of S and O atoms in the heterocycle does not exceed 1. As used herein, the term "aromatic heterocyclic group" or "heteroaryl" means a stable 5-, 6-, or 7-membered monocyclic or bicyclic ring, or 7-, 8-, 9-, or 10-membered bicyclic heterocyclyl aromatic ring, which contains carbon atoms and 1, 2, 3, or 4 heteroatoms in the ring independently selected from N, O, and S. The nitrogen atom may be substituted or unsubstituted (i.e., N or NR, where R is selected from H or other substituents that have been defined herein). Nitrogen and sulfur heteroatoms may optionally be oxidized (i.e., NO and S(O)p, where p is 1 or 2). It is worth noting that the total number of S and O atoms in the aromatic heterocycle does not exceed 1. Bridged rings are also included in the definition of heterocycle. A bridged ring is formed when one or more atoms (i.e., C, O, N, or S) connect two non-adjacent carbon atoms or nitrogen atoms. Preferred bridged rings include, but are not limited to, one carbon atom, two carbon atoms, one nitrogen atom, two nitrogen atoms, and one carbon-nitrogen group. It is worth noting that a bridge bond always converts a monocyclic ring to a tricyclic ring. In a bridged ring, a substituent in the ring may also appear on the bridge bond.

Examples of heterocyclic compounds include, but are not limited to, acridinyl, azocinyl, benzimidazolyl, benzofuranyl, benzothiofuryl, benzothiophenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolialkenyl, indolinyl, indolizinyl, indolyl, 3H-indolyl, isobenzofuranyl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazine, phenothiazine, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridoxazole, pyridimidazole, pyridothiazole, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuranyl, tetrahydroisoquinolyl, tetrahydroquinolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrene, thiazolyl, isothiazolyl thienyl, thienoxazolyl, thienothiazolyl, thienoimidazolyl, thienyl, triazinyl, 1H-1,2,3-triazolyl, 2H-1,2,3-triazolyl,1H-1,2,4-triazolyl, 4H-1,2,4-triazolyl, and xanthenyl, and also include fused-ring and spiro compounds.

Unless otherwise specified, the term "hydrocarbyl" or its subordinate concept (such as alkyl, alkenyl, alkynyl, aryl, or the like), by itself or as part of another substituent, refers to a linear, branched, or cyclic hydrocarbon radical, or a combination thereof, which may be fully saturated (e.g., alkyl), mono- or polyunsaturated (e.g., alkenyl, alkynyl, aryl), may be mono-substituted or polysubstituted, may be monovalent (e.g., methyl), divalent (e.g., methylene), or polyvalent (e.g., methine), and may include divalent or polyvalent radicals, with a designated number of carbon atoms (for example, $C_1$-$C_{12}$ represents 1 to 12 carbons, $C_{1\text{-}12}$ is selected from $C_1$, $C_2$, $C_3$, $C_4$, $C_5$, $C_6$, $C_7$, $C_8$, $C_9$, $C_{10}$, $C_{11}$, and $C_{12}$, and $C_{3\text{-}12}$ is selected from $C_3$, $C_4$, $C_5$, $C_6$, $C_7$, $C_8$, $C_9$, $C_{10}$, $C_{11}$, and $C_{12}$). "Hydrocarbyl" includes, but is not limited to, aliphatic hydrocarbyl and aromatic hydrocarbyl. The aliphatic hydrocarbyl includes chain and ring structures, specific examples of which include, but are not limited to, alkyl, alkenyl, and alkynyl. The aromatic hydrocarbyl includes, but is not limited to, 6- to 12-membered aromatic hydrocarbyl such as benzene, naphthalene, and the like. In some embodiments, the term "hydrocarbyl" refers to a linear or branched chain radical or a combination thereof, which may be fully saturated or mono- or polyunsaturated, and may include divalent and polyvalent radicals. Examples of saturated hydrocarbon radicals include, but are not limited to, methyl, ethyl, n-propyl, isopropyl, n-butyl, t-butyl, isobutyl, secbutyl, isobutyl, cyclohexyl, (cyclohexyl) methyl, cyclopropylmethyl, and homologs or isomers of n-pentyl, n-hexyl, n-heptyl, n-octyl, and other radicals. Unsaturated hydrocarbyl has one or more double or triple bonds, and examples thereof include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the term "heterohydrocarbyl" or its subordinate concept (such as heteroalkyl, heteroalkenyl, heteroalkynyl, heteroaryl, or the like), by itself or in combination with another term, refers to a stable linear, branched, or cyclic hydrocarbon radical, consisting of a certain number of carbon atoms and at least one heteroatom, or a combination thereof. In some embodiments, the term "heteroalkyl", by itself or in combination with another term, refers to a stable linear or branched chain alkyl radical, consisting of a certain number of carbon atoms and at least one heteroatom, or a combination thereof. In a typical embodiment, the heteroatom is selected from B, O, N, and S, wherein the nitrogen and sulfur atoms are optionally oxidized and the nitrogen heteroatom is optionally quaternized. The heteroatom or heteroatomic group may be located at any internal position of the heterohydrocarbyl, including the position at which the hydrocarbyl is connected to the rest of the molecule. However, the terms "alkoxy", "alkylamino", and "alkylthio" (or thioalkoxy) are the customary expressions and refer to those alkyl groups which are connected to the rest of the molecule via an oxygen atom, an amino group, or a sulfur atom, respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH═CH—O—$CH_3$, —$CH_2$—CH═N—O$CH_3$, and —CH═CH—N($CH_3$)—$CH_3$. Up to two heteroatoms may be consecutive, for example, —$CH_2$—NH—O$CH_3$.

Unless otherwise specified, the terms "cyclohydrocarbyl", "heterocyclohydrocarbyl", or subordinate concept thereof (such as aryl, heteroaryl, cycloalkyl, heterocycloalkyl, cycloalkenyl, heterocycloalkenyl, cycloalkynyl, heterocycloalkynyl, or the like), by itself or in combination with other terms, refer to cyclized "hydrocarbyl" and "heterohydrocarbyl", respectively. In addition, as for heterohydrocarbyl or heterocyclohydrocarbyl (such as heteroalkyl, heterocycloalkyl), a heteroatom may occupy the position at which the heterocycle is attached to the rest of the molecule. Examples of cyclohydrocarbyl include, but are not limited to, cyclopentyl, cyclohexyl, 1-cyclohexenyl, 3-cyclohexenyl, cycloheptyl, and the like. Non-limited examples of heterocyclyl include 1-(1,2,5,6-tetrahydropyridinyl), 1-piperidinyl, 2-piperidinyl, 3-piperidinyl, 4-morpholinyl, 3-morpholinyl, tetrahydrofuran-2-yl, tetrahydrofuran indol-3-yl, tetrahydrothiophen-2-yl, tetrahydrothiophen-3-yl, 1-piperazinyl, and 2-piperazinyl.

Unless otherwise specified, the term "heterocycloalkyl", by itself or in combination with other terms, refers to a cyclized "heteroalkyl". In addition, as for the "heterocycloalkyl", a heteroatom may occupy the position at which the heterocycloalkyl is connected to the rest of the molecule. In some embodiments, the heterocycloalkyl is a 4- to 6-membered heterocycloalkyl group. In other embodiments, the heterocycloalkyl is a 5- or 6-membered heterocycloalkyl group. Examples of heterocycloalkyl include, but are not limited to, azetidinyl, oxetanyl, thietanyl, pyrrolidinyl, pyrazolidinyl, imidazolidinyl, tetrahydrothienyl, tetrahydrofuranyl, tetrahydropyranyl, piperidinyl, piperazinyl, morpholinyl, dioxanyl, dithianyl, isoxazolidinyl, isothiazolidinyl, 1,2-oxazinyl, 1,2-thiazinyl, hexahydropyridazinyl, homopiperazinyl, homopiperidinyl, or oxa-cycloheptanyl.

Unless otherwise specified, the term "alkyl" is used to denote a linear or branched saturated hydrocarbon group, which may be mono-substituted (e.g., —$CH_2$F) or poly-substituted (e.g., —$CF_3$), and may be monovalent (e.g., methyl), divalent (e.g., methylene), or polyvalent (e.g., methine). Examples of alkyl include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl), etc.

Unless otherwise specified, cycloalkyl includes any stable cyclic or polycyclic hydrocarbyl, in which any carbon atom is saturated, and which may be mono-substituted or poly-substituted, and may be monovalent, divalent, or polyvalent. Examples of these cycloalkyls include, but are not limited to, cyclopropyl, norbornyl, [2.2.2] bicyclooctane, [4.4.0] bicyclodecane, and the like.

Unless otherwise specified, the term "halo" or "halogen", by itself or as part of another substituent, refers to a fluorine, chlorine, bromine, or iodine atom. Furthermore, the term "haloalkyl" is meant to include monohaloalkyl and polyhaloalkyl. For example, the term "halo ($C_1$-$C_4$) alkyl" is meant to include, but is not limited to, trifluoromethyl, 2,2,2-trifluoroethyl, 4-chlorobutyl, 3-bromopropyl, and the like. Unless otherwise specified, examples of haloalkyl include, but are not limited to, trifluoromethyl, trichloromethyl, pentafluoroethyl, and pentachloroethyl.

"Alkoxy" denotes the above-mentioned alkyl group having a specific number of carbon atoms and connected through an oxygen bridge, and $C_{1-6}$ alkoxy includes $C_1$, $C_2$, $C_3$, $C_4$, $C_5$, and $C_6$ alkoxy groups unless otherwise specified. Examples of alkoxy include, but are not limited to: methoxy, ethoxy, n-propoxy, isopropoxy, n-butoxy, sec-butoxy, t-butoxy, n-pentyloxy, and S-pentyloxy.

Unless otherwise specified, the term "aryl" refers to a polyunsaturated aromatic hydrocarbon substituent, which may be mono-substituted or polysubstituted, may be monovalent, divalent, or polyvalent, and may be monocyclic or polycyclic (such as 1 to 3 rings, where at least one ring is aromatic), which are fused together or covalently linked. The term "heteroaryl" refers to an aryl (or ring) containing one to four heteroatoms. In one illustrative example, the heteroatom is selected from B, N, O, and S, wherein the nitrogen and sulfur atoms are optionally oxidized and the nitrogen atom is optionally quaternized. Heteroaryl may be connected to the rest of the molecule via the heteroatom. Non-limited examples of aryl or heteroaryl include phenyl, naphthyl, biphenyl, pyrrolyl, pyrazol, imidazolyl, pyrazinyl, oxazolyl, phenyl-oxazolyl, isoxazolyl, thiazolyl, furyl, thienyl, pyridyl, pyrimidinyl, benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazol, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Any one of the above aryl and heteroaryl cyclic substituents is selected from acceptable substituents described below.

Unless otherwise specified, aryl, when used in combination with other terms (e.g., aryloxy, arylthio, aralkyl), includes aryl and heteroaryl rings as defined above. Thus, the term "aralkyl" is meant to include those radicals in which an aryl is attached to an alkyl (e.g., benzyl, phenethyl, pyridylmethyl, and the like), including those alkyl groups in which a carbon atom (such as methylene) has been replaced by an atom such as an oxygen atom, for example, phenoxymethyl, 2-pyridyloxymethyl 3-(1-naphthyloxy)propyl, and the like.

The term "leaving group" refers to a functional group or atom that can be substituted by another functional group or atom by a substitution reaction (e.g., a nucleophilic substitution reaction). For example, representative leaving groups include triflate; chlorine, bromine, iodine; sulfonate groups, such as mesylate, tosylate, brosylate, p-toluenesulfonate and the like; acyloxy groups, such as acetoxy, trifluoroacetoxy and the like.

The term "protecting group" includes, but is not limited to, "amino protecting group", "hydroxy protecting group", or "thiol protecting group". The term "amino protecting group" refers to a protecting group suitable for preventing side reactions at the nitrogen position of amino. Representative amino protecting groups include, but are not limited to, formyl; acyl such as alkanoyl (e.g., acetyl, trichloroacetyl, or trifluoroacetyl); alkoxycarbonyl such as tert-butoxycarbonyl (Boc); arylmethoxycarbonyl, such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl)methyl; silyl, such as trimethylsilyl (TMS) and tert-butyldimethylsilyl (TBS) and the like. The term "hydroxy protecting group" refers to a protecting group suitable for preventing side reactions of hydroxyl groups. Representative hydroxyl protecting groups include, but are not limited to, alkyl, such as methyl, ethyl and t-butyl; acyl, such as alkanoyl (e.g., acetyl); arylmethyl, such as benzyl (Bn), p-methoxylbenzyl (PMB), 9-fluorenylmethyl (Fm) and diphenylmethyl (benzhydryl, DPM); silyl, such as trimethylsilyl (TMS) and tert-butyldimethylsilyl (TBS) and the like.

The compounds of the present disclosure may be prepared by a variety of synthesis methods well known to those skilled in the art, including the specific embodiments listed below, embodiments formed by their combinations with other chemical synthesis methods, and the equivalent alternatives well known to those skilled in the art. Preferred embodiments include, but are not limited to, examples of the present disclosure.

Solvents used in the present disclosure are commercially available. The following abbreviations are used in the present disclosure: aq stands for aqueous; HATU stands for O-(7-azabenzotriazole-1-yl)-N, N, N',N'-tetramethyluronium hexafluorophosphate; EDC stands for N-(3-dimethylaminopropyl)-N'-ethylcarbodiimide hydrochloride; m-CPBA stands for 3-chloroperoxybenzoic acid; eq stands for equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH stands for methanol; CBz stands for benzyloxycarbonyl, which is an amine protecting group; BOC stands for tert-butyloxycarbonyl, which is an amine protecting group; HOAc stands for acetic acid; $NaCNBH_3$ stands for sodium cyanoborohydride; r.t. stands for room temperature; O/N stands for overnight; THF stands for tetrahydrofuran; $Boc_2O$ stands for di-tert-butyl dicarbonate; TFA stands for trifluoroacetic acid; DIPEA stands for diisopropyl ethylamine; $SOCl_2$ stands for thionyl chloride; mp stands for melting point; DEA stands for diethylamine; ACN stands for acetonitrile; and HEPES stands for 4-hydroxyethyl piperazine ethanesulfonic acid.

Compounds are named manually or with ChemDraw® software, and commercial compounds are available under Supplier Directory Name.

Technical Effects preferred compounds of examples of the present disclosure exhibit significant agonistic effects on the μ-receptor-mediated cAMP signaling pathway, but exhibit no agonistic effects or weak agonistic properties on the β-arrestin signaling pathway. The preferred compounds of the examples of the present disclosure are significantly more biased toward the Gi signaling pathway than TRV-130, indicating that fewer adverse reactions associated with the β-arrestin signaling pathway will be caused in vivo.

BRIEF DESCRIPTION OF DRAWINGS

FIG. 1: Percent of analgesic effect (%) in rat hot plate test.

Percent of analgesic effect=(test group−solvent control group)/(20−solvent control group)×100%

Data in the FIGURE are shown as mean±standard error, where n=10/group, *p<0.05, p<0.01, *p<0.001. Comparison with the solvent group is performed using one-way analysis of variance plus Dunnett's multiple comparison test.

DETAILED DESCRIPTION OF EMBODIMENTS

The present disclosure will be described in detail by way of examples, but the present disclosure is not intended to be adversely limited in any way. The present disclosure has been described in detail herein, and its specific embodiments are also disclosed. It will be obvious to those skilled in the art that various changes and modifications can be made to the specific embodiments of the present disclosure without departing from the spirit and scope of the present disclosure.

Reference Example 1: Synthesis of Intermediate L1

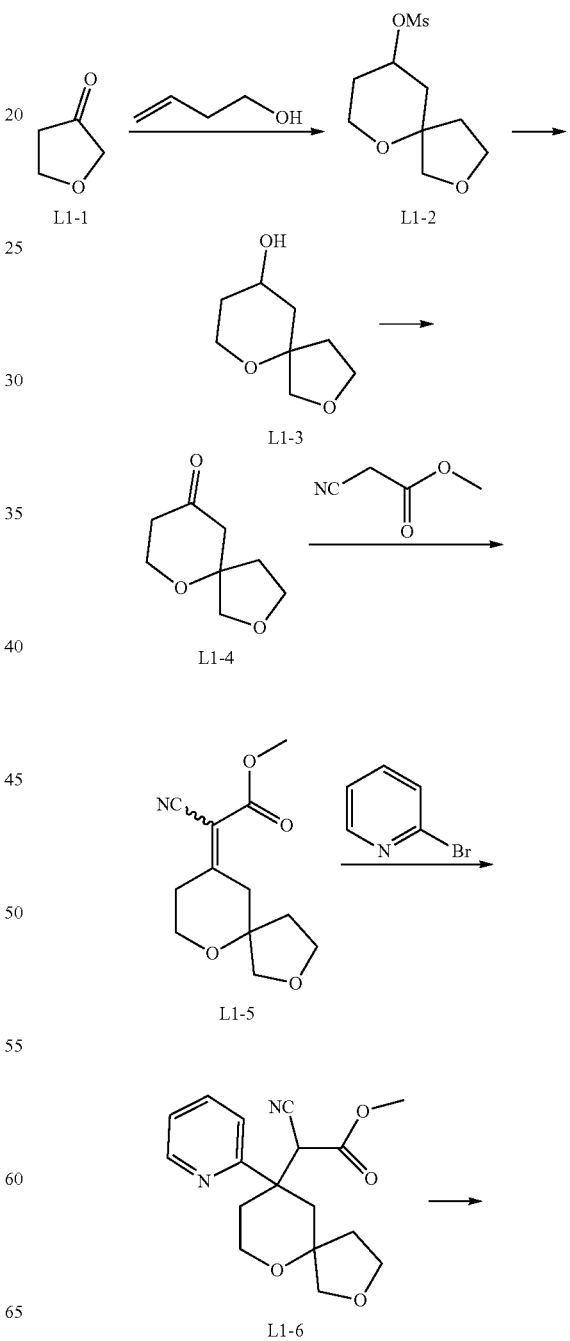

-continued

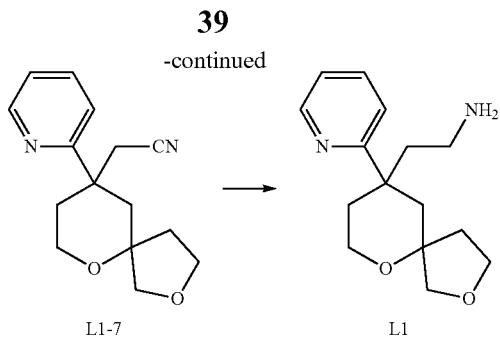

L1-7      L1

Step 1: Preparation of Compound L1-2

A compound L1-1 (17.4 g, 201.7 mmol) was dissolved in dichloromethane (500.0 mL) at 25° C., 3-buten-1-ol (14.54 g, 201.65 mmol) was added, and then methanesulfonic acid (58.1 g, 605.0 mmol) was slowly added dropwise to the system. After the addition was completed, the reaction was continued for 16 hours. A saturated aqueous sodium bicarbonate solution was added to the reaction solution until pH=8, and the aqueous phase was extracted with dichloromethane (200 mL×3). The combined organic phases were concentrated under vacuum to give a brown, oily liquid, crude product L1-2. $^1$H NMR (400 MHz, CDCl$_3$) δ 5.00-4.88 (m, 1H), 3.98-3.88 (m, 4H), 3.58-3.55 (m, 2H), 3.05 (s, 3H), 2.14-1.80 (m, 6H). The crude product was used directly in the next reaction without further purification.

Step 2: Preparation of Compound L1-3

Lithium aluminum hydride (9.6 g, 253.9 mmol) was dissolved in tetrahydrofuran (200.0 mL). A solution of L1-2 (20.0 g, 84.6 mmol) in tetrahydrofuran (200.0 mL) was slowly added dropwise to the system. After the addition was completed, the temperature was raised to 70° C. and then the reaction was continued for 2 hours. After the reaction was completed, 10.0 mL of water, 10.0 mL of a 15% aqueous sodium hydroxide solution, and 30.0 mL of water were sequentially and slowly added to the reaction solution to quench the reaction. The reaction solution was stirred for ten minutes and then filtered, and the filter cake was washed with ethyl acetate. The filtrate was concentrated under vacuum to give a brown-black oily crude product L1-3 (crude product). $^1$H NMR (400 MHz, CDCl$_3$) δ 3.96-3.87 (m, 5H), 3.58-3.49 (m, 2H), 2.16-2.06 (m, 1H), 2.01-1.86 (m, 2H), 1.60-1.49 (m, 3H). The crude product was used directly in the next reaction without further purification.

Step 3: Preparation of Compound L1-4

The compound L1-3 (22.0 g, 139.1 mmol) was dissolved in dichloromethane (280.0 mL). After the mixture was cooled to 0° C., Dess-Martin periodinane (70.8 g, 166.9 mmol) was added. After a reaction was conducted at 0° C. for 1 hour, the temperature was raised to 25° C. and the reaction was continued for 16 hours. 500 mL of saturated aqueous sodium sulfite solution and 500 mL of saturated aqueous sodium bicarbonate solution were added to the system, and then the mixture was stirred for 1 hour. Solids were removed by filtration, and the aqueous phase was extracted with ethyl acetate (500 mL×3). The combined organic phases were concentrated under vacuum to give a yellow oily crude product L1-4. $^1$H NMR (400 MHz, CDCl$_3$) δ 4.03-3.90 (m, 5H), 3.57-3.54 (m, 1H), 2.62-2.47 (m, 4H), 2.21-2.14 (m, 1H), 1.87-1.79 (m, 1H). The crude product was used directly in the next reaction without further purification.

Step 4: Preparation of Compound L1-5

The compound L1-4 (17.0 g, 108.9 mmol) was dissolved in toluene (550.0 mL), and methyl cyanoacetate (16.2 g, 163.3 mmol), ammonium acetate (2.5 g, 32.7 mmol), and acetic acid (1.3 g, 21.8 mmol) were sequentially added to the system. After the temperature was raised to 120° C., the reaction was continued for 16 hours. The reaction solution was cooled to room temperature, 500 mL of toluene and 500 mL of water were added, the solution was separated into layers, and the aqueous and organic phases were separated. The aqueous phase was then extracted with ethyl acetate (500 mL×3). The combined organic phases were washed sequentially with 400 mL of a saturated sodium bicarbonate solution and 400 mL of saturated brine, dried over anhydrous sodium sulfate, and concentrated in vacuum to give a crude product. The crude product was separated and purified by silica gel column chromatography (eluent: petroleum ether/ethyl acetate=2/1) to give a yellow oily product L1-5, in which cis-configuration and trans-configuration were contained in a molar ratio of 1:1. MS m/z: 237.9 [M+1]$^+$. $^1$H NMR (400 MHz, CDCl$_3$) δ 3.99-3.40 (m, 10H), 3.10-2.71 (m, 3H), 2.14-2.07 (m, 1H), 1.89-1.83 (m, 1H).

Step 5: Preparation of Compound L1-6

A solution (2 M, 3.8 mL) of isopropyl magnesium chloride in tetrahydrofuran was slowly added dropwise to a suspension solution of 2-bromopyridine (15.8 g, 100.0 mmol) and magnesium powder (2.7 g, 110.0 mmol) in tetrahydrofuran (26.0 mL) at 25° C. under protective nitrogen. After the addition was completed, a reaction was conducted at 25° C. for 3 hours. In another reaction flask, under protective nitrogen, a mixture of the compound L1-5 (2.0 g, 8.4 mmol) and cuprous iodide (481.6 mg, 2.5 mmol) in tetrahydrofuran (20.0 mL) was cooled to a temperature of −78° C., and the freshly prepared Grignard reagent described above was slowly added dropwise. After the dropwise addition was completed, the temperature was raised to 0° C., and a reaction was conducted for three hours. After the temperature was raised to 25° C., the reaction was continued for 16 hours. Then, 100 mL of a saturated ammonium chloride solution and 100 mL of ethyl acetate were added to the reaction solution, and the organic and aqueous phases were separated. The aqueous phase was extracted with ethyl acetate (100 mL×3). The combined organic phases were washed with 100 mL of saturated brine, dried over anhydrous sodium sulfate, and concentrated in vacuum to give a crude product. The crude product was separated and purified by silica gel column chromatography (eluent: petroleum ether/ethyl acetate=3/5) to give a yellow oily product L1-6. MS m/z: 317.0 [M+1]$^+$. $^1$H NMR (400 MHz, CDCl$_3$) δ 8.66-8.60 (m, 1H), 7.77-7.73 (m, 1H), 7.45-7.30 (m, 1H), 7.26-7.24 (m, 1H), 3.97-3.63 (m, 9H), 3.07-2.80 (m, 1H), 2.70-2.60 (m, 1H), 2.40-1.95 (m, 4H), 1.35-0.85 (m, 1H).

Step 6: Preparation of Compound L1-7

The compound L1-6 (580.0 mg, 1.8 mmol) was dissolved in ethylene glycol (25.0 mL), and potassium hydroxide (102.9 mg, 1.8 mmol) was added. After the temperature was raised to 120° C., a reaction was conducted for 12 hours. The reaction solution was cooled to room temperature, and then 25 mL of water was added to the reaction solution, and the aqueous phase was extracted with ethyl acetate (20 mL×4). The combined organic phases were concentrated under vacuum to give a crude product. The crude product was separated and purified by column chromatography (eluent: petroleum ether/ethyl acetate=2/3) to give a yellow oily product L1-7. MS m/z: 258.9 [M+1]$^+$. $^1$H NMR (400 MHz, CDCl$_3$) δ 8.57-8.54 (m, 1H), 7.69-7.66 (m, 1H), 7.36-7.33 (m, 1H), 7.18-7.16 (m, 1H), 3.81-3.75 (m, 4.5H), 3.49 (d, J=9.2 Hz, 0.5H), 3.20 (d, J=10.0 Hz, 0.5H), 2.78 (d, J=10.0 Hz, 0.5H), 2.70-2.47 (m, 4H), 2.00-1.78 (m, 3H), 1.45-1.37 (m, 0.5H), 1.22-1.10 (m, 0.5H).

Step 7: Preparation of Compound L1

Lithium aluminum hydride (104.3 mg, 2.8 mmol) was suspended in tetrahydrofuran (4.0 mL) at 25° C., and a solution (4.0 mL) of L1-7 (355.0 mg, 1.4 mmol) in tetrahydrofuran was slowly added. After the addition was completed, a reaction was conducted for 16 hours. To the reaction solution, 0.1 ml of water, 0.1 ml of sodium hydroxide at 15% concentration, and 0.3 ml of water were sequentially added to quench the reaction, the mixture was stirred for 10 minutes and then filtered, and the filter cake was washed with 30 mL of ethyl acetate. The resulting filtrate was concentrated under vacuum to give a yellow oily crude product L1. $^1$H NMR (400 MHz, CDCl$_3$) δ 8.60-8.57 (m, 1H), 7.68-7.63 (m, 1H), 7.33-7.29 (m, 1H), 7.16-7.13 (m, 1H), 3.89-3.72 (m, 4.5H), 3.55 (d, J=9.2 Hz, 0.5H), 3.17 (d, J=10.0 Hz, 0.5H), 2.84 (d, J=10.0 Hz, 0.5H), 2.59-1.50 (m, 9H), 1.87-1.73 (m, 0.5H), 1.19-1.11 (m, 0.5H).

Reference Example 2: Synthesis of Hydrochloride Salt of Chiral Intermediate (+)-L1

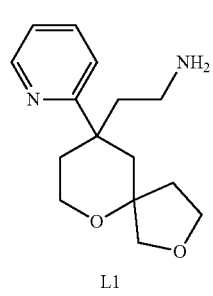

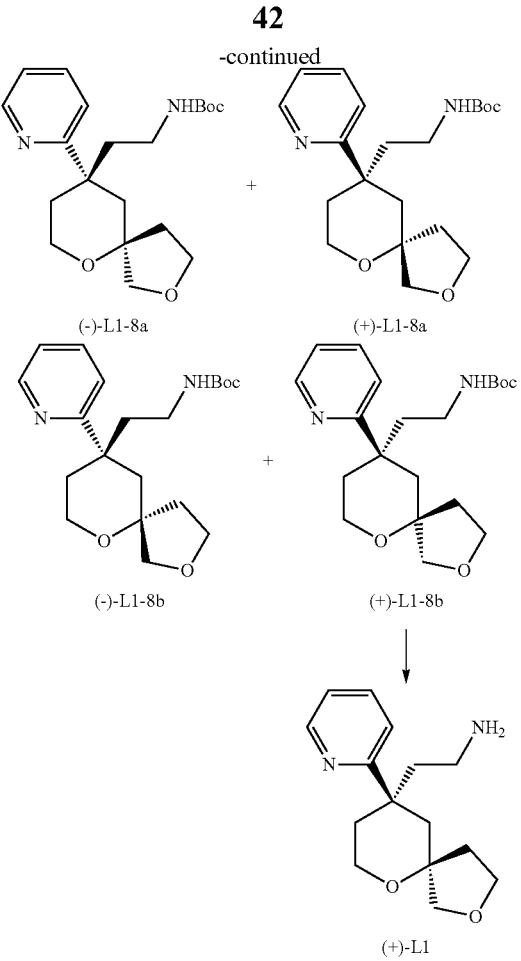

Step 1: Preparation of Compound L1-8

The compound L1 (1.5 g, 5.6 mmol) was dissolved in a dichloromethane solution (30.0 mL) at 25° C., and Boc$_2$O (1.5 g, 6.8 mmol) and triethylamine (1.1 g, 11.3 mmol) were added to the system to react therewith for 10 hours. The reaction solution was concentrated in vacuum, and the residue was separated and purified by silica gel column chromatography (eluent: petroleum ether/ethyl acetate=1:1) to give a pale-yellow oily liquid L1-8. $^1$H NMR (400 MHz, CDCl$_3$) δ 8.64-8.55 (m, 1H), 7.73-7.61 (m, 1H), 7.36-7.29 (m, 1H), 7.21-7.10 (m, 1H), 4.25 (br s, 1H), 3.92-3.67 (m, 4.5H), 3.55 (d, J=9.4 Hz, 0.5H), 3.17 (dd, J=0.9, 10.0 Hz, 0.5H), 3.05-2.80 (m, 1H), 2.84 (d, J=10.0 Hz, 0.5H), 2.70-2.42 (m, 3H), 2.12-1.62 (m, 5H), 1.39 (s, 9H), 1.20-1.07 (m, 0.5H), 0.98-0.86 (m, 0.5H).

Step 2: SFC Resolution of Compound L1-8

The compound L1-8 (1.8 g, 4.5 mmol) was a racemate and was separated twice by SFC (Separation Conditions for the First Time: Column: OJ (250 mm*30 mm, 5 μm); Mobile Phase: A: CO$_2$; B: [0.1% NH$_3$H$_2$O EtOH]; B %: 15%; the Second Time: Column: AD (250 mm*30 mm, 10 μm); Mobile Phase: A: CO$_2$; B: [0.1% NH$_3$H$_2$O EtOH]; B %: 30%) to give four diastereomers, i.e., compound (−)-L1-8a (100.0% de), compound (+)-L1-8a (100.0% de), compound (−)-L1-8b (86.0% de), and (+)-L1-8b (98.0% de):

(−)-L1-8a (270.0 mg), MS m/z=363.3 [M+1]+. SFC: Column: Chiralcel OJ-3 (100 mm*4.6 mm, 3 μm); Mobile Phase: A: CO2; B: [0.05% DEA EtOH]; B %: 5%-40%; Rt=1.184 min; 100% de.

(+)-L1-8a (250.0 mg), MS m/z=363.3 [M+1]+. SFC: Column: Chiralcel OJ-3 (100 mm*4.6 mm, 3 μm); Mobile Phase: A: CO2; B: [0.05% DEA EtOH]; B %: 5%-40%; Rt=1.262 min; 100% de.

(−)-L1-8b (300.0 mg), MS m/z=363.3 [M+1]+. SFC: Column: Chiralcel OJ-3 (100 mm*4.6 mm, 3 μm); Mobile Phase: A: CO2; B: [0.05% DEA EtOH]; B %: 5%-40%; Rt=1.361 min; 86% de.

(+)-L1-8b (360.0 mg), MS m/z=363.3 [M+1]+. SFC: Column: Chiralcel OJ-3 (100 mm*4.6 mm, 3 μm); Mobile Phase: A: CO2; B: [0.05% DEA EtOH]; B %: 5%-40%; Rt=1.523 min; 98.0% de.

Step 3: Preparation of Hydrochloride Salt of Compound (+)-L1

The compound (+)-L1-8b (80.0 mg, 199.9 μmol) was dissolved in dioxane (3.0 mL) at 25° C., and a hydrochloric acid/dioxane solution (4 M, 3.0 mL) was added to react therewith for 1 hour. The reaction solution was concentrated in vacuum to give a hydrochloride salt (130 mg) of (+)-L1. MS m/z=363.3 [M+1]+. The crude product was used directly in the next reaction without further purification.

Reference Example 3: Synthesis of Chiral Intermediate (+)-L1

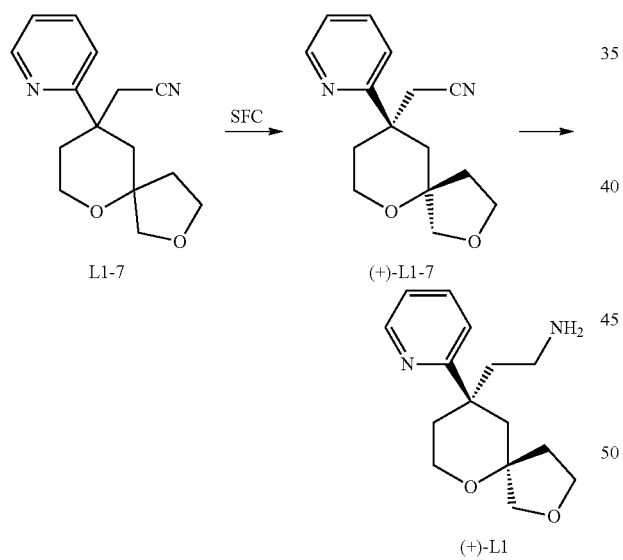

Step 1: SFC Separation of Compound L1-7

L1-7 (5.8 g, 22.6 mmol) was separated by SFC (Column: Chiralpak AD-H 250*30 mm, 5 μm; Mobile Phase: A: CO2; B: [EtOH]; B %: 40%) to give (+)-L1-7. 1H NMR (400 MHz, CDCl3) δ 8.57 (dd, J=0.8, 4.8 Hz, 1H), 7.70-7.64 (m, 1H), 7.39-7.32 (m, 1H), 7.18-7.13 (m, 1H), 3.89-3.58 (m, 5H), 3.53-3.45 (m, 1H), 2.73-2.54 (m, 2H), 2.51-2.42 (m, 2H), 1.90-1.85 (d, J=13.6 Hz, 2H), 1.37-1.28 (m, 1H), 1.10-1.00 (m, 1H). SFC: Column: Chiralpak IC-3 (150 mm*4.6 mm, 3 μm); Mobile Phase: A: CO2; B: [0.05% Isopropylamine EtOH]; B %: 5%-40%; Rt=3.399 min; 100.0% de. Optical Rotation: $[\alpha]_D^{25}$=+29.0 (C=0.4, MeOH).

Step 2: Preparation of Compound (+)-L1

The compound (+)-L1-7 (450.0 mg, 1.7 mmol) was dissolved in ethanol (6.0 mL), and Raney nickel (89.6 mg, 522.6 μmol, purity: 50%) and aqueous ammonia (1.85 mL, concentration: 27%) were added, air was replaced with hydrogen three times, and the mixture was reacted in a hydrogen atmosphere (15 Psi) at 25° C. for 2 hours. The reaction solution was filtered, and the filtrate was concentrated in vacuum to give (+)-L1. MS m/z: 263.2 [M+1]+. 1H NMR (400 MHz, CDCl3) δ 8.63-8.56 (m, 1H), 7.71-7.61 (m, 1H), 7.36-7.29 (m, 1H), 7.19-7.12 (m, 1H), 3.89-3.81 (m, 3H), 3.76-3.73 (m, 2H), 3.58-3.50 (m, 1H), 2.61-2.51 (m, 1H), 2.46-2.40 (m, 2H), 2.23-2.10 (m, 1H), 1.96-1.87 (m, 2H), 1.80-1.73 (m, 1H), 1.71-1.64 (m, 1H), 1.45-1.41 (m, 1H), 1.20-1.08 (m, 1H). The crude product was used directly in the next reaction without further purification.

Reference Example 4: Synthesis of Chiral Intermediate (+)-L2

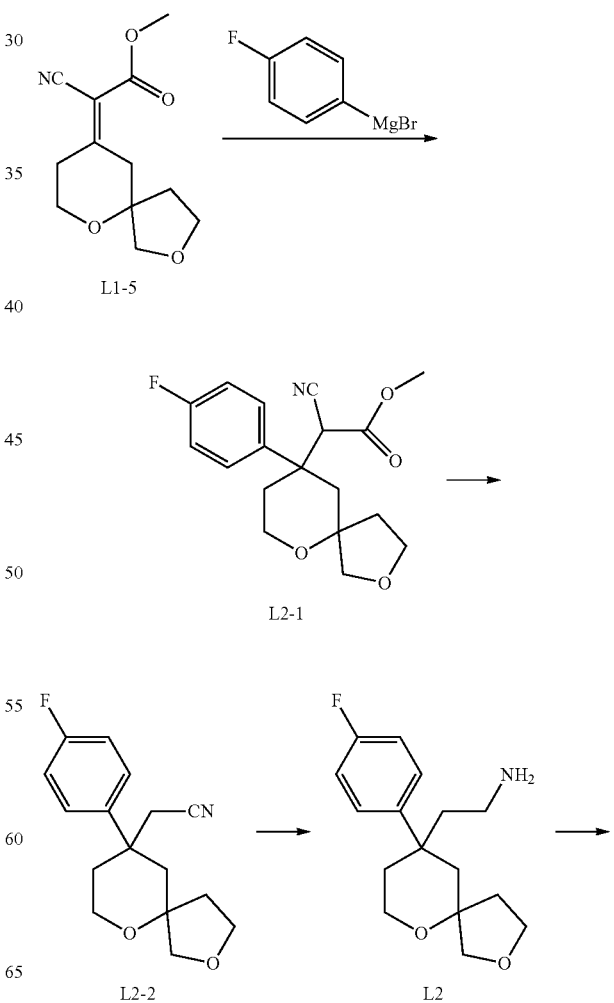

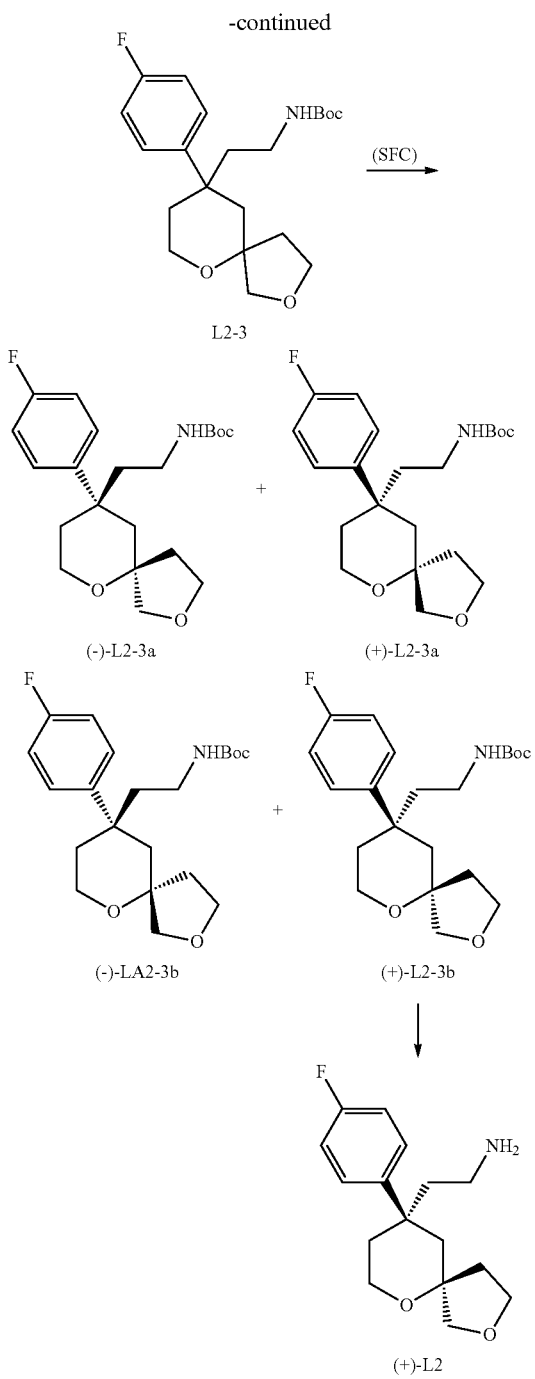

Step 1: Preparation of Compound L2-1

Under protective nitrogen, 4-fluorophenyl magnesium bromide (2 M, 15.81 mL, 31.6 mmol) was dissolved in tetrahydrofuran (50.0 mL), to which cuprous iodide (240.8 mg, 1.3 mmol) was added, and then the temperature was lowered to 0° C., and a solution of the compound L1-5 (3.0 g, 12.6 mmol) in tetrahydrofuran (30.0 mL) was added to the reaction system and stirred for 10 minutes. The temperature was raised to 25° C., and the mixture was stirred for 3 hours. The reaction solution was quenched with 80.0 ml of a saturated ammonium chloride solution added thereto, diluted with 30.0 ml of water added thereto, and extracted with ethyl acetate (100 ml×3). The combined organic phases were washed with saturated brine (80 ml×2), dried over anhydrous sodium sulfate, and concentrated in vacuum. The concentrate was separated and purified by silica gel column chromatography (eluent: petroleum ether/ethyl acetate=2/1) to give a pale-yellow oily liquid L2-1. MS m/z: 334.2 $[M+1]^+$. $^1$H NMR (400 MHz, CDCl$_3$) δ 7.48-7.29 (m, 2H), 7.17-7.06 (m, 2H), 3.96-3.51 (m, 9H), 3.19 (d, J=10.0 Hz, 0.5H), 2.94 (dd, J=10.2, 18.2 Hz, 0.5H), 2.77-2.28 (m, 3H), 2.24-1.93 (m, 2H), 1.41-1.47 (m, 0.5H), 1.41-1.47 (m, 0.5H), 1.10-0.95 (m, 0.5H).

Step 2: Preparation of Compound L2-2

The compound L2-1 (3.3 g, 9.9 mmol) was dissolved in an ethylene glycol (40.0 mL) solution, potassium hydroxide (833.1 mg, 14.9 mmol) was added to the system, and the mixture was warmed to 120° C. and reacted for 3 hours. 40 mL of water was added to the reaction solution, the system was extracted with ethyl acetate (70 ml×3), and the obtained organic phases were combined, washed with saturated brine (60 ml×2), dried over anhydrous sodium sulfate, and concentrated in vacuum to give a crude product. The crude product was separated and purified by silica gel column chromatography (eluent: petroleum ether/ethyl acetate=1/1) to give a pale-yellow oily liquid L2-2. MS m/z: 276.2 $[M+1]^+$. $^1$H NMR (400 MHz, CDCl$_3$) δ 7.43-7.33 (m, 2H), 7.17-7.08 (m, 2H), 3.95-3.73 (m, 4.5H), 3.60 (d, J=9.4 Hz, 0.5H), 3.31 (d, J=10.0 Hz, 0.5H), 2.97 (d, J=10.2 Hz, 0.5H), 2.68-2.28 (m, 4H), 2.23-1.87 (m, 3H), 1.59-1.50 (m, 0.5H), 0.98-0.86 (m, 0.5H).

Step 3: Preparation of Compound L2

The compound L2-2 (2.5 g, 9.1 mmol) was dissolved in tetrahydrofuran (30.0 mL), lithium aluminum hydride (689.3 mg, 18.2 mmol) was added at 0° C., and the mixture was reacted at 25° C. for 3 hours. 0.7 ml of water, 0.7 ml of a 15% aqueous sodium hydroxide solution, and 2.1 ml of water were slowly and sequentially added to the reaction solution to quench the reaction. The mixture was stirred for fifteen minutes and then filtered, and the filtrate was dried over anhydrous sodium sulfate and concentrated in vacuum to give a pale-yellow oily liquid L2 (crude product), where MS m/z: 280.0 [M+1]. The crude product was used directly in the next reaction without further purification.

Step 4: Preparation of Compound L2-3

The compound L2 (2.3 g, 8.2 mmol) was dissolved in dichloromethane (30.0 mL), Boc$_2$O (2.3 g, 10.7 mmol) and triethylamine (1.7 g, 16.5 mmol) were sequentially added, and then the mixture was reacted at 25° C. for 12 hours. The reaction solution was concentrated in vacuum, and the concentrate was separated and purified by silica gel column chromatography (eluent: petroleum ether/ethyl acetate=1/1) to give a crude product. The crude product was separated and purified by preparative high-performance liquid chromatography (Column: Phenomenex Gemini C18 250*50 mm, 10 μm; Mobile Phase: [water (0.05% ammonium hydroxide v/v)-acetonitrile]; B %: 40%-65%) to give a pale-yellow oily liquid L2-3. MS m/z: 402.3 $[M+23]^+$. $^1$H NMR (400 MHz, CDCl$_3$) δ 7.19-7.13 (m, 2H), 7.01-6.92 (m, 2H), 4.11 (br s, 1H), 3.84-3.61 (m, 4.5H), 3.51-3.39 (m, 0.5H), 3.21 (d, J=10.0 Hz, 0.5H), 2.93-2.79 (m, 1H), 2.80 (d, J=10.4 Hz, 0.5H), 2.58-2.44 (m, 1H), 2.25-2.18 (m, 1H), 2.11-1.58 (m, 6H), 1.51-1.41 (m, 0.5H), 1.32 (s, 9H), 1.21-1.10 (m, 0.5H).

Step 5: SFC Resolution of Compound L2-3

The compound L2-3 (1.05 g, 2.77 mmol) was resolved by SFC (Column: OJ (250 mm*30 mm, 5 μm); Mobile Phase: A: $CO_2$; B: [0.1% $NH_3H_2O$ EtOH]; B %: 30%) to give four diastereomers, i.e., compound (−)-L2-3a (86.0% de), compound (+)-L2-3a (97.3% de), compound (−)-L2-3b (87.8% de), and compound (+)-L2-3b (96.4% de):

(−)-L2-3a (210.0 mg), MS m/z=402.3 $[M+23]^+$. SFC: Column: Chiralcel OJ-3 (100 mm*4.6 mm, 3 μm); Mobile Phase: A: $CO_2$; B: [0.05% DEA EtOH]; B %: 5%-40%; Rt=1.362 min; 86% de.

(+)-L2-3a (280.0 mg), MS m/z=402.3 $[M+23]^+$. SFC: Column: Chiralcel OJ-3 (100 mm*4.6 mm, 3 μm); Mobile Phase: A: $CO_{O2}$; B: [0.05% DEA EtOH]; B %: 5%-40%; Rt=1.491 min; 97.3% de.

(−)-L2-3b (200.0 mg), MS m/z=402.3 $[M+23]^+$. SFC: Column: Chiralcel OJ-3 (100 mm*4.6 mm, 3 μm); Mobile Phase: A: $CO_{O2}$; B: [0.05% DEA EtOH]; B %: 5%-40%; Rt=1.589 min; 87.8% de.

(+)-L2-3b (190.0 mg), MS m/z=402.3 $[M+23]^+$. SFC: Column: Chiralcel OJ-3 (100 mm*4.6 mm, 3 μm); Mobile Phase: A: $CO_{O2}$; B: [0.05% DEA EtOH]; B %: 5%-40%; Rt=1.799 min; 96.4% de.

Step 6: Preparation of Hydrochloride Salt of Chiral Compound (+)-L2

The compound (+)-L2-3b (190.0 mg, 488.0 μmol) was dissolved in dioxane (3.0 mL) at 25° C., and a hydrochloric acid/dioxane solution (4 M, 3 mL) was added and reacted therewith for 0.5 hours. Then, the reaction solution was concentrated in vacuum to give a hydrochloride salt (340.0 mg) of (+)-L2. MS m/z: 280.0 $[M+1]^+$.

Reference Example 5: Synthesis of Chiral Intermediate (+)-L3

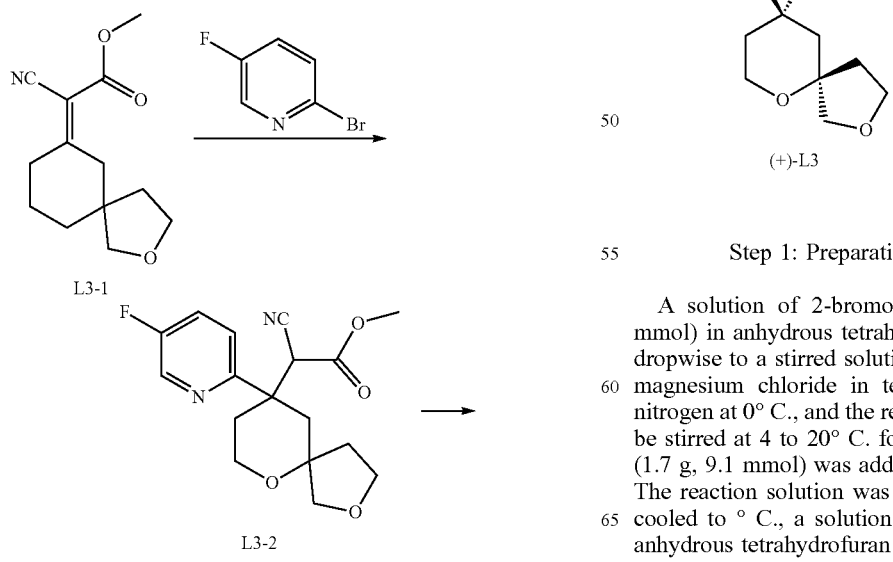

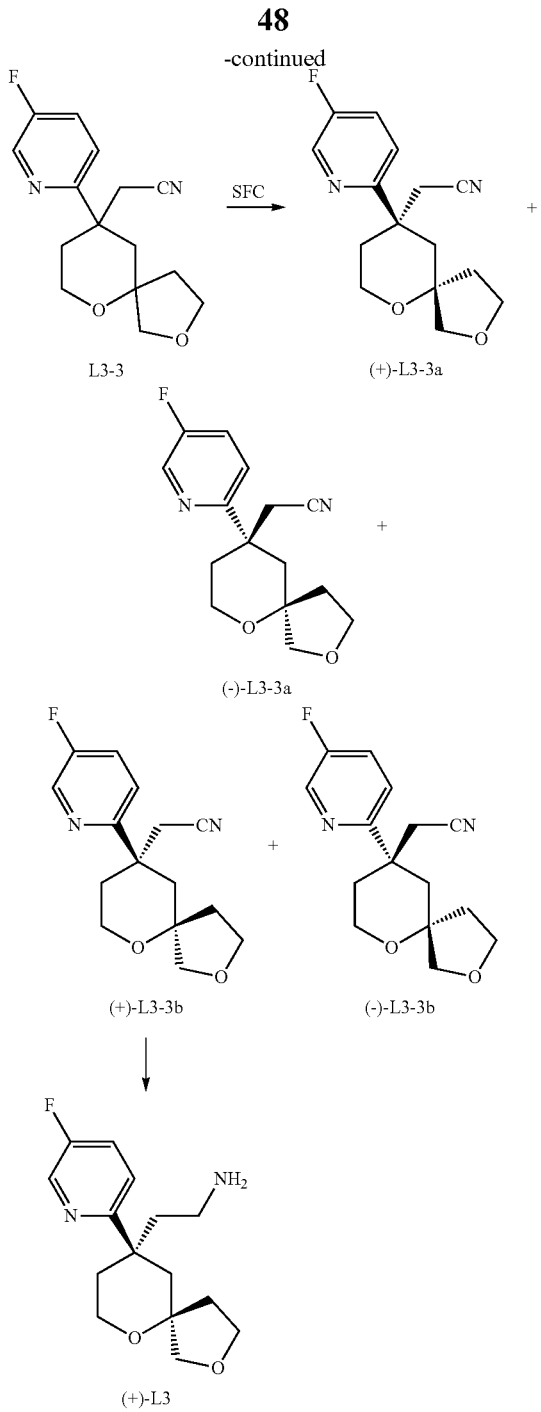

Step 1: Preparation of Compound L3-2

A solution of 2-bromo-5-fluoropyridine (16.0 g, 91.0 mmol) in anhydrous tetrahydrofuran (64.0 mL) was added dropwise to a stirred solution (2 M, 45.5 mL) of isopropyl magnesium chloride in tetrahydrofuran under protective nitrogen at 0° C., and the reaction solution was continued to be stirred at 4 to 20° C. for 3 hours. Then, cuprous iodide (1.7 g, 9.1 mmol) was added to the above reaction system. The reaction solution was stirred for 20 minutes and then cooled to ° C., a solution of L3-1 (7.2 g, 30.4 mmol) in anhydrous tetrahydrofuran (30.0 mL) was added dropwise, and the reaction solution was warmed to 30° C. and then continued to be stirred for 16 hours. After the reaction was completed, the reaction solution was poured into 80 mL of a cold saturated aqueous ammonium chloride solution, and extracted with ethyl acetate (90 mL×3). The combined organic phases were dried over anhydrous sodium sulfate and concentrated in vacuum. The concentrate was separated and purified by silica gel column chromatography (eluent: petroleum ether/ethyl acetate=9/1 to 1/1) to give a brown-black oily liquid L3-2. MS m/z: 335.1 [M+1]$^+$. $^1$H NMR (400 MHz, CDCl$_3$) δ 8.48-8.30 (m, 1H), 7.52-7.27 (m, 2H), 3.92-3.45 (m, 9H), 3.06-2.94 (m, 0.5H), 2.80-2.46 (m, 2.5H), 2.34-2.01 (m, 2H), 1.97-1.79 (m, 1H), 1.28-1.20 (m, 0.5H), 1.10-0.79 (m, 0.5H).

Compound L4-2 was synthesized with reference to the route of synthesis of L3-2:

| Compound Number | Structural Formula | Spectrum |
|---|---|---|
| L4-2 | 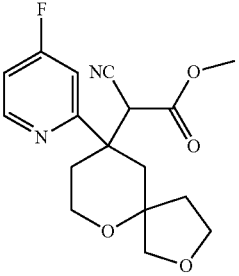 [SMILES: COC(=O)C(C#N)C1(c2cc(F)ccn2)CCOC2(CCOC2)C1] | $^1$H NMR (400 MHz, CDCl$_3$) δ 8.65-8.36 (m, 1H), 7.17-6.84 (m, 2H), 3.96-3.43 (m, 9H), 3.10-3.00 (m, 0.5H), 2.82-2.61 (m, 1.5H), 2.56-1.76 (m, 4H), 1.33-1.21 (m, 0.5H), 1.10-0.83 (m, 0.5H). MS m/z: 335.1[M + 1]$^+$. |

Step 2: Preparation of Compound L3-3

The compound L3-2 (3.7 g, 11.1 mmol) was dissolved in ethylene glycol (70.0 mL), potassium hydroxide (1.2 g, 22.1 mmol) was added, the reaction solution was heated to 120° C., and stirring was continued for 5 hours. The reaction solution was cooled to room temperature, and then poured into 60.0 mL of water and extracted with ethyl acetate (40.0 mL×3). The combined organic phases were washed once with 30.0 mL of saturated brine, dried over anhydrous sodium sulfate, and concentrated in vacuum to give a yellow crude product. The crude product was separated and purified by silica gel column chromatography (eluent: petroleum ether/ethyl acetate=9/1 to 1/1) to give a pale-yellow oily liquid L3-3. MS m/z=277.0 [M+1]$^+$. $^1$H NMR (400 MHz, CDCl$_3$) δ 8.52-8.47 (m, 1H), 7.56-7.35 (m, 2H), 3.95-3.79 (m, 5H), 3.63-3.52 (m, 1H), 3.25 (d, J=10.0 Hz, 0.5H), 2.88 (d, J=10.0 Hz, 0.5H), 2.80-2.70 (m, 1H), 2.67-2.41 (m, 3H), 2.04-1.85 (m, 3H), 1.47-1.40 (m, 0.5H), 1.21-1.10 (m, 0.5H).

Step 3: SFC Separation of Compound L3-3

L3-3 (850.0 mg) was a racemate and was separated twice by SFC (First Time: Column: C$_2$ (250 mm*50 mm, 10 μm); Mobile Phase: A: CO$_2$; B: [0.1% NH$_3$H$_2$O MeOH]; B %: 30%; Second Time: Column: AY (250 mm*30 mm, 10 μm); Mobile Phase: A: CO$_2$; B: [0.1% NH$_3$H$_2$O EtOH]; B %: 25%) to give four diastereomers, i.e., compound (+)-L3-3a (100.0% de), compound (−)-L3-3a (97.4% de), compound (+)-L3-3b (90.7% de), and compound (−)-L3-3b (100.0% de):

(+)-L3-3a (250.0 mg), MS m/z=277.2 [M+1]$^+$. SFC: Column: Lux Cellulose-2 (150 mm*4.6 mm, 3 μm); Mobile Phase: A: CO$_2$; B: [0.05% DEA MeOH]; B %: 5%-40% 5.5 min, 40% 3.0 min, 5% 1.5 min; Rt=3.545 min, 100.0% de. Optical Rotation: [α]$_D^{25}$=+18.5 (C=1, MeOH).

(−)-L3-3a (160.0 mg), MS m/z=277.2 [M+1]$^+$. SFC: Column: Lux Cellulose-2 (150 mm*4.6 mm, 3 μm); Mobile Phase: A: CO$_2$; B: [0.05% DEA MeOH]; B %: 5%-40% 5.5 min, 40% 3.0 min, 5% 1.5 min; Rt=4.198 min, 97.4% de. Optical Rotation: [α]$_D^{25}$=−19.6 (C=1, MeOH).

(+)-L3-3b (150.0 mg), MS m/z=277.2 [M+1]$^+$. $^1$H NMR (400 MHz, CDCl$_3$) δ 8.51 (d, J=2.8 Hz, 1H), 7.64-7.35 (m, 2H), 3.99-3.69 (m, 5H), 3.59 (d, J=9.6 Hz, 1H), 2.84-2.70 (m, 1H), 2.68-2.45 (m, 3H), 2.03-1.89 (m, 2H), 1.47-1.40 (m, 1H), 1.21-1.10 (m, 1H). SFC: Column: Lux Cellulose-2 (150 mm*4.6 mm, 3 μm); Mobile Phase: A: CO$_2$; B: [0.05% DEA MeOH]; B %: 5%-40% 5.5 min, 40% 3.0 min, 5% 1.5 min; Rt=4.599 min; 90.7% de. Optical Rotation: [α]$_D^{25}$=+22.4 (C=1, MeOH).

(−)-L3-3b (120.0 mg), MS m/z=277.2 [M+1]$^+$. SFC: Column: Lux Cellulose-2 (150 mm*4.6 mm, 3 μm); Mobile Phase: A: CO$_2$; B: [0.05% DEA MeOH]; B %: 5%-40% 5.5 min, 40% 3.0 min, 5% 1.5 min; Rt=4.781 min; 100.0% de. Optical Rotation: [α]$_D^{25}$=−22.0 (C=1, MeOH).

Step 4: Preparation of Compound (+)-L3

(+)-L3-3b (150.0 mg, 542.9 μmol) was dissolved in ethanol (20.0 mL), aqueous ammonia (0.66 mL, purity: 28%) and Raney nickel (0.1 g, purity: 50%) were added, air was replaced with hydrogen three times, and the mixture was reacted at 30° C. for 16 hours in a hydrogen atmosphere (15 Psi). The reaction solution was filtered, and the filtrate was concentrated in vacuum to give (+)-L3 (crude product). MS m/z=281.0 [M+1]$^+$. $^1$H NMR (400 MHz, CDCl$_3$) δ 8.37 (d, J=2.4 Hz, 1H), 7.40-7.21 (m, 2H), 3.86-3.58 (m, 5H), 3.52-3.42 (m, 1H), 2.47 (dt, J=5.2, 11.6 Hz, 1H), 2.39-2.24 (m, 2H), 2.09 (dt, J=5.0, 11.6 Hz, 1H), 1.85-1.54 (m, 4H), 1.39-1.27 (m, 1H), 1.11-0.99 (m, 1H).

Reference Example 6: Synthesis of Chiral Intermediate (+)-L4

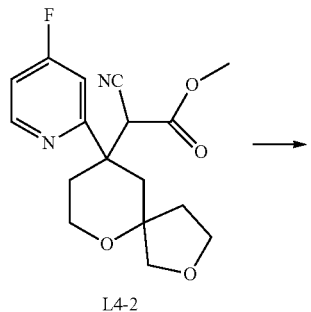

L4-2

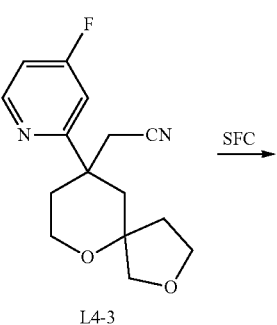

L4-3

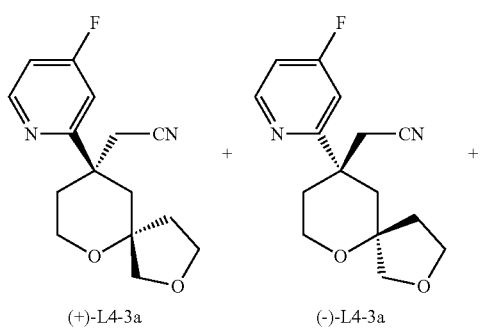

(+)-L4-3a     (−)-L4-3a

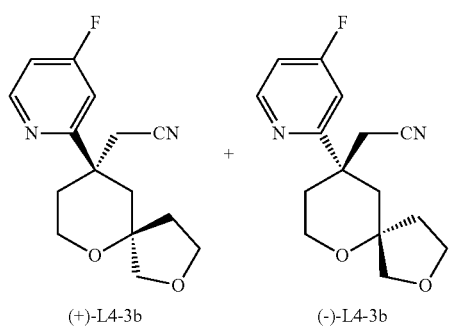

(+)-L4-3b     (−)-L4-3b

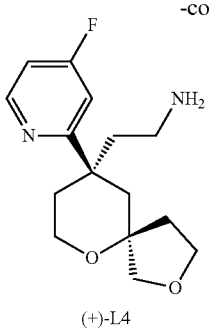

(+)-L4

Step 1: Preparation of Compound L4-3

The compound L4-2 (2.2 g, 6.6 mmol) was dissolved in dimethyl sulfoxide (40.0 mL), water (0.4 mL) and sodium chloride (115.4 mg, 2.0 mmol) were added and heated to 160° C., and stirring was continued for 1 hour. After being cooled to room temperature, the reaction solution was poured into 80 mL of water, and extracted with ethyl acetate (50 mL×3). The organic phases were combined, washed with 40 mL of saturated brine, dried over anhydrous sodium sulfate, filtered, and concentrated in vacuum to remove the organic solvent to give a yellow crude product. The crude product was separated and purified by silica gel column chromatography (eluent: petroleum ether/ethyl acetate=1/10 to 45/100) to give L4-3. MS m/z=277.0 [M+1]$^+$.

Step 2: SFC Separation of Compound L4-3

L4-3 (1.4 g, 5.1 mmol) was separated by SFC (Column: $C_2$ (250 mm*50 mm, 10 μm); Mobile Phase: A: $CO_{02}$; B: [0.1% $NH_3H_2O$ EtOH]; B %: 25%) to give four diastereomers, i.e., compound (+)-L4-3a (99.4% de), compound (−)-L4-3a (97.1% de), compound (+)-L4-3b (97.4% de), and compound (−)-L4-3b (96.6% de):

(+)-L4-3a (350.0 mg), MS m/z=277.2 [M+1]$^+$. SFC: Column: Lux Cellulose-2 (150 mm*4.6 mm, 3 μm); Mobile Phase: A: $CO_{02}$; B: [0.05% DEA EtOH]; B %: 5%-40% 5.5 min, 40% 3.0 min, 5% 1.5 min; Rt=3.203 min, 99.4% de. $[\alpha]D^{25}$=+32.0 (C=1, MeOH).

(−)-L4-3a (250.0 mg), MS m/z=277.2 [M+1]$^+$. SFC: Column: Lux Cellulose-2 (150 mm*4.6 mm, 3 μm); Mobile Phase: A: $CO_{02}$; B: [0.05% DEA EtOH]; B %: 5%-40% 5.5 min, 40% 3.0 min, 5% 1.5 min; Rt=3.690 min, 97.1% de. $[\alpha]D^{25}$=−22.5 (C=1, MeOH).

(+)-L4-3b (250.0 mg), MS m/z=277.2 [M+1]$^+$. $^1$H NMR (400 MHz, CDCl$_3$) δ 8.54 (dd, J=5.6, 8.8 Hz, 1H), 7.08 (dd, J=2.4, 10.0 Hz, 1H), 6.96-6.89 (m, 1H), 3.93-3.58 (m, 5H), 3.49 (d, J=9.2 Hz, 1H), 2.68 (d, J=16.6 Hz, 1H), 2.60-2.33 (m, 3H), 1.96-1.84 (m, 2H), 1.45-1.36 (m, 1H), 1.14-1.04 (m, 1H). SFC: Column: Lux Cellulose-2 (150 mm*4.6 mm, 3 μm); Mobile Phase: A: $CO_{02}$; B: [0.05% DEA EtOH]; B %: 5%-40% 5.5 min, 40% 3.0 min, 5% 1.5 min; Rt=4.074 min, 97.4% de. $[\alpha]D^{25}$=+30.2 (C=1, MeOH).

(−)-L4-3b (360.0 mg), MS m/z=277.2 [M+1]$^+$. SFC: Column: Lux Cellulose-2 (150 mm*4.6 mm, 3 μm); Mobile Phase: A: $CO_{02}$; B: [0.05% DEA EtOH]; B %: 5%-40% 5.5 min, 40% 3.0 min, 5% 1.5 min; Rt=4.455 min, 96.6% de. $[\alpha]D^{25}$=−17.9 (C=1, MeOH).

Step 3: Preparation of Compound (+)-L4

(+)-L4-3b (250.0 mg, 904.8 μmol) was dissolved in ethanol (20.0 mL), aqueous ammonia (1.10 mL, purity:

28%) and Raney nickel (0.3 g, purity: 50%) were added, air was replaced with hydrogen three times, and the mixture was reacted at 30° C. for 16 hours in a hydrogen atmosphere (15 Psi). The reaction solution was filtered, and the filtrate was concentrated in vacuum to give (+)-L4 (250 mg, crude product). MS m/z=281.1 [M+1]$^+$. $^1$H NMR (400 MHz, CDCl$_3$) δ=8.61-8.36 (m, 1H), 7.01-6.75 (m, 2H), 3.84-3.58 (m, 5H), 3.48 (d, J=9.3 Hz, 1H), 2.53-2.24 (m, 3H), 2.17-2.03 (m, 1H), 1.91-1.54 (m, 4H), 1.41-1.34 (m, 1H), 1.27-1.04 (m, 1H).

Reference Example 7: Synthesis of Chiral Intermediate (+)-L5b

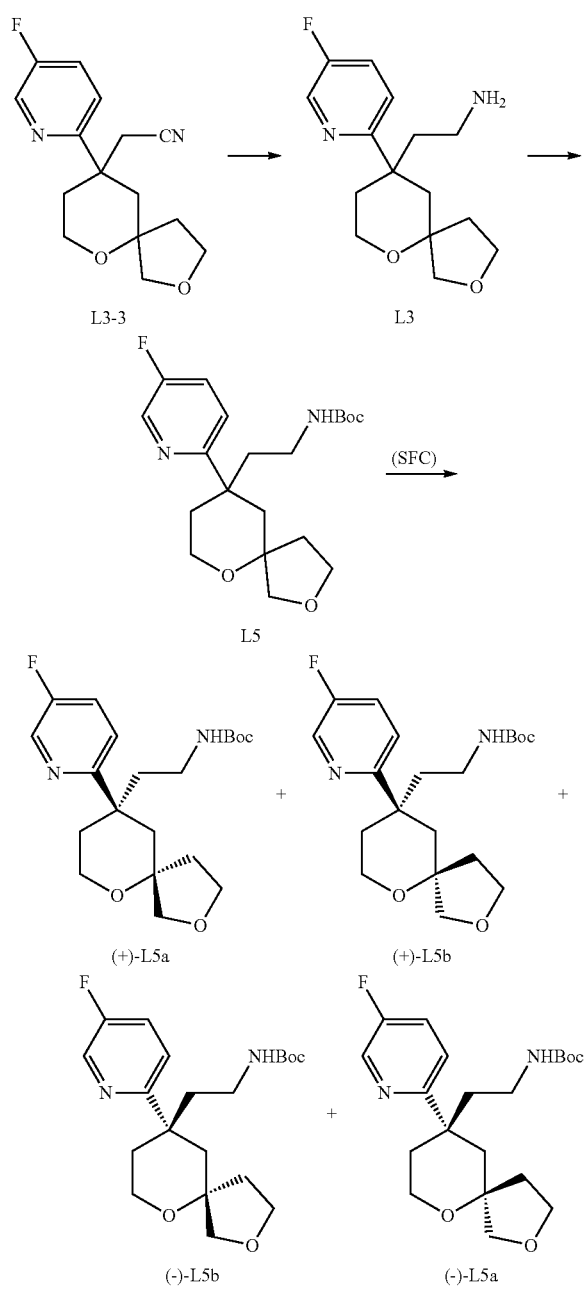

Step 1: Preparation of Compound L3

The compound L3-3 (1.8 g, 6.5 mmol) was dissolved in ethanol (60.0 mL), and aqueous ammonia (2.0 mL, 14.5 mmol, purity: 28%) and Raney nickel (1.2 g, purity: 50%) were added. Stirring was continued at 30° C. for 16 hours under a hydrogen atmosphere (15 psi). The reaction solution was filtered, and the filtrate was concentrated in vacuum to give L3 (crude product), where MS m/z: 281.1 [M+1]$^+$. The crude product was used directly in the next reaction without further purification.

Step 2: Preparation of Compound L5

L3 (1.8 g, 6.42 mmol), triethylamine (325 mg, 3.2 mmol), and Boc$_2$O (1.68 g, 7.71 mmol) were added as raw materials to dichloromethane (50.0 mL) acting as a solvent. The reaction of the reaction solution was continued at 25° C. for 16 hours. The reaction solution was poured into 50 mL of water, and the aqueous phase was extracted with dichloromethane (40 mL×3). The organic phases were combined and washed once with each of 20 mL of water and 20 mL of saturated saline, and dried over anhydrous sodium sulfate. The organic solvent was removed by filtration to give a crude product. The crude product was separated and purified by silica gel column chromatography (eluent: petroleum ether/ethyl acetate=1/20 to 1/2) to give L5. MS m/z: 381.2 [M+1]$^+$.

Step 3: SFC Resolution of Compound L5

The compound L5 (1.8 g, 4.7 mmol) was resolved by SFC (column: DAICEL CHIRALPAK AD (250 mm*50 mm, 10 μm); Mobile Phase: A: CO$_2$; B: [0.1% NH$_3$H$_2$O EtOH]; B %: 30%) to give four diastereomers, i.e., compound (+)-L5a (99.6% de), compound (+)-L5b (93.2% de), compound (−)-L5b (94.6% de), and compound (−)-L5a (98.5% de):

(+)-L5a (309 mg), MS m/z=381.2 [M+1]$^+$. SFC: Column: CHIRALPAK AD (100 mm*4.6 mm, 3 μm); Mobile Phase: A: CO$_2$; B: [0.05% DEA EtOH]; B %: 5%-40% 5.0 min, 40% 2.5 min, 5% 2.5 min; Rt=3.121 min; 99.6% de.

(+)-L5b (315 mg), MS m/z=381.2 [M+1]$^+$. $^1$H NMR (400 MHz, CDCl$_3$) δ 8.45 (d, J=3.0 Hz, 1H), 7.43-7.35 (m, 1H), 7.35-7.29 (m, 1H), 4.21 (br s, 1H), 3.89-3.66 (m, 5H), 3.54 (d, J=9.6 Hz, 1H), 3.04-2.86 (m, 1H), 2.68-2.58 (m, 1H), 2.50-2.29 (m, 2H), 1.99-1.86 (m, 2H), 1.84-1.73 (m, 1H), 1.70-1.62 (m, 1H), 1.45-1.40 (m, 1H), 1.38 (s, 9H), 1.17-1.07 (m, 1H). SFC: Column: CHIRALPAK AD (100 mm*4.6 mm, 3 μm); Mobile Phase: A: CO$_2$; B [0.05% DEA EtOH]; B %: 5%-40% 5.0 min, 40% 2.5 min, 5% 2.5 min; Rt=3.385 min; 93.2% de.

(−)-L5b (350 mg), MS m/z=381.2 [M+1]$^+$. $^1$H NMR (400 MHz, CDCl$_3$) δ 8.44 (d, J=3.0 Hz, 1H), 7.42-7.35 (m, 1H), 7.34-7.29 (m, 1H), 4.21 (br s, 1H), 3.95-3.65 (m, 5H), 3.53 (d, J=9.6 Hz, 1H), 3.03-2.85 (m, 1H), 2.72-2.51 (m, 1H), 2.47-2.33 (m, 2H), 1.99-1.84 (m, 2H), 1.83-1.59 (m, 2H), 1.45-1.39 (m, 1H), 1.38 (s, 9H), 1.16-1.06 (m, 1H). SFC: Column: CHIRALPAK AD (100 mm*4.6 mm, 3 μm); Mobile Phase: A: CO$_2$; B [0.05% DEA EtOH]; B %: 5%-40% 5.0 min, 40% 2.5 min, 5% 2.5 min; Rt=3.623 min; 94.6% de.

(−)-L5a (380 mg), MS m/z=381.2 [M+1]$^+$. SFC: Column: CHIRALPAK AD (100 mm*4.6 mm, 3 μm); Mobile Phase: A: CO$_2$; B: [0.05% DEA EtOH]; B %: 5%-40% 5.0 min, 40% 2.5 min, 5% 2.5 min; Rt=4.366 min; 98.5% de.

Reference Example 8: Synthesis of Intermediate R1

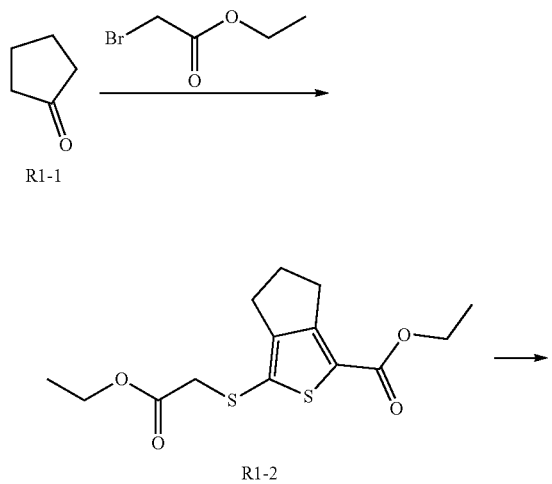

Step 1: Preparation of Compound R1-2

A solution of compound R1-1 (10.0 g, 118.9 mmol) in dimethyl sulfoxide (50.0 mL) was added to a solution of potassium tert-butoxide (26.7 g, 237.8 mmol) in dimethyl sulfoxide (100.0 mL) and stirred at 15 to 20° C. for 0.5 hour, and then carbon disulfide (9.1 g, 118.9 mmol) was added and stirred at 20 to 50° C. for 1 hour. After ethyl bromoacetate (39.7 g, 237.8 mmol) was added, stirring was continued at 25° C. for 16 hours. Then, potassium carbonate (16.4 g, 118.9 mmol) was added to the above reaction system. After the addition was completed, the temperature was raised to 50° C., and the stirring was continued for 2 hours. After the reaction was completed, water (450 mL) was added to the reaction solution, which was then extracted with ethyl acetate (400 mL×3). The combined organic phases were washed with saturated brine (300 mL×2), dried over anhydrous sodium sulfate, and concentrated in vacuum. The concentrate was separated and purified by silica gel column chromatography (eluent: petroleum ether/ethyl acetate=100/1 to 50/1) to give a pale-yellow oily compound R1-2. MS m/z: 315.2 [M+1]$^+$. $^1$H NMR (400 MHz, CDCl$_3$) δ 4.31 (q, J=7.2 Hz, 2H), 4.25-4.17 (m, 2H), 3.56 (s, 2H), 2.96 (t, J=7.4 Hz, 2H), 2.73-2.66 (m, 2H), 2.42 (t, J=7.2 Hz, 2H), 1.39-1.33 (m, 3H), 1.32-1.26 (m, 3H).

Compounds R2-2 and R3-2 were synthesized with reference to the route of synthesis of R1-2:

| Compound Number | Structural Formula | Spectrum |
|---|---|---|
| R2-2 | | $^1$H NMR (400 MHz, CDCl$_3$) δ 5.01 (s, 1H), 4.85 (s, 1H), 4.24-4.18 (m, 4H), 3.59 (s, 2H), 1.25-1.31 (m, 6H). MS m/z: 316.9 [M + 1]$^+$. |
| R3-2 | | $^1$H NMR (400 MHz, CDCl$_3$) δ 4.30 (q, J = 7.2 Hz, 2H), 4.21-4.14 (m, 2H), 3.54 (s, 2H), 3.07-2.95 (m, 2H), 2.79-2.62 (m, 2H), 1.80-1.70 (m, 4H), 1.39-1.32 (m, 3H), 1.26 (t, J = 7.2 Hz, 3H). MS m/z: 329.3[M + 1]$^+$. |

-continued

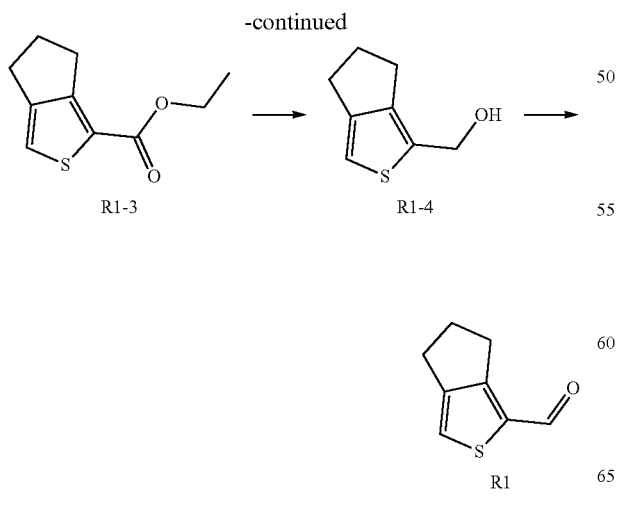

Step 2: Preparation of Compound R1-3

The compound R1-2 (15.2 g, 45.8 mmol) was dissolved in tetrahydrofuran (150.0 mL), palladium dichloride (405.9 mg, 2.3 mmol) was added to the system, and then triethyl silicane (10.7 g, 91.6 mmol) was slowly added. After the addition was completed, the reaction solution was warmed to 70° C. and stirring was continued for 16 hours. After the reaction was completed, the reaction solution was filtered, and the filtrate was concentrated in vacuum. The concentrate was separated and purified by silica gel column chromatography (eluent: petroleum ether/ethyl acetate=100/1 to 80/1) to give a white solid R1-3. MS m/z: 197.1 [M+1]$^+$. $^1$H NMR (400 MHz, CDCl$_3$) δ 6.90 (s, 1H), 4.24 (q, J=7.2 Hz, 2H), 2.86 (t, J=7.4 Hz, 2H), 2.61 (dt, J=1.2, 7.2 Hz, 2H), 2.34 (t, J=7.2 Hz, 2H), 1.29 (t, J=7.2 Hz, 3H).

Compounds R2-3 and R3-3 were synthesized with reference to the route of synthesis of R1-3:

| Compound Number | Structural Formula | Spectrum |
|---|---|---|
| R2-3 | [structure] | $^1$H NMR (400 MHz, CDCl$_3$) δ 7.07 (s, 1H), 5.03 (s, 2H), 4.85 (m, 2H), 4.35-4.30 (m, 2H), 1.38-1.33 (t, J = 1.2 Hz, 3H). MS m/z: 199.0 [M + 1]. |
| R3-3 | [structure] | $^1$H NMR (400 MHz, CDCl$_3$) δ 7.27 (s, 1H, 4.32 (q, J = 7.1 Hz, 2H), 3.04 (t, J = 6.2 Hz, 2H), 2.70 (t, J = 5.8 Hz, 2H), 1.81-1.68 (m, 4H), 1.36 (t, J = 7.2 Hz, 3H). MS m/z: 211.3[M + 1]$^+$. |

Step 3: Preparation of Compound R1-4

The compound R1-3 (1.0 g, 4.7 mmol) was dissolved in anhydrous tetrahydrofuran (10.0 mL), and lithium aluminum hydride (357.4 mg, 9.4 mmol) was added at 0° C. After the addition was completed, the mixture was warmed to 25° C. and reacted for 1 hour. After the reaction was completed, 0.36 mL of water, 0.36 mL of a 15% aqueous sodium hydroxide solution, and 1.0 mL of water were sequentially added to the reaction solution to quench the reaction. The reaction solution was then filtered, and the filtrate was dried over anhydrous sodium sulfate and concentrated in vacuum. The concentrate was separated and purified by silica gel column chromatography (eluent: petroleum ether/ethyl acetate=50/1 to 10/1) to give R1-4. $^1$H NMR (400 MHz, CDCl$_3$) δ 6.64 (s, 1H), 4.62 (s, 2H), 2.57 (t, J=7.2 Hz, 4H), 2.39-2.22 (m, 2H), 1.66 (br s, 1H).

Compounds R2-4 and R3-4 were synthesized with reference to the route of synthesis of R1-4:

| Compound Number | Structural Formula | Spectrum |
|---|---|---|
| R2-4 | [structure] | $^1$H NMR (400 MHz, CDCl$_3$) δ 6.78 (s, 1H), 4.84 (s, 2H), 4.79 (s, 2H), 4.71 (s, 2H), 1.98 (br s, 1H). |
| R3-4 | [structure] | $^1$H NMR (400 MHz, CDCl$_3$) δ 6.82 (s, 1H), 4.73 (s, 2H), 2.70 (q, J = 6.4 Hz, 4H), 1.82-1.69 (m, 5H). |

Step 4: Preparation of Compound R1

At 25° C., the compound R1-4 (540.0 mg, 3.5 mmol) was dissolved in dichloromethane (15.0 mL), manganese dioxide (3.0 g, 35.0 mmol) was added to the system, and the mixture was stirred and reacted for 5 hours. The reaction solution was filtered, and the filtrate was concentrated in vacuum. The concentrate was separated and purified on a thin-layer chromatography plate prepared from silica gel (eluent: petroleum ether/ethyl acetate=10/1) to give R1. MS m/z: 153.1 [M+1]$^+$.

Compounds R2 and R3 were synthesized with reference to the route of synthesis of compound R1:

| Compound Number | Structural Formula | Spectrum |
|---|---|---|
| R2 | | $^1$H NMR (400 MHz, CDCl$_3$) δ 9.83-9.75 (m, 1H), 7.30 (s, 1H), 5.11 (s, 2H), 4.86 (d, J = 0.8 Hz, 2H). |
| R3 | | $^1$H NMR (400 MHz, CDCl$_3$) δ 9.99 (s, 1H), 7.32 (s, 1H), 3.09 (t, J = 6.0 Hz, 2H), 2.74 (t, J = 5.6 Hz, 2H), 1.88-1.74 (m, 4H). MS m/z: 167.2[M + 1]$^+$. |

Example 1: Preparation of Hydrochloride Salts of Chiral Compounds (+)-1a, (−)-1a, (+)-1b, and (−)-1b

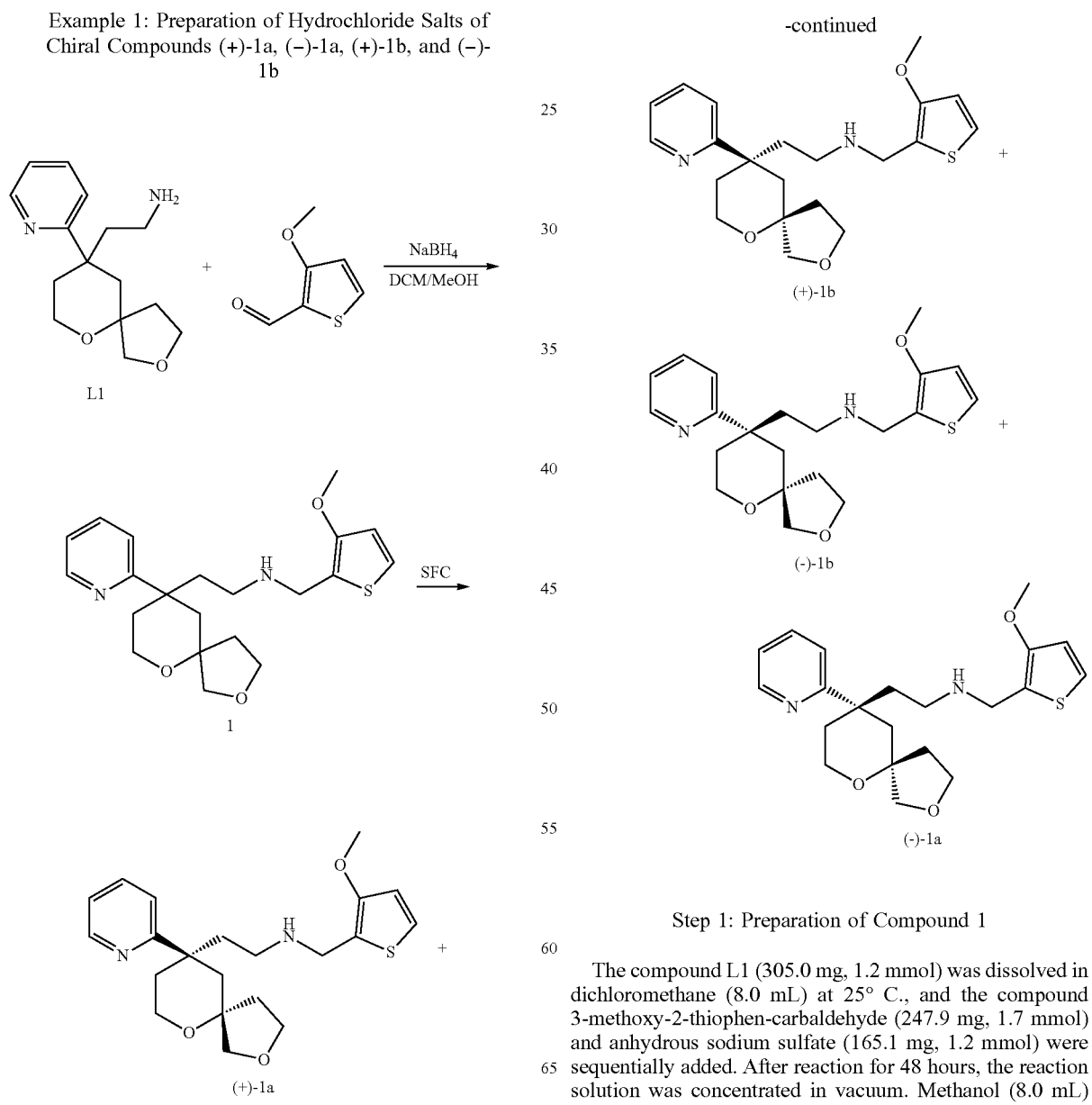

Step 1: Preparation of Compound 1

The compound L1 (305.0 mg, 1.2 mmol) was dissolved in dichloromethane (8.0 mL) at 25° C., and the compound 3-methoxy-2-thiophen-carbaldehyde (247.9 mg, 1.7 mmol) and anhydrous sodium sulfate (165.1 mg, 1.2 mmol) were sequentially added. After reaction for 48 hours, the reaction solution was concentrated in vacuum. Methanol (8.0 mL) was added to the concentrate, and the temperature was lowered to 0° C., and then sodium borohydride (52.8 mg, 1.4 mmol) was added, and the reaction was continued at 25° C. for 16 hours. After the reaction was completed, 5 ml of water was added to quench the reaction. The reaction solution was filtered, the filter residue was washed with ethyl acetate (30 mL), and the filtrate was concentrated in vacuum. The concentrate was separated and purified by silica gel column chromatography (eluent: dichloromethane/ethyl acetate=1/1 to dichloromethane/methanol=5/1) to give compound 1. MS m/z: 389.1 [M+1]. $^1$H NMR (400 MHz, CDCl$_3$) δ 8.58-8.55 (m, 1H), 7.67-7.62 (m, 1H), 7.32-7.28 (m, 1H), 7.15-7.12 (m, 1H), 7.06-7.04 (d, J=8 Hz, 1H), 6.79-6.77 (d, J=8 Hz, 1H), 3.87-3.67 (m, 9.5H), 3.55-3.53 (d, J=8.0 Hz, 0.5H), 3.18-3.15 (d, J=12.0 Hz, 0.5H), 2.85-2.83 (d, J=8.0 Hz, 0.5H), 2.55-2.42 (m, 2H), 2.20-2.12 (m, 1H), 2.05-1.77 (m, 6H), 1.41-1.35 (m, 0.5H), 1.27-1.11 (m, 0.5H).

Step 2: SFC Separation of Compound 1

The compound 1 was separated by SFC (Column: OJ (250 mm*30 mm, 5 μm); Mobile Phase: A: CO$_{O2}$; B: [0.1% NH$_3$H$_2$O EtOH]; B %: 15%) to give four compounds, each of which was added with a 0.2 ml hydrochloric acid-methanol solution (4M) and lyophilized by adding water to give four diastereomers, i.e., a hydrochloride salt of compound (+)-1a (92.4% de), a hydrochloride salt of compound (+)-1b (54.9% de), a hydrochloride salt of compound (−)-1b (86.0% de), and a hydrochloride salt of compound (−)-1a (86.0% de):

Hydrochloride Salt of (+)-1a: MS m/z=389.1 [M+1]$^+$. $^1$H NMR (400 MHz, CD$_3$OD) δ 8.87-8.84 (m, 1H), 8.59-8.55 (m, 1H), 8.11 (d, J=8.4 Hz, 1H), 8.00-7.97 (m, 1H), 7.47 (d, J=4.2 Hz, 1H), 7.00 (d, J=4.2 Hz, 1H), 4.19 (s, 2H), 3.95-3.77 (m, 7H), 3.35-3.33 (m, 1H), 3.07-3.04 (d, J=9.2 Hz, 1H), 2.99-2.92 (m, 1H), 2.56-2.19 (m, 7H), 2.07-1.93 (m, 2H). SFC: Column: Chiralcel OJ-3 (100*4.6 mm, 3 μm); Mobile Phase: A: CO$_2$; B: [0.05% DEA EtOH]; B %: 5% to 40% 4.5 min, 40% 2.5 min, 5% 1 min; Rt=2.255 min; 92.4% de. Optical Rotation: [α]D$^{25}$=+7.0 (C=1, MeOH).

Hydrochloride Salt of (+)-1b: MS m/z=389.1 [M+1]$^+$. $^1$H NMR (400 MHz, CD$_3$OD) δ 8.92-8.88 (m, 1H), 8.71-8.65 (m, 1H), 8.26-8.18 (m, 1H), 8.11-8.06 (m, 1H), 7.47 (d, J=4.2 Hz, 1H), 7.00 (d, J=4.2 Hz, 1H), 4.20 (s, 2H), 3.95-3.73 (m, 8H), 3.61 (d, J=9.2 Hz, 1H), 3.10-2.94 (m, 1H), 2.60-2.40 (m, 3H), 2.36-2.20 (m, 3H), 2.06-1.94 (m, 1H), 1.60-1.54 (m, 1H), 1.37-1.29 (m, 1H). SFC: Column: Chiralcel OJ-3 (100*4.6 mm, 3 μm); Mobile Phase: A: CO$_2$; B: [0.05% DEA EtOH]; B %: 5% to 40% 4.5 min, 40% 2.5 min, 5% 1 min; Rt=2.377 min; 54.9% de. Optical Rotation: [α]D$^{25}$=+25.6 (C=1, MeOH).

Hydrochloride Salt of (−)-1b: MS m/z=389.1 [M+1]$^+$. $^1$H NMR (400 MHz, CD$_3$OD) δ 8.92 (d, J=4.2 Hz, 1H), 8.74-8.70 (m, 1H), 8.28 (d, J=8.4 Hz, 1H), 8.14-8.11 (m, 1H), 7.47 (d, J=4.2 Hz, 1H), 7.01 (d, J=4.2 Hz, 1H), 4.20 (s, 2H), 3.96-3.73 (m, 8H), 3.61 (d, J=9.2 Hz, 1H), 3.05-2.98 (m, 1H), 2.62-2.49 (m, 3H), 2.36-2.22 (m, 3H), 2.08-2.01 (m, 1H), 1.60-1.55 (m, 1H), 1.39-1.31 (m, 1H). SFC: Column: Chiralcel OJ-3 (100*4.6 mm, 3 μm); Mobile Phase: A: CO$_2$; B: [0.05% DEA EtOH]; B %: 5% to 40% 4.5 min, 40% 2.5 min, 5% 1 min; Rt=2.545 min; 86.0% de. Optical Rotation: [α]D$^{25}$=−14.4 (C=1, MeOH).

Hydrochloride Salt of (−)-1a: MS m/z=389.1 [M+1]$^+$. $^1$H NMR (400 MHz, CD$_3$OD) δ 8.80-8.77 (m, 1H), 8.50-8.40 (m, 1H), 7.99-7.95 (m, 1H), 7.89-7.84 (m, 1H), 7.48-7.47 (d, J=4.2 Hz, 1H), 7.02-7.00 (d, J=4.2 Hz, 1H), 4.18 (s, 2H), 3.88-3.79 (m, 7H), 3.39-3.32 (m, 1H), 3.00-2.91 (m, 2H), 2.52-2.17 (m, 7H), 2.07-1.96 (m, 2H). SFC: Column: Chiralcel OJ-3 (100*4.6 mm, 3 μm); Mobile Phase: A: CO$_2$; B: [0.05% DEA EtOH]; B %: 5% to 40% 4.5 min, 40% 2.5 min, 5% 1 min; Rt=2.708 min; 86.0% de. Optical Rotation: [α]D$^{25}$=−12.9 (C=1, MeOH).

The hydrochloride salts of the diastereomers of compound 1 were basified by an aqueous potassium carbonate solution and extracted with ethyl acetate, and the organic phases were concentrated in vacuum to obtain free bases from compounds (+)-1a, (−)-1a, (+)-1b, and (−)-1b in Example 1.

Example 2: Preparation of Compound (+)-2

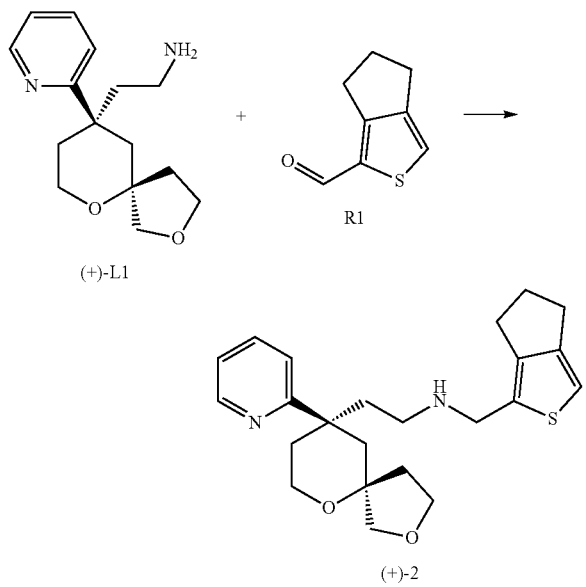

Step 1: Preparation of Compound (+)-2

The hydrochloride salt (170.0 mg, 568.9 μmol) of compound (+)-L1 and the compound R1 (129.9 mg, 853.4 μmol) were dissolved in methanol (5.0 mL), sodium sulfate (80.8 mg, 568.9 μmol) and triethylamine (363.5 mg, 3.59 mmol) were added and stirred at 50° C. for 12 hours. Then, the mixture was cooled to 0° C., sodium borohydride (28.0 mg, 739.6 μmol) was added, and then the temperature was raised to 25° C., and stirring was continued for 2 hours. After the reaction was completed, 10 mL of water was added to quench the reaction, the mixture was extracted with ethyl acetate (20 mL×2), the combined organic phases were washed with saturated brine (20 mL), dried over anhydrous sodium sulfate, and filtered, and the filtrate was concentrated in vacuum. The concentrate was separated and purified by preparative high-performance liquid chromatography (Column: Phenomenex Gemini 150*25 mm, 10 μm; Mobile Phase: [water (0.05% ammonium hydroxide v/v)-acetonitrile]; B %: 39%-69%) to give compound (+)-2. MS m/z: 399.3 [M+1]. $^1$H NMR (400 MHz, CD$_3$OD) δ 8.55 (dd, J=0.8, 4.8 Hz, 1H), 7.79-7.75 (m, 1H), 7.51 (d, J=8.0 Hz, 1H), 7.27-7.23 (m, 1H), 6.67 (s, 1H), 3.84-3.75 (m, 3H), 3.72-3.62 (m, 4H), 3.54 (d, J=9.2 Hz, 1H), 2.66-2.56 (m, 2H), 2.55-2.41 (m, 5H), 2.37-2.26 (m, 2H), 2.07-1.86 (m, 3H), 1.79-1.65 (m, 2H), 1.45-1.39 (m, 1H), 1.21-1.16 (m, 1H).

The following compounds were synthesized using a method similar to compound (+)-2, wherein, in Example 4, a formate salt of compound (+)-4 was obtained by separation and purification in a formic acid system by using preparative high-performance liquid chromatography (Column: Phenomenex Synergi C18 150*30 mm*4 μm; Mobile Phase: [water (0.225% formic acid)-ACN]; B %: 15%-45%, 10.5 min)). The formate salt of compound (+)-4 was basified by an aqueous potassium carbonate solution and extracted with ethyl acetate, and the organic phase was concentrated in vacuum to obtain a free base from compound (+)-4.

The compounds (+)-L3 (50.0 mg, 178.4 μmol) and R1 (35.3 mg, 231.9 μmol) were added to dichloromethane (3.0 mL) acting as a solvent, and then anhydrous sodium sulfate (126.7 mg, 891.8 μmol) was added, and the reaction solution was stirred at 30° C. for 16 hours. Then, sodium borohydride (8.9 mg, 231.9 μmol) was added and stirred for 10 minutes, and then methanol (1.0 mL) was added, and the reaction solution was continued to be stirred for 2 hours. The reaction solution was poured into 20 mL of water and extracted with

| Example | Compound Number | Segment L | Segment R | Structural Formula | Spectrum |
|---|---|---|---|---|---|
| 3 | (+)-3 | (+)-L2 | (structure with methoxy thiophene aldehyde) | (structure) | $^1$H NMR (400 MHz, CD$_3$OD) δ 7.42-7.36 (m, 2H), 7.18 (d, J = 5.6 Hz, 1H), 7.11-7.04 (m, 2H), 6.88 (d, J = 5.6 Hz, 1H), 3.85-3.78 (m, 6H), 3.71 (dd, J = 4.8, 9.4 Hz, 2H), 3.65 (s, 2H), 3.54 (d, J = 9.2 Hz, 1H), 2.41 (dt, J = 5.0, 11.6 Hz, 1H), 2.34-2.17 (m, 2H), 2.04 (dt, J = 4.8, 11.4 Hz, 1H), 1.93 (d, J = 13.9 Hz, 1H), 1.88-1.63 (m, 3H), 1.54 (td, J = 4.4, 13.2 Hz, 1H), 1.32 (td, J = 9.2, 13.2 Hz, 1H). MS m/z: 406.2[M + 1]. |
| 4 | (+)-4 | (+)-L2 | R1 | (structure) | $^1$H NMR (400 MHz, CD$_3$OD) δ 8.51 (br s, 1H), 7.50-7.40 (m, 2H), 7.14 (t, J = 8.8 Hz, 2H), 6.92 (s, 1H), 4.23-4.08 (m, 2H), 3.86-3.69 (m, 3H), 3.75-3.67 (m, 2H), 3.56 (d, J = 9.2 Hz, 1H), 3.60-3.52 (m, 1H), 2.93-2.82 (m, 1H), 2.69-2.51 (m, 4H), 2.43-2.24 (m, 5H), 2.08-1.71 (m, 4H), 1.53 (td, J = 4.4, 13.2 Hz, 1H), 1.29 (td, J = 9.2, 13.2 Hz, 1H). MS m/z: 416.2[M + 1]. |

Example 5: Preparation of Compound (+)-5

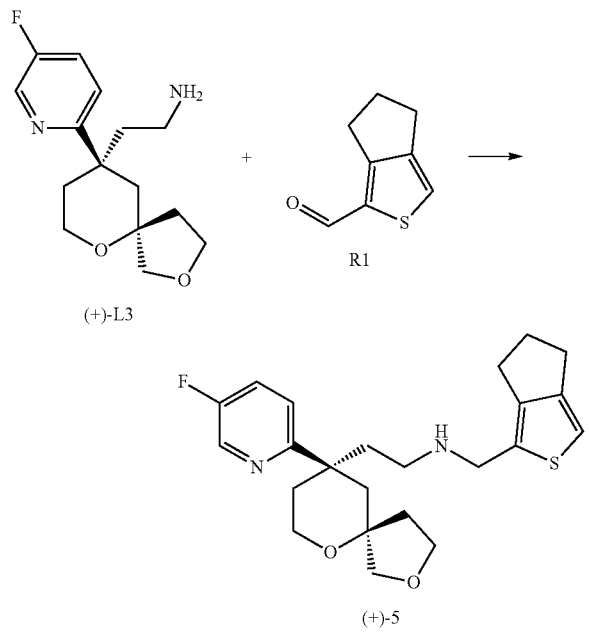

ethyl acetate (20 mL×3), the combined organic phases were washed with saturated brine (25 mL), dried over anhydrous sodium sulfate, and filtered, and the filtrate was concentrated in vacuum. The concentrate was separated and purified by preparative high-performance liquid chromatography (Column: Xtimate C18 150*25 mm*5 μm; Mobile Phase: [water (10 mM NH$_4$HCO$_3$)-ACN]; B %: 45%-55%) to give compound (+)-5. MS m/z: 417.1 [M+1]. $^1$H NMR (400 MHz, CDCl$_3$) δ 8.44 (d, J=2.8 Hz, 1H), 7.42-7.29 (m, 2H), 6.62 (s, 1H), 3.94-3.64 (m, 7H), 3.55 (d, J=9.2 Hz, 1H), 2.68-2.56 (m, 2H), 2.54-2.25 (m, 7H), 2.17-2.08 (m, 1H), 1.99-1.88 (m, 2H), 1.83-1.64 (m, 2H), 1.45-1.35 (m, 1H), 1.21-1.05 (m, 1H).

The following compounds were synthesized using a method similar to compound (+)-5, wherein, in Example 12, a hydrochloride salt of compound (+)-12 was obtained by separation and purification in a hydrochloric acid system by using preparative high-performance liquid chromatography (Column: Waters Xbridge 150*25 mm, 5 μm; Mobile Phase: [water (0.05% (hydrochloric acid)-ACN]; B %: 10%-30%, 12 min). The hydrochloride salt of compound (+)-12 was basified by an aqueous potassium carbonate solution and extracted with ethyl acetate, and the organic phase was concentrated in vacuum to obtain a free base from compound (+)-12.

| Example | Compound Number | Segment L | R | Structural Formula | Spectrum |
|---|---|---|---|---|---|
| 6 | (+)-6 | (+)-L4 | R1 | | ¹H NMR (400 MHz, CDCl₃) δ 8.54 (dd, J = 5.6, 8.8 Hz, 1H), 7.02 (dd, J = 2.4, 10.8 Hz, 1H), 6.93-6.80 (m, 1H), 6.60 (s, 1H), 3.88-3.63 (m, 7H), 3.54 (d, J = 9.2 Hz, 1H), 2.63-2.55 (m, 2H), 2.53-2.25 (m, 7H), 2.20-2.09 (m, 1H), 1.99-1.86 (m, 2H), 1.83-1.64 (m, 2H), 1.52-1.37 (m, 1H), 1.29-1.09 (m, 1H). MS m/z: 417.3 [M + 1]⁺. |
| 7 | (+)-7 | (+)-L1 | R2 | | ¹H NMR (400 MHz, CDCl₃) δ 8.59-8.58 (m, 1H), 7.65 (dt, J = 8.0, 15.6 Hz, 1H), 7.32-7.24 (m, 1H), 7.19-7.16 (m, 1H), 6.66 (s, 1H), 4.74 (s, 2H), 4.69 (s, 2H), 3.84-3.62 (m, 7H), 3.54 (d, J = 9.2 Hz, 1H), 2.49-2.44 (m, 3H), 2.17-2.10 (m, 1H), 1.99-1.95 (m, 1H), 1.93-1.92 (m, 1H), 1.90-1.87 (m, 1H), 1.80-1.68 (m, 1H), 1.43-1.37 (m, 1H), 1.18-1.11 (m, 1H). MS m/z: 401.2 [M + 1]⁺. |
| 8 | (+)-8 | (+)-L1 | | | ¹H NMR (400 MHz, CDCl₃) δ 8.56 (d, J = 3.2 Hz, 1H), 7.65 (t, J = 14.8 Hz, 1H), 7.29-7.25 (m, 1H), 7.16-7.11 (m, 4H), 7.04-6.99 (m, 1H), 3.82-3.51 (m, 8H), 2.49-2.41 (m, 3H), 2.13-2.06 (m, 1H), 1.99-1.85 (m, 2H), 1.76-1.67 (m, 2H), 1.39-1.37 (m, 1H), 1.16-1.08 (m, 1H). MS m/z: 387.4 [M + 1]⁺. |
| 9 | (+)-9 | (+)-L1 | | | ¹H NMR (400 MHz, CDCl₃) δ 8.57 (dd, J = 1.2, 5.2 Hz, 1H), 7.64 (dt, J = 2.0, 8.0 Hz, 1H), 7.30 (d, J = 8.4 Hz, 1H), 7.16-7.12 (m, 2H), 7.04-6.98 (m, 3H), 3.84-3.68 (m, 5H), 3.59 (d, J = 0.8 Hz, 2H), 3.53 (d, J = 9.2 Hz, 1H), 2.56-2.49 (m, 1H), 2.43 (d, J = 16 Hz, 2H), 2.30 (s, 3H), 2.15 (dt, J = 5.2, 11.2 Hz, 1H), 2.00 (dt, J = 2.0, 6.8 Hz, 1H), 1.83 (d, J = 32 Hz, 1H), 1.78-1.73 (m, 2H), 1.42-1.36 (m, 1H), 1.17-1.09 (m, 1H). MS m/z: 367.4 [M + 1]⁺. |
| 10 | (+)-10 | (+)-L1 | | | ¹H NMR (400 MHz, CDCl₃) δ 8.58-8.56 (m, 1H), 7.64 (dt, J = 1.6, 7.6 Hz, 1H), 7.30 (d, J = 8.0 Hz, 1H), 7.14 (ddd, J = 0.8, 4.4, 5.6 Hz, 1H), 6.86 (s, 1H), 6.81 (s, 2H), 3.86-3.55 (m, 8H), 2.54-2.43 (m, 3H), 2.26 (s, 6H), 2.17-2.11 (m, 1H), 2.04-1.96 (m, 1H), 1.90 (d, J = 13.6 Hz, 1H), 1.80-1.71 (m, 2H), 1.43-1.37 (m, 1H), 1.17-1.10 (m, 1H). MS m/z: 381.4 [M + 1]⁺. |
| 11 | (+)-11 | (+)-L1 | | | ¹H NMR (400 MHz, CDCl₃) δ 8.59 (dd, J = 0.8, 2.0 Hz, 1H), 7.65 (dt, J = 0.8, 9.6 Hz, 1H), 7.31 (d, J = 8.0 Hz, 1H), 7.14 (ddd, J = 0.8, 4.4, 7.4 Hz, 1H), 7.04-7.00 (m, 1H), 6.98-6.94 (m, 2H), 3.88-3.80 (m, 3H), 3.79-3.67 (m, 2H), 3.55 (t, J = 8.8 Hz, 3H), 2.76 (t, J = 6.0 Hz, 2H), 2.63 (t, J = 6.0 Hz, 2H), 2.57- |

-continued

| Example | Compound Number | Segment L | Segment R | Structural Formula | Spectrum |
|---|---|---|---|---|---|
| | | | | | 2.44 (m, 3H), 2.24-2.14 (m, 1H), 2.03-1.69 (m, 8H), 1.44-1.38 (m, 1H), 1.20-1.12 (m, 1H). MS m/z: 407.4 [M + 1]⁺. |
| 12 | (+)-12 | (+)-L2 | R2 | | ¹H NMR (400 MHz, CD₃OD) δ 7.50-7.41 (m, 2H), 7.18-7.09 (m, 3H), 4.80-4.72 (m, 4H), 4.20-4.12 (m, 2H), 3.86-3.75 (m, 3H), 3.70 (dd, J = 4.4, 9.2 Hz, 2H), 3.55 (d, J = 9.2 Hz, 1H), 2.97-2.85 (m, 1H), 2.45-2.33 (m, 2H), 2.29 (d, J = 14.0 Hz, 1H), 2.06-1.93 (m, 2H), 1.92-1.72 (m, 2H), 1.54-1.47 (m, 1H), 1.38-1.22 (m, 2H). MS m/z: 418.4[M + 1]. |
| 13 | (+)-13 | (+)-L2 | | | ¹H NMR (400 MHz, CDCl₃) δ 7.29-7.27 (m, 1H), 7.26-7.24 (m, 1H), 7.09-7.00 (m, 3H), 6.76 (d, J = 5.2 Hz, 1H), 3.88-3.71 (m, 7H), 3.54 (d, J = 9.6 Hz, 1H), 2.47 (dt, J = 5.6, 10.8 Hz, 1H), 2.32-2.23 (m, 1H), 2.21-2.09 (m, 2H), 2.11 (s, 3H), 1.96-1.87 (m, 1H), 1.84-1.67 (m, 3H), 1.56-1.50 (m, 1H), 1.28-1.23 (m, 1H). MS m/z: 390.4[M + 1]. |
| 14 | (+)-14 | (+)-L2 | | | ¹H NMR (400 MHz, CDCl₃) δ 7.23-7.17 (m, 2H), 7.10 (dd, J = 1.2, 5.2 Hz, 1H), 7.00-6.91 (m, 2H), 6.83 (dd, J = 3.6, 5.2 Hz, 1H), 6.73 (dd, J = 0.8, 3.4 Hz, 1H), 3.79-3.60 (m, 7H), 3.46 (d, J = 9.6 Hz, 1H), 2.39 (dt, J = 5.6, 11.0 Hz, 1H), 2.23-2.14 (m, 1H), 2.12-2.03 (m, 2H), 1.86 (d, J = 14.0 Hz, 1H), 1.79-1.61 (m, 3H), 1.52-1.41 (m, 1H), 1.22-1.14 (m, 1H). MS m/z: 376.3[M + 1]. |
| 15 | (+)-15 | (+)-L3 | R3 | | ¹H NMR (400 MHz, CDCl₃) δ 8.44 (d, J = 2.8 Hz, 1H), 7.42-7.29 (m, 2H), 6.72 (s, 1H), 3.90-3.65 (m, 7H), 3.55 (d, J = 9.6 Hz, 1H), 2.70-2.63 (m, 2H), 2.56-2.35 (m, 5H), 2.26-2.08 (m, 1H), 2.00-1.86 (m, 2H), 1.85-1.63 (m, 6H), 1.49-1.27 (m, 1H), 1.19-1.12 (m, 1H). MS m/z: 431.1 [M + 1]⁺. |
| 16 | (+)-16 | (+)-L3 | | | ¹H NMR (400 MHz, CDCl₃) δ 8.36 (d, J = 3.0 Hz, 1H), 7.34-7.26 (m, 1H), 7.24-7.20 (m, 1H), 7.14-7.08 (m, 3H), 7.01-6.94 (m, 1H), 3.82-3.58 (m, 5H), 3.51 (s, 2H), 3.46 (d, J = 9.6 Hz, 1H), 2.45-2.22 (m, 3H), 2.05-1.95 (m, 1H), 1.90-1.79 (m, 2H), 1.75-1.57 (m, 2H), 1.35-1.27 (m, 1H), 1.09-1.02 (m, 1H). MS m/z: 405.1 [M + 1]⁺. |

-continued

| Example | Compound Number | Segment L | R | Structural Formula | Spectrum |
|---|---|---|---|---|---|
| 17 | (+)-17 | (+)-L3 | 4-chlorobenzaldehyde | (structure) | ¹H NMR (400 MHz, CDCl₃) δ 8.45 (d, J = 2.8 Hz, 1H), 7.42-7.34 (m, 1H), 7.32-7.23 (m, 3H), 7.14 (d, J = 8.4 Hz, 2H), 3.87-3.67 (m, 5H), 3.63-3.50 (m, 3H), 2.56-2.34 (m, 3H), 2.15-2.05 (m, 1H), 2.00-1.85 (m, 2H), 1.83-1.62 (m, 2H), 1.45-1.40 (m, 1H), 1.19-1.13 (m, 1H). MS m/z: 405.2 [M + 1]⁺. |
| 18 | (+)-18 | (+)-L1 | 3-fluoro-5-chlorobenzaldehyde | (structure) | ¹H NMR (400 MHz, CD₃OD) δ 8.53-8.50 (m, 1H), 7.77-7.73 (m, 1H), 7.48 (d, J = 8.0 Hz, 1H), 7.24-7.21 (m, 1H), 7.06-7.01 (m, 2H), 6.91 (d, J = 9.6 Hz, 1H), 3.80-3.75 (m, 3H), 3.69-3.64 (m, 2H), 3.57(s, 2H), 3.52 (d, J = 9.2 Hz, 1H), 2.50-2.35 (m, 3H), 2.02-1.92 (m, 2H), 1.89 (d, J = 14.0 Hz, 1H), 1.76-1.68 (m, 2H), 1.41-1.35 (m, 1H), 1.19-1.14 (m, 1H). MS m/z: 405.3[M + 1]⁺. |
| 19 | (+)-19 | (+)-L1 | indane carbaldehyde | (structure) | ¹H NMR (400 MHz, CD₃OD) δ 8.52 (d, J = 4.0 Hz, 1H), 7.77-7.73 (m, 1H), 7.48 (d, J = 8.0 Hz, 1H), 7.24-7.21 (q, J = 7.2, 4.8 Hz, 1H), 7.08-7.00 (m, 2H), 6.91 (d, J = 7.6 Hz, 1H), 3.82-3.74 (m, 3H), 3.69-3.65 (m, 2H), 3.54-3.51 (m, 3H), 2.87 (t, J = 7.6 Hz, 2H), 2.79 (t, J = 7.2 Hz, 2H), 2.51-2.44 (m, 3H), 2.06-1.96 (m, 4H), 1.88 (d, J = 14.0 Hz, 1H), 1.77-1.67 (m, 2H), 1.41-1.35 (m, 1H), 1.20-1.12 (m, 1H). MS m/z: 393.4 [M + 1]⁺. |
| 20 | (+)-20 | (+)-L1 | 3,4-dichlorobenzaldehyde | (structure) | ¹H NMR (400 MHz, CDCl₃) δ 8.58 (d, J = 4 Hz, 1H), 7.68-7.63 (m, 1H), 7.33-7.28 (m, 2H), 7.24 (s, 1H), 7.16-7.13 (m, 1H), 7.00 (dd, J = 1.6, 8.0 Hz, 1H), 3.84-3.69 (m, 5H), 3.58-3.51 (m, 3H), 2.46-2.42 (m, 3H), 2.12-2.05 (m, 1H), 1.91-1.88 (m, 2H), 1.74-1.71 (m, 2H), 1.43-1.38 (m, 1H), 1.18-1.10 (m, 1H). MS m/z: 421.4 [M + 1]⁺. |
| 21 | (+)-21 | (+)-L1 | 3,5-dichlorobenzaldehyde | (structure) | ¹H NMR (400 MHz, CDCl₃) δ 8.59 (d, J = 3.6 Hz, 1H), 7.66 (m, 1H), 7.31-7.29 (m, 1H), 7.20-7.14 (m, 2H), 7.07-7.06 (d, J = 1.2 Hz, 2H), 3.84-3.69 (m, 5H), 3.56-3.54 (m, 3H), 2.47-2.44 (m, 3H), 2.14-2.07 (m, 1H), 1.98-1.89 (m, 2H), 1.76-1.73 (m, 2H), 1.43-1.40 (m, 1H), 1.16-1.13 (m, 1H). MS m/z: 421.3 [M + 1]⁺. |

Example 22: Preparation of Hydrochloride Salt of Compound (+)-22

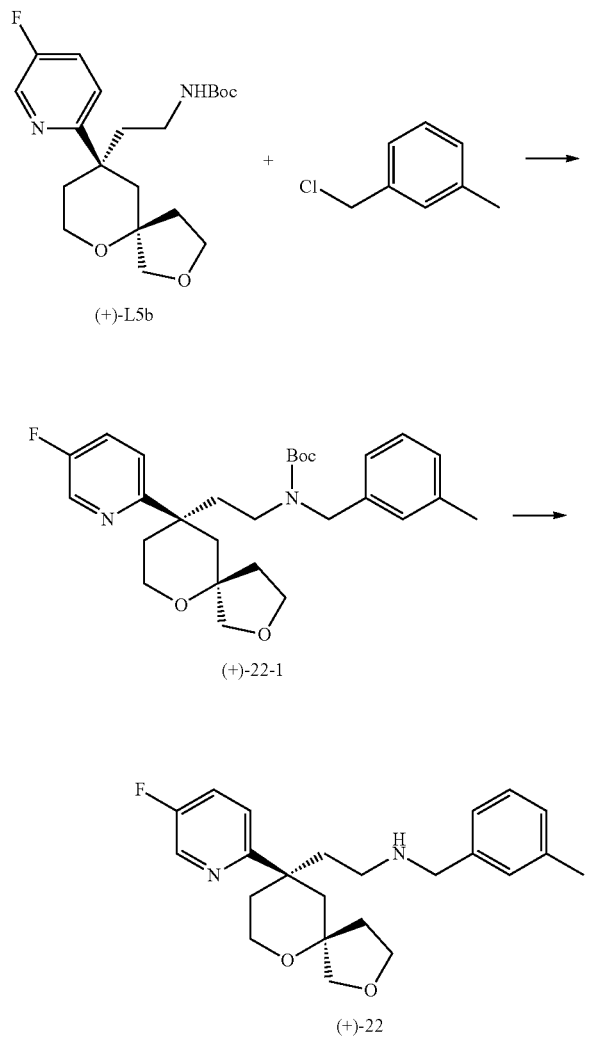

Step 1: Preparation of Compound (+)-22-1

The compound (+)-L5b (150.0 mg, 394.3 μmol) was dissolved in N,N-dimethylformamide (3.0 mL), NaH (18.9 mg, 473.1 μmol, purity: 60%) was added at 0° C. and stirred for 30 minutes, and then 3-methylbenzyl chloride (72.1 mg, 512.6 μmol) was added. After the reaction solution was slowly warmed to 15° C., the reaction was continued for 16 hours. The reaction solution was poured into 20 mL of ice water and extracted with ethyl acetate (20 ml*3). The combined organic phases were washed with saturated brine (20 mL), dried over anhydrous sodium sulfate, and concentrated in vacuum to give a crude product. The crude product was separated and purified by silica gel column chromatography (eluent: petroleum ether/ethyl acetate=1/10 to 1/2) to give (+)-22-1. MS m/z: 485.1 [M+1]$^+$. $^1$H NMR (400 MHz, CDCl$_3$) δ 8.42 (d, J=3.0 Hz, 1H), 7.39-7.30 (m, 1H), 7.26-7.10 (m, 2H), 7.04 (d, J=7.6 Hz, 1H), 6.88-6.79 (m, 2H), 4.34-3.96 (m, 2H), 3.85-3.63 (m, 5H), 3.51 (d, J=9.4 Hz, 1H), 3.18-2.83 (m, 1H), 2.61-2.23 (m, 3H), 2.30 (s, 3H), 2.01-1.61 (m, 4H), 1.43 (s, 9H), 1.40-1.37 (m, 1H), 1.15-1.05 (m, 1H).

Step 2: Preparation of Hydrochloride Salt of Compound (+)-22

The compound (+)-22-1 (190.0 mg, 392.1 umol) was dissolved in dioxane (2.0 mL), and then hydrochloric acid/dioxane (2 mL, 4 M) was added, and the reaction solution was continued to react at 15° C. for 16 hours. The reaction solution was concentrated in vacuum and then lyophilized by adding water to give a hydrochloride salt of (+)-22. MS m/z: 385.2 [M+1]$^+$. $^1$H NMR (400 MHz, CD$_3$OD) δ 8.63 (d, J=1.8 Hz, 1H), 7.97-7.67 (m, 2H), 7.37-7.10 (m, 4H), 4.09-3.97 (m, 2H), 3.89-3.65 (m, 5H), 3.56 (d, J=9.2 Hz, 1H), 3.08-2.87 (m, 1H), 2.58-2.41 (m, 3H), 2.35 (s, 3H), 2.18 (br d, J=4.4 Hz, 1H), 2.04-1.92 (m, 2H), 1.88-1.74 (m, 1H), 1.49-1.40 (m, 1H), 1.26-1.15 (m, 1H). The hydrochloride salt of the compound (+)-22 was basified by an aqueous potassium carbonate solution and extracted with ethyl acetate, and the organic phase was concentrated in vacuum to obtain a free base from compound (+)-22.

The following compounds (+)-23-1, (+)-24-1, and (+)-16-1 were synthesized using a method similar to compound (+)-22-1:

| Compound Number | Segment L | R | Structural Formula | Spectrum |
|---|---|---|---|---|
| (+)-23-1 | (+)-L5b | | 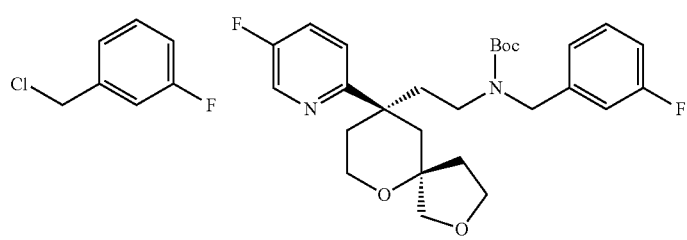 | MS m/z: 489.1 [M + 1]$^+$. |

-continued

| Compound Number | Segment L | R | Structural Formula | Spectrum |
|---|---|---|---|---|
| (+)-24-1 | (+)-L5b | 3,5-dichlorobenzyl chloride | [structure: 5-fluoropyridine attached to spiro-bicyclic tetrahydropyran-tetrahydrofuran core with ethyl chain to N(Boc)-CH2-(3,5-dichlorophenyl)] | MS m/z: 593.3 [M + 1]⁺. |
| (+)-16-1 | (+)-L5b | 3-chlorobenzyl chloride | [structure: 5-fluoropyridine attached to spiro-bicyclic tetrahydropyran-tetrahydrofuran core with ethyl chain to N(Boc)-CH2-(3-chlorophenyl)] | MS m/z: 505.1 [M + 1]⁺. |

Hydrochloride salts of the following compounds (+)-23, (+)-24, and (+)-16 were synthesized using a method similar to the hydrochloride salt of compound (+)-22. The hydrochloride salts of compounds (+)-23, (+)-24, and (+)-16 were basified by an aqueous potassium carbonate solution and extracted with ethyl acetate, and the organic phase was concentrated in vacuum to obtain free bases corresponding thereto.

| Example | Compound Number | Structural Formula | Spectrum |
|---|---|---|---|
| 23 | (+)-23 | [structure: 5-fluoropyridine attached to spiro-bicyclic core with ethyl-NH-CH2-(3-fluorophenyl)] | ¹H NMR (400 MHz, CD₃OD) δ 8.66 (d, J = 2.4 Hz, 1H), 7.96-7.75 (m, 2H), 7.47 (dt, J = 6.0, 8.0 Hz, 1H), 7.35-7.11 (m, 3H), 4.20-4.03 (m, 2H), 3.92-3.68 (m, 5H), 3.58 (d, J = 9.2 Hz, 1H), 3.03 (dt, J = 4.4, 12.4 Hz, 1H), 2.64-2.45 (m, 3H), 2.21 (dt, J = 4.4, 12.8 Hz, 1H), 2.08-1.96 (m, 2H), 1.91-1.80 (m, 1H), 1.51-1.42 (m, 1H), 1.27-1.19 (m, 1H). MS m/z: 389.0 [M + 1]⁺. |
| 24 | (+)-24 | [structure: 5-fluoropyridine attached to spiro-bicyclic core with ethyl-NH-CH2-(3,5-dichlorophenyl)] | MS m/z: 439.2 [M + 1]⁺. ¹H NMR (400 MHz, CD₃OD) δ 8.65-8.50 (m, 2H), 7.90-7.68 (m, 2H), 7.45-7.33 (m, 3H), 4.10-3.90 (m, 2H), 3.80-3.55 (m, 5H), 3.47 (d, J = 9.6 Hz, 1H), 3.00-2.85 (m, 1H), 2.50-2.35 (m, 3H), 2.17-2.05 (m, 1H), 2.00-1.87 (m, 2H), 1.82-1.71 (m, 1H), 1.42-1.32 (m, 1H), 1.25-1.08 (m, 1H). |

Example 25: Preparation of Compound (+)-25

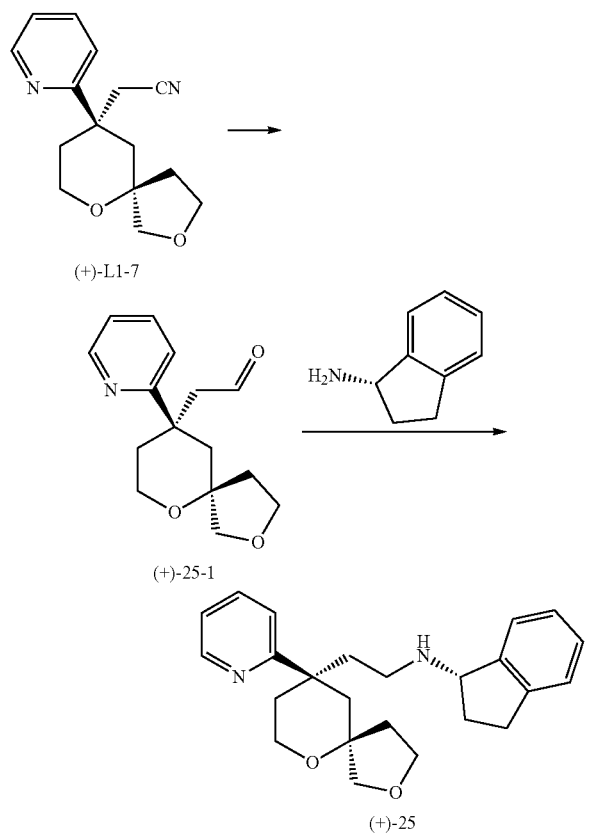

Step 1: Preparation of Compound (+)-25-1

DIBAL-H (1 M toluene solution, 2.32 mL) was added dropwise to a solution of the compound (+)-L1-7 (200.0 mg, 0.77 mmol) in toluene (3 mL) at −78° C. under a nitrogen atmosphere, and a reaction was continued at −78° C. for 2 h. Methanol (0.16 mL) and water (0.06 mL) were sequentially added to the reaction solution, which was slowly returned to room temperature and then continued to be stirred for 10 minutes, and anhydrous sodium sulfate (160 mg) was added and stirred for 30 minutes. The reaction solution was then filtered, and the filtrate was concentrated in vacuum. The resulting concentrate was dissolved in THF (4.0 mL), and hydrochloric acid (2 M, 1.0 mL) was added. After being stirred at 20° C. for 30 minutes, the reaction solution was concentrated in vacuum to give (+)-25-1 (crude product). MS m/z: 262.2 [M+1]⁺. The crude product was used directly in the next reaction without further purification.

Step 2: Preparation of Compound (+)-25

The compound (+)-25-1 (100.0 mg) and (S)-(+)-1-aminoindene (76.5 mg, 0.57 mmol) were dissolved in MeOH (3.0 mL) at 20° C., and then acetic acid (0.1 mL) and sodium cyanoborohydride (72.1 mg, 1.15 mmol) were added sequentially to the reaction system, which was then stirred and reacted at 20° C. for 12 h. The reaction solution was filtered, and the filtrate was separated and purified by preparative high-performance liquid chromatography (Column: Xtimate C18 150*25 mm*5 μm; Mobile Phase: [water (0.04% NH$_3$H$_2$O+10 mM NH$_4$HCO$_3$)-ACN]; B %: 30%-60%, 10.5 min) to give compound (+)-25. MS m/z: 379.3 [M+1]⁺. $^1$H NMR (400 MHz, CDCl$_3$) δ 8.60 (dd, J=0.8, 4.8 Hz, 1H), 7.68-7.64 (m, 1H), 7.33 (d, J=8.0 Hz, 1H), 7.19-7.11 (m, 5H), 4.06 (t, J=6.4 Hz, 1H), 3.86-3.62 (m, 5H), 3.55 (d, J=9.2 Hz, 1H), 2.95-2.88 (m, 1H), 2.77-2.765 (m, 1H), 2.60-2.40 (m, 3H), 2.29-2.18 (m, 2H), 2.01-1.88 (m, 2H), 1.83-1.71 (m, 2H), 1.70-1.50 (m, 2H), 1.48-1.38 (m, 1H), 1.25-1.10 (m, 1H).

The following compound (+)-26-1 was synthesized using a method similar to compound (+)-25-1:

| Compound Number | Structural Formula | Spectrum |
|---|---|---|
| (+)-26-1 | ![structure] | MS m/z: 280.1 [M + 1]⁺. |

The following compounds were synthesized using a method similar to compound (+)-25:

| Example | Compound Number | Segment L | Segment R | Structural Formula | Spectrum |
|---|---|---|---|---|---|
| 26 | (+)-26 | (+)-26-1 | ![naphthyl] | ![structure] | MS m/z: 411.2 [M + 1]⁺. $^1$H NMR (400 MHz, CDCl$_3$) δ 8.36 (d, J = 2.8 Hz, 1H), 7.35-7.21 (m, 2H), 7.11-6.88 (m, 4H), 3.79-3.58 (m, 5H), 3.54-3.42 (m, 2H), 2.73-2.52 (m, 2H), 2.45-2.27 (m, 3H), 2.15 (dt, J = 4.8, 10.8 Hz, 1H), 1.89-1.31 (m, 9H), 1.11-1.06 (m, 1H) |

| Example | Compound Number | Segment L | Segment R | Structural Formula | Spectrum |
|---|---|---|---|---|---|
| 27 | (+)-27 | (+)-25-1 | | | MS m/z: 393.3 [M + 1]+. 1H NMR (400 MHz, CDCl3) δ 8.60 (dd, J = 0.8, 4.8 Hz, 1H), 7.68-7.64 (m, 1H), 7.33 (d, J = 8.0 Hz, 1H), 7.15-7.01 (m, 5H), 3.86-3.65 (m, 5H), 3.60-3.50 (m, 2H), 2.78-2.60 (m, 2H), 2.50-2.40 (m, 3H), 2.28-2.18 (m, 1H), 1.99-1.90 (m, 2H), 1.88-1.60 (m, 6H), 1.50-1.25 (m, 2H), 1.19-1.10 (m, 1H). |

Example 28: Preparation of Compound (+)-28

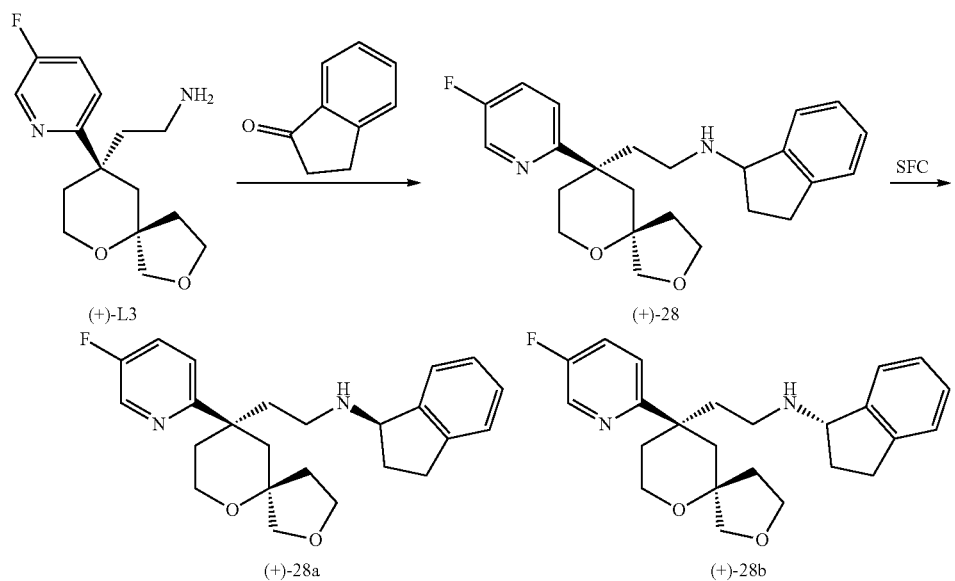

Step 1: Preparation of Compound (+)-28

The compound (+)-L3 (0.30 g, 1.07 mmol, a hydrochloride salt), 4-bromo-1-indanone (282.86 mg, 2.14 mmol), and acetic acid (198.5 mg, 3.30 mmol) were added to a solvent MeOH (3.0 mL), then sodium cyanoborohydride (201.7 mg, 3.21 mmol) was added, and a reaction was continued at 60° C. for 16 hours. The reaction solution was poured into 10.0 mL of water and extracted with ethyl acetate (15.0 mL×3). The organic phases were combined, washed once with 5.0 mL of saturated saline, dried over anhydrous sodium sulfate, and filtered, and the organic solvent was removed to give a crude product. The crude product was separated and purified by preparative high-performance liquid chromatography (Column: Waters Xbridge 150*25 mm*5 μm; Mobile Phase: [water (10 mM NH4HCO3)-ACN]; B %: 27%-57%, 7 min) to give compound (+)-28.

Step 2: Preparation of Compound (+)-28b

The compound (+)-28 was separated by SFC (Column: ChiralPak AD-3 150×4.6 mm I.D., 3 μm; Mobile Phase: A: $CO_2$; B: Ethanol (0.05% DEA)) to give two compounds, i.e., compound (+)-28a (100% de) and compound (+)-28b (100% de):

(+)-28a: MS m/z=397.3 [M+1]+. 1H NMR (400 MHz, CDCl3) δ 8.44 (d, J=2.8 Hz, 1H), 7.42-7.29 (m, 2H), 7.23-7.10 (m, 4H), 4.06 (t, J=6.4 Hz, 1H), 3.91-3.66 (m, 5H), 3.54 (d, J=9.4 Hz, 1H), 2.98-2.85 (m, 1H), 2.80-2.68 (m, 1H), 2.62-2.51 (m, 1H), 2.49-2.34 (m, 2H), 2.31-2.12 (m, 2H), 2.01-1.92 (m, 3H), 1.81-1.65 (m, 3H), 1.48-1.36 (m, 1H), 1.19-1.07 (m, 1H). SFC: Column: ChiralPak AD-3 150×4.6 mm I.D., 3 μm; Mobile Phase: A: $CO_2$; B: Ethanol (0.05% DEA); B %: 5%-40% 5.5 min, 40% 3 min, 5% 1.5 min; Rt=4.787 min; 100% de.

(+)-28b: MS m/z=397.3 [M+1]+. 1H NMR (400 MHz, CDCl3) δ 8.35 (d, J=2.8 Hz, 1H), 7.35-7.22 (m, 2H), 7.16-7.02 (m, 4H), 4.09-4.01 (m, 1H), 3.84-3.58 (m, 5H), 3.46 (d, J=12.0 Hz, 1H), 2.98-2.80 (m, 1H), 2.75-2.62 (m, 1H), 2.54-2.44 (m, 1H), 2.38-2.28 (m, 2H), 2.26-2.06 (m, 2H), 1.94-1.66 (m, 6H), 1.38-1.28 (m, 1H), 1.12-1.00 (m, 1H). SFC: Column: ChiralPak AD-3 150×4.6 mm I.D., 3 μm; Mobile Phase: A: $CO_2$; B: Ethanol (0.05% DEA); B %: 5%-40% 5.5 min, 40% 3 min, 5% 1.5 min; Rt=5.412 min; 100% de.

Biological Evaluation
Test 1: MOR cAMP Agonist Activity Test
1.1 Experimental Purpose: To test the cAMP agonist activity of the compounds of the present disclosure on the human μ-subtype opioid receptor (hMOR).
1.2 Experimental Steps:
1.2.1 Compound Formulation
 a. Compound samples were dissolved in DMSO to a storage concentration of 10 mM.
 b. A series of diluted samples were formulated on a 384-well LDV plate. A total of 11 concentration points were obtained by 3.162-fold gradient dilution.
 c. The series of diluted samples were transferred to an experimental plate (Corning-3824) by using an Echo machine, wherein 30 nL was transferred corresponding to each well.
 d. 30 nL of 333 μM DAMGO (enkephalin) (as a positive control well) and 30 nL of DMSO (as a negative control well) were transferred to the corresponding positions on the experimental plate by using the Echo machine.
1.2.2 Detection of MOR cAMP Agonist Activity
 The experiment was performed using a cAMP detection kit from Cisbio (Cisbio #62AM4PEJ).
 a. Assay buffer and stimulation buffer (STB) required for the experiment were formulated.
 Assay Buffer: 1×HBSS (+/+) (Invitrogen #14025-126)
 20 mM HEPES (Invitrogen #15630-130)
 Stimulation Buffer: formulated with the assay buffer, containing 5 μM NKH477 (CAS: 138605-00-2) and 200 μM IBMX (3-isobutyl-1-methylxanthine)
 In a 10 μL reaction system, the final concentration of IBMX was 100 μM, and the final concentration of NKH477 was 2.5 μM.
 b. 5 μL of the stimulation buffer was added first to each well of the experimental plate (30 nL of the compound had already been contained in the well), and then 5 μL of a cell suspension was added. The number of cells in the well was 10,000 cells/well.
 c. The experimental plate was placed in a 37° C. constant-temperature incubator for incubation. The incubation was performed for 40 minutes.
 d. A cAMP standard concentration curve was prepared. The first concentration point was at 2848 nM, and a total of sixteen detection concentrations were obtained by 4-fold gradient dilution. There were three replicates for each concentration point.
 e. The cAMP detection kit from Cisbio was provided therein with a d2-labeled cAMP reagent (d2 reagent) and an Eu-labeled cAMP antibody reagent (Crypate reagent). The above two reagents were formulated according to the kit instructions, and then added to the sample experimental plate and to the cAMP standard concentration experimental plate, respectively. It was necessary to add 5 μL of the d2 reagent and then 5 μL of the Cryptate reagent to each well.
 f. After the experimental plates were left at room temperature for 60 minutes, the experimental plates were read on the Envision.
1.3 Test Results
 $EC_{50}$ and $E_{max}$ indicating the cAMP agonist activity of the compounds of the present disclosure on the human μ-subtype opioid receptor (hMOR) were shown in Table 1. $E_{max}$ was the maximum effect of the compound at the test concentration causing a change in cAMP level (the maximum effect of enkephalin DAMGO was 100%).

TABLE 1

MOR cAMP Activity Test Results

| Example Number | MOR cAMP $EC_{50}$ (nM) | MOR CAMP $E_{max}$ |
|---|---|---|
| Comparative Compound 1 | 3.0 | 82.7% |
| Comparative Compound 2 | 0.9 | 105.4% |
| Hydrochloride Salt of (+)-1a | 1930.0 | 66.3% |
| Hydrochloride Salt of (+)-1b | 10.0 | 48.9% |
| Hydrochloride Salt of (−)-1b | 380.0 | 39.7% |
| Hydrochloride Salt of (−)-1a | 2340.0 | 30.8% |
| (+)-2 | 0.47 | 96% |
| (+)-3 | 3.0 | 82.0% |
| Formate Salt of (+)-4 | 0.07 | 97.0% |
| (+)-5 | 0.1 | 96.5% |
| (+)-6 | 1.8 | 86.5% |
| (+)-7 | 14.1 | 90.4% |
| (+)-8 | 1.8 | 85.3% |
| (+)-9 | 6.1 | 88.9% |
| (+)-10 | 11.6 | 96.6% |
| (+)-11 | 1.4 | 87.2% |
| Hydrochloride Salt of (+)-12 | 6.8 | 83.0% |
| (+)-13 | 4.1 | 61.2% |
| (+)-14 | 19.9 | 80.6% |
| (+)-15 | 0.2 | 99.5% |
| (+)-16 | 0.5 | 91.7% |
| (+)-17 | 8.9 | 78.5% |
| (+)-18 | 4.2 | 87.7% |
| (+)-19 | 4.5 | 69.9% |
| (+)-20 | 3.1 | 99.6% |
| (+)-21 | 2.2 | 92.3% |
| Hydrochloride Salt of (+)-22 | 0.1 | 93.3% |
| Hydrochloride Salt of (+)-23 | 1.0 | 84.5% |
| Hydrochloride Salt of (+)-24 | 0.2 | 95.0% |
| (+)-25 | 4.0 | 90.0% |
| (+)-26 | 0.2 | 96.0% |
| (+)-27 | 0.8 | 91.0% |
| (+)-28a | 4.6 | 11.0% |
| (+)-28b | 0.04 | 90.0% |

1.4 Conclusion
 The compounds of the present disclosure exhibited significant agonistic effects on the μ-receptor-mediated cAMP signaling pathway.
Test 2: β-Arrestin-2 Agonist Activity Test
2.1 Experimental Purpose: To test the β-arrestin-2 agonist activity of the compounds of the present disclosure on the human μ-subtype opioid receptor (hMOR).
2.2 Experimental Steps:
2.2.1 Compound Formulation
 a. All samples were dissolved in DMSO to a storage concentration of 10 mM.
 b. A series of diluted samples were formulated on a 384-well LDV plate. A total of 11 concentration points were obtained by 3.162-fold gradient dilution.
 c. The series of diluted samples were transferred to an experimental plate by using an Echo machine, wherein 60 nL of the compound was transferred corresponding to each well.
 d. 60 nL of 3.33 mM DAMGO (as HPE) and 60 nL of DMSO (as ZPE) were transferred to the corresponding positions on the experimental plate by using the Echo machine.

2.2.2 Operations for MOR β-arrestin-2 Agonist Activity Experiment

The experiment was performed using PathHunter Detection Kit from DiscoveRX Cooperation (DiscoveRX #93-0213C$_3$)

a. Assay buffer and PathHunter detection reagent required for the experiment were formulated.

Assay Buffer: 1×DPBS buffer

PathHunter Detection Reagent: The kit was provided therein with three constituents. According to the kit instructions, Galacton Star, Emerald II, and PathHunter Cell Assay Buffer were mixed at a ratio of 1:5:19 to formulate the detection reagent.

b. 20 μL of MOR β-arrestin-2 cell suspension was added to each well of the experimental plate (the compound had already been contained in the well), wherein the number of cells in each well was 7500 cells/well.

c. The experimental plate was centrifuged at 300 rpm for 30 s and incubated at room temperature for 2 hours.

d. 6 μL of the PathHunter detection reagent was added to each well of the experimental plate.

e. The experimental plate was centrifuged at 300 rpm for 30 seconds, then left at room temperature for 60 minutes, and then read on the Envision.

2.3 Test Results $EC_{50}$ and $E_{max}$ indicating the β-arrestin-2 agonist activity of the compounds of the present disclosure on the human μ-subtype opioid receptor (hMOR) were shown in Table 2. $E_{max}$ was the maximum effect of the compound at the test concentration causing a change in β-arrestin-2 level (the maximum effect of enkephalin DAMGO was 100%).

TABLE 2

MOR β-arrestin-2 Activity Test Results

| Example Number | MOR β-arrestin-2 $EC_{50}$ (nM) | MOR β-arrestin-2 $E_{max}$ |
|---|---|---|
| Comparative Compound 1 | 19.0 | 4.5% |
| Comparative Compound 2 | 500.0 | 35.2% |
| Hydrochloride Salt of (+)-1a | >30000 | about 0%* |
| Hydrochloride Salt of (+)-1b | >30000 | about 0%* |
| Hydrochloride Salt of (−)-1b | >30000 | about 0%* |
| Hydrochloride Salt of (−)-1a | >30000 | about 0%* |
| (+)-2 | >30000 | about 0%* |
| (+)-3 | >30000 | about 0%* |
| Formate Salt of (+)-4 | >30000 | about 0%* |
| (+)-5 | >30000 | about 0%* |
| (+)-6 | >30000 | about 0%* |
| (+)-7 | >30000 | about 0%* |
| (+)-8 | >30000 | about 0%* |
| (+)-9 | >30000 | about 0%* |
| (+)-10 | >30000 | about 0%* |
| (+)-11 | >30000 | about 0%* |
| Hydrochloride Salt of (+)-12 | >30000 | about 0%* |
| (+)-13 | >30000 | about 0%* |
| (+)-14 | >30000 | about 0%* |
| (+)-15 | >30000 | about 0%* |
| (+)-16 | >30000 | about 0%* |
| (+)-17 | >30000 | about 0%* |
| (+)-18 | >30000 | about 0%* |
| (+)-19 | >30000 | about 0%* |
| (+)-20 | >30000 | about 0%* |
| (+)-21 | >30000 | about 0%* |
| Hydrochloride Salt of (+)-22 | >30000 | about 0%* |
| Hydrochloride Salt of (+)-23 | >30000 | about 0%* |
| Hydrochloride Salt of (+)-24 | >30000 | about 0%* |
| (+)-25 | >30000 | about 0%* |
| (+)-26 | >30000 | about 0%* |
| (+)-27 | >30000 | about 0%* |
| (+)-28a | >30000 | about 0%* |
| (+)-28b | >30000 | about 0%* |

*The compounds exhibited no actual agonist activity within the range of the detection concentrations, and the calculated percent effect values fluctuated disorderly within a narrow range of around 0. Therefore, in this experiment, the $EC_{50}$ was each recorded to be greater than the highest detection concentration (>30000 nM), and the agonistic effect was each recorded at about 0%.

2.4 Conclusion

The compounds of the present disclosure exhibited no or weak agonistic effect on the μ-receptor-mediated β-arrestin signaling pathway.

Comparing the compounds of the present disclosure with the comparative compound 1, the compounds of the present disclosure were significantly more biased toward the Gi signaling pathway, indicating that fewer adverse reactions associated with the β-arrestin signaling pathway would be caused in vivo.

Test 3: Metabolic Stability in Liver Microsomes 3.1 Experimental Purpose: To test the metabolic stability of the compounds of the present disclosure in human liver microsomes 3.2 Experimental Steps:

3.2.1 Compound Formulation a. All samples as well as testosterone, diclofenac and propafenone acting as reference substances were dissolved in DMSO to a storage concentration of 10 mM.

b. Intermediate Solution: 5 μL of the substance to be tested or the reference substance was diluted with 45 μL of DMSO (with 450 μL of 1:1 methanol/water).

c. Working Solution: the intermediate solution was diluted with 450 μL of 100 mM potassium phosphate buffer solution (pH 7.4).

3.2.2 Detection of Metabolic Stability in Liver Microsomes a. Preparation of Materials required for the Experiment Assay Buffer: 100 mM potassium phosphate buffer (pH 7.4)

10 mM MgCl2

NADPH (Reduced Nicotinamide Adenine Dinucleotide Phosphate) Reqeneration System:

β-nicotinamide adenine dinucleotide phosphate, obtained from Sigma, Cat. No. N0505

Isocitric acid, obtained from Sigma, Cat. No. 11252

Isocitrate dehydrogenase, obtained from Sigma, Cat. No. 12002

Stop Solution:

Ice-cold acetonitrile containing 100 ng/mL Tolbutamide and 100 ng/mL Labetalol as an internal standard.

Liver Microsome Solution (final concentration: 0.5 mg protein/mL):

Human liver microsomes, obtained from BD, Cat No. 452117, Lot No. 38291 b. 10 μL of the working solution containing the substance to be tested or the reference substance was added to each of plates (T0, T5, T10, T20, T30, T60, NCF60).

c. The liver microsome solution was dispensed into a 96-well plate in an amount of 680 μL/well, then 80 was added, and then T was added to each of the plates. The above incubation plate was placed at 37° C. and pre-incubated for approximately 10 minutes.

d. 10 μL of 100 mM potassium phosphate buffer was added to each well in the NCF60 plate.

e. After the pre-incubation was finished, the NADPH regeneration system working solution was dispensed into the 96-well plate in an amount of 90 μL/well, and then added to each of the plates in an amount of 10 μL/well to start the reaction.

f. The plates were incubated for an appropriate time (e.g., 5, 10, 20, 30, or 60 minutes).

g. The stop solution (refrigerated at 4° C., containing 100 ng/mL Tolbutamide and 100 ng/mL Labetalol) was added to each sample well in an amount of 300 μL/well.

h. The sample plates were shaken well for about 10 minutes and centrifuged at 4,000 rpm for 20 minutes at 4° C. During the centrifugation, 300 μL of HPLC water was added to each well, and 100 μL of the supernatant was taken for LC-MS/MS analysis.

3.3 Data Analysis $T_{1/2}$ and $Cl_{int(mic)}$ were calculated by the following formula:

$$C_t = C_0 \cdot e^{-k_e \cdot t} \text{ when}$$

$$C_t = \frac{1}{2}C_0,$$

$$T_{1/2} = \frac{\text{Ln}2}{k_e} = \frac{0.693}{k_e}$$

$$CL_{int(mic)} = \frac{0.693}{T_{1/2}} \cdot \frac{1}{\text{Concentration of microsome protein in incubation (mg/ml)}}$$

$$CL_{int(liver)} = CL_{int(mic)} \cdot \frac{\text{microsome protein (mg)}}{\text{liver weight (g)}} \cdot \frac{\text{liver weight (g)}}{\text{body weight (kg)}}$$

Each gram of liver contained 45 mg of microsome protein, and the liver weight was 20 g/kg in a human.

$C_t$ was the concentration at time t, t was the incubation time, $C_0$ was the concentration at time 0, $K_e$ was an elimination rate constant, $Cl_{int(mic)}$ was the intrinsic clearance in liver microsomes, and $Cl_{int(liver)}$ was the intrinsic clearance in liver.

$CL_{int(mic)}$=0.693/half-life/mg of microsome protein per mL(concentration of microsomes during incubation)

$CL_{int(liver)}$=$CL_{int(mic)}$×mg of microsome protein/g of liver weight×a ratio of liver weight to body weight 3.4 Test Results The results of the metabolic stability of the compounds of the present disclosure in human liver microsomes were shown in Table 3.

TABLE 3

| Example Number | $CL_{int(liver)}$ (mL/min/Kg) |
|---|---|
| Comparative Compound 1 | 313.6 |
| Hydrochloride Salt of (+)-1b | 9.3 |

Intrinsic Clearance $CL_{int(liver)}$ in Human Liver

TABLE 3-continued

| Example Number | $CL_{int(liver)}$ (mL/min/Kg) |
|---|---|
| (+)-2 | 49.0 |
| (+)-3 | 39.0 |
| (+)-6 | 86.0 |
| (+)-8 | 10.0 |
| (+)-9 | 8.8 |
| (+)-11 | 72.5 |
| (+)-16 | 29.2 |
| (+)-18 | 84.9 |
| Hydrochloride Salt of (+)-22 | 13.5 |
| Hydrochloride Salt of (+)-23 | 15.6 |
| (+)-28b | 20.0 |

Intrinsic Clearance $CL_{int(liver)}$ in Human Liver 3.5 Conclusion

Compared with the comparative compound, the compounds of the present disclosure exhibited significantly increased metabolic stability in human liver microsomes, indicating that they may have higher stability in human bodies.

Test 4: Study on Inhibition for Cytochrome P450 Isoenzymes 4.1 Experimental Purpose: To test the inhibitory effects of the compounds of the present disclosure on different isoforms of human cytochrome P450 isoenzymes 4.2. Experimental Method 1) The activities of CYP1A2, 2C9, 2C19, 2D6, and 3A4 were measured using a standard substrate method. In each reaction, the enzyme activities were measured in the presence and absence of the substance to be tested, wherein a single sample was measured at a total of eight test concentrations. A 5-in-1 mixed inhibitor was used.

2) An incubation matrix comprising microsomes, a substrate, and an inhibitor or the compound to be tested was pre-incubated at 37° C. for 5 minutes, and then NADPH was added to start the reaction.

| Substrate | Reaction (Enzyme Isoform) | Inhibitor |
|---|---|---|
| Phenacetin | O-deethylation (CYP1A2) | α-naphthoflavone |
| Diclofenac | 1'-hydroxylation (CYP2C9) | sulfaphenazole |
| S-Mephenytoin | 4'-hydroxylation (CYP2C19) | (+)-N-3-benzylnirvanol |
| Dextromethorphan | O-demethylation (CYP2D6) | quinidine |
| Midazolam | 1'-hydroxylation (CYP3A4) | ketoconazole |

3) After the incubation, acetonitrile with an internal standard was added to stop the reaction.

4) Metabolites generated by the substrates were measured by using the LC-MS/MS method, and the peak area ratio of each metabolite to the internal standard was evaluated and the inhibition rate and $IC_{50}$ were calculated.

4.3 Test Results

IC50 values representing the inhibitory effects of the compounds of the present disclosure on different isoforms of human cytochrome P450 isoenzymes were shown in Table 4

TABLE 4

IC$_{50}$ Values Representing Inhibition Effects of Different Isoforms of Cytochrome P450 Isoenzymes

| Example Number | CYP 1A2 IC$_{50}$ (µM) | CYP 2C9 IC$_{50}$ (µM) | CYP 2C19 IC$_{50}$ (µM) | CYP 2D6 IC$_{50}$ (µM) | CYP 3A4 IC$_{50}$ (µM) |
|---|---|---|---|---|---|
| Comparative Compound 1 | >50 | >50 | >50 | 4.6 | 13.6 |
| Hydrochloride Salt of (+)-1b | >50 | >50 | >50 | 35.5 | >50 |
| (+)-2 | >50 | >50 | >50 | 46.4 | >50 |
| (+)-8 | >50 | >50 | >50 | 17.3 | >50 |
| (+)-9 | >50 | >50 | >50 | 23.4 | 21.9 |
| (+)-16 | >50 | >50 | 33.7 | 12.7 | 40.6 |
| (+)-18 | >50 | >50 | >50 | 24.5 | >50 |
| Hydrochloride Salt of (+)-22 | >50 | >50 | >50 | 19.3 | >50 |
| Hydrochloride Salt of (+)-23 | >50 | >50 | >50 | 17.8 | >50 |
| (+)-28b | >50 | >50 | >50 | 5.3 | >50 |

It was meant by ">50 µM" that the inhibitory effect of the compound was less than 50% at 50 µM.

4.4 Conclusion

Compared with the comparative compound, the compounds of the present disclosure exhibited significantly reduced inhibitory effects on human cytochrome P450 isoenzyme isoforms 2D6 and 3A4, indicating that they were less likely to interact with other drugs in human bodies.

Test 5: Testing of Effects on hERG Potassium Channels 5.1 Experimental Purpose: To test the blocking effects of the compounds of the present disclosure on hERG potassium currents.

5.2 Experimental Method:

5.2.1 Cell Preparation a. CHO-hERG cells were cultured in a 175 cm$^2$ culture flask. When the cells were grown to a density of 60 to 80%, the culture solution was removed, and the cells were washed once with 7 mL of PBS (phosphate buffer solution), and then 3 mL of a cell digestion solution (Detachin) was added for digestion of the cells.

b. After completely digested, the cells were neutralized by adding 7 mL of the culture solution and then centrifuged, the supernatant was removed, and then 5 mL of the culture solution was added for resuspension to ensure a cell density of 2 to 5×10$^6$ cells/mL.

5.2.2 Solution Formulation

TABLE 5

Constituents of Intracellular Fluid and Extracellular Fluid

| Reagent | Extracellular Fluid (mM) | Intracellular Fluid (mM) |
|---|---|---|
| CaCl$_2$ | 2 | 5.374 |
| MgCl$_2$ | 1 | 1.75 |
| KCl | 4 | 120 |
| NaCl | 145 | — |
| glucose | 10 | — |
| HEPES | 10 | 10 |
| ethylene glycol bis(2-aminoethylether) tetraacetic acid (EGTA) | — | 5 |
| Na$_2$ATP | — | 4 |
| pH | 7.40 (adjusted by NaOH), with an osmotic pressure of ~305 mOsm (milliosmole) | 7.25 (adjusted by KOH), with an osmotic pressure of ~290 mOsm (milliosmole) |

Note:
"—" denotes no addition.

5.2.3 Electrophysiological Recording Process

The single-cell high-impedance sealing and whole-cell pattern formation processes were both carried out automatically by the Qpatch instrument. After the whole-cell recording pattern was obtained, the cells were clamped at −80 millivolts. A preceding voltage of −50 millivolts was applied for 50 milliseconds prior to application of a depolarizing stimulus of +40 millivolts for 5 seconds, and then the cells were repolarized to −50 millivolts and maintained for 5 seconds and then returned back to −80 millivolts. This voltage stimulation was applied every 15 seconds, and data were recorded for 2 minutes, and thereafter the extracellular fluid was administered and data were recorded for 5 minutes, and then the administration process was started. The compound was administered for 2.5 minutes at each test concentration from the lowest test concentration. After all the concentrations of the compound were administered, 3 µm of Cisapride was administered as a positive comparative compound. At least three cells (n>3) were tested for each concentration.

5.2.4 Compound Formulation a. A 20 mM compound mother solution was diluted with the extracellular fluid, wherein 5 µL of the 20 mM compound mother solution was taken and diluted 500 times to 40 µM by adding 2495 µL of the extracellular fluid thereto, and then 3-fold serial dilutions were performed sequentially in the extracellular fluid containing 0.2% DMSO to obtain a final concentration to be tested.

b. The highest test concentration was 40 µM, and there were six concentrations in total, i.e., 40, 13.33, 4.44, 1.48, 0.49, and 0.16 µM, respectively.

c. The DMSO content in the final test concentration was not more than 0.2%. This concentration of DMSO had no effect on the hERG potassium channel.

5.2.5 Data Analysis

The experimental data were analyzed by XLFit software.

5.2.6 Quality Control

Environment: at a humidity of 20 to 50% and at a temperature of 22 to 25° C.

Reagents: The experimental reagents used were purchased from Sigma, with a purity >98%

The experimental data in the report must meet the following criteria:

Whole Cell Sealing Impedance >100 MΩ

Tail Current Amplitude >400 pA

Pharmacological Parameters:

The inhibitory effect of Cisapride at multiple concentrations on hERG channels was set as a positive control.

5.3 Test Results

IC$_{50}$ values representing the blocking effects of the compounds of the present disclosure on hERG potassium currents were shown in Table 6.

TABLE 6

IC$_{50}$ Representing the blocking effects of hERG Potassium Currents

| Example Number | IC$_{50}$ (µM) |
|---|---|
| Comparative Compound 1 | 5.5 |
| (+)-2 | >40* |
| Hydrochloride Salt of (+)-16 | 22.8 |
| Hydrochloride Salt of (+)-22 | 18.8 |

It was meant by ">40*µM" that the compound had an inhibitory effect represented by an IC$_{50}$ value less than 50% at 40 µM.

5.4 Conclusion

Compared with the comparative compound 1, the compounds of the present disclosure exhibited a weaker inhibitory effect on hERG, indicating less possibility of side effects caused by hERG.

Test 6: Testing of Pharmacokinetics of the Compounds in Rats

6.1 Experimental Purpose
To measure, using a LC/MS/MS method, the medicament concentrations of the compound in plasma and specific tissues at different time points after the compound was administered by a single intravenous injection (IV) to 7-9-week-old male SD rats used as test animals, to study on the pharmacokinetic behavior of the compound of the present disclosure in rats, and to evaluate the pharmacokinetic characteristics thereof.

6.2 Compound Formulation
Compound TRV-130 (comparative compound 1) and the hydrochloride salt of (+)-23 were formulated into clear solutions using physiological saline as a solvent; the compound (+)-5 was formulated into a clear solution using 5% DMSO+25% PEG400+70% physiological saline, acting as a solvent; and the compound (+)-16 was formulated into a clear solution using 10% DMSO+30% PEG400+60% water, acting as a solvent. Each of them was formulated at a concentration of 1 mg/mL and was used for IV (intravenous injection) administration.

6.3 Administration to the Animals
The actual weights of the rats were weighed on the day of administration and volumes to be administered were calculated. The above formulated solutions to be administered were administered by injection into caudal veins of rats.

6.4 Sample Collection and Preparation
About 0.2 mL of whole blood samples were collected by means of jugular vein puncture at the time set in the experimental protocol, and the actual blood collection time was recorded in the experimental records. All the blood samples were added to labeled plastic centrifuge tubes to which K2-EDTA anticoagulant was added in advance. After the blood samples were collected, they were centrifuged at 3,000 g for 10 minutes at 4° C. to prepare the supernatant plasma, and the plasma was stored at −20° C. or a lower temperature for LC-MS/MS analysis.

6.5 Sample Analysis
The concentrations of the compounds in rat plasma were measured by using high-performance liquid chromatography-tandem mass spectrometry (LC-MS/MS). The retention durations of the compounds and internal standard, chromatogram acquisition, and integration of chromatograms were processed using the software Analyst (Applied Biosystems), and data statistics were processed using the software Watson LIMS (Thermo Fisher Scientific) or Analyst (Applied Biosystems). The plasma concentration was processed using a non-compartmental model of WinNonlin™ Version 6.3 (Pharsight, Mountain View, Calif.) which was a pharmacokinetic software, and the pharmacokinetic parameters were calculated using a linear logarithmic trapezoidal method.

6.6 Test Results
The results of pharmacokinetic parameters of the compounds of the present disclosure in rats were shown in Tables 7 and 8:

TABLE 7

First Result of Pharmacokinetic Test in Rats

| | Comparative Compound 1 | (+)-5 | (+)-16 | Hydrochloride Salt of (+)-23 |
|---|---|---|---|---|
| Administered Amount (IV, mg/Kg) | 1.80 | 2.40 | 1.76 | 1.71 |
| Initial Concentration C$_0$ (nM) | 1897 | 1807 | 979 | 1551 |
| Hal-life T$_{1/2}$ (h) | 0.8 | 0.9 | 0.9 | 0.7 |
| Apparent Distribution Volume Vd (L/kg) | 4.3 | 3.60 | 6.3 | 5.0 |
| Apparent Clearance Cl (mL/Kg/minute) | 74.4 | 58.9 | 114 | 113 |
| Area under the Curve AUC$_{0-inf}$ (nM · hour) | 1151 | 1395 | 723 | 763 |

TABLE 8

Second Result of Pharmacokinetic Test in Rats

| | Comparative Compound 1 | (+)-5 | (+)-16 | Hydrochloride Salt of (+)-23 |
|---|---|---|---|---|
| Administered Amount (IV, mg/Kg) | 0.56 | 2.40 | 1.76 | 1.71 |
| Sampling Point (h) | 0.25 | 0.25 | 0.25 | 0.25 |
| Drug Concentration in Plasma Plasma (nM) | 368 | 1041 | 607 | 766 |
| Drug Concentration in Brain Brain (nmol/kg) | 620 | 2218 | 2790 | 1658 |
| Brain/Plasm Ratio B/P ratio | 1.68 | 2.19 | 4.61 | 2.2 |

6.7 Conclusion
Compared with comparative compound 1, the compounds of the present disclosure exhibited considerable pharmacokinetic properties in rats, and the compounds exhibited a significant increase in rat B/P ratio, indicating that the compounds may have a stronger ability to enter the brain.

Test 7: Efficacy of the Compounds in Rat Hot Plate Test

7.1 Experimental Purpose
To evaluate the efficacy of the compounds in the hot plate test for SD rats.

7.2 Compound Formulation
The compound TRV-130 (comparative compound 1), the hydrochloride salt of (+)-16 and the hydrochloride salt of (+)-22 were formulated, using physiological saline as a solvent, into clear solutions at a concentration of 0.1 mg/mL and 0.02 mg/mL for IV (intravenous injection) administration.

Morphine (batch number: 150906-2, supplier: Northeast Pharmaceutical Group Co., Ltd., Shenyang No. 1 Pharmaceutical Factory): formulated into a clear solution at a concentration of 1.2 mg per ml of solution, using physiological saline as a solvent.

7.3 Experimental Method Process 7.3.1 Hot Plate Test a. The animals were transported to the testing laboratory and acclimated in the test environment for more than 15 minutes.

b. The instrument was cleaned with 50% ethanol.

c. The instrument was powered on, and a heating program was set for heating to 52° C.

d. The test animal was placed on the surface of the hot plate, and at the same time the foot pedal was pressed to start the timer to record the time from the beginning to a time point when the animal felt pain.

e. When the animal showed any response to heat (shaking of the paw, paw licking, jumping, contraction of the leg, or the like), the foot pedal was released to stop timing. If the animal did not show a response to thermal stimulation within 20 seconds, the animal was removed from the hot plate to prevent the animal from being scalded.

f. The instrument was cleaned with 50% ethanol, and the next animal was tested after the temperature of the instrument was returned to 52° C.

7.3.2 Baseline Testing and Grouping

The heat pain threshold baseline was tested one day before administration, and the animals were evenly grouped based on the test results.

7.3.3 Administration and Testing

Heat pain thresholds were tested in accordance with time points after the rats were administered.

7.3.4 Data Collection and Analysis

Data were collected using Excel software. The data were analyzed using the software Prism 6.01 (Graph pad software, Inc.).

7.4 Test Results

The efficacy of the compounds of the present disclosure in the rat hot plate test was shown in FIG. 1.

7.5 Conclusion

The compounds of the present disclosure exhibited a better analgesic effect than TRV-130 when the rats were administered in an amount of 0.5 mg/kg; and the compounds of the present disclosure had a longer analgesic effect than TRV-130 at both different doses.

What is claimed is:

1. A compound represented by formula (I), an isomer thereof, or a pharmaceutically acceptable salt thereof,

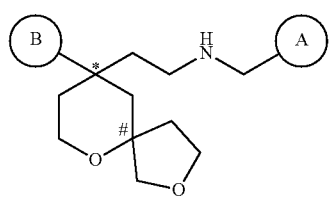

(I)

wherein ring A is selected from the group consisting of a 6-10 membered aryl group and a 5-10 membered heterocyclic group, wherein the 6-10 membered aryl group or 5-10 membered heterocyclic group is optionally substituted with 1, 2, or 3 R;

ring B is selected from the group consisting of phenyl and pyridyl, wherein the phenyl or pyridyl is optionally substituted with 1, 2, or 3 R, wherein each R is independently selected from the group consisting of H, F, Cl, Br, I, OH, $NH_2$, $C_{1-3}$ alkyl and $C_{1-3}$ alkoxy, wherein the $C_{1-3}$ alkyl or $C_{1-3}$ alkoxy is optionally substituted with 1, 2, or 3 R', wherein R' is selected from the group consisting of F, Cl, Br, I, OH, and $NH_2$;

a carbon atom with "*" is a chiral carbon atom, which is in a form of a single (R) or (S) enantiomer or in a form of being enriched with one enantiomer;

a carbon atom with "#" is a chiral carbon atom, which is in a form of a single (R) or (S) enantiomer or in a form of being enriched with one enantiomer; and the 5-10 membered heterocyclic group contains 1, 2, 3, or 4 heteroatoms or heteroatomic groups independently selected from the group consisting of —NH—, —O—, —S—, and N.

2. The compound, isomer thereof, or pharmaceutically acceptable salt thereof according to claim 1, wherein each R is independently selected from the group consisting of H, F, Cl, Br, I, OH, $NH_2$, Me, Et, and

wherein the Me, Et, or

is optionally substitutes with 1, 2, or 3 R'.

3. The compound, isomer thereof, or pharmaceutically acceptable salt thereof according to claim 2, wherein each R is independently selected from the group consisting of H, F, Cl, Br, I, OH, $NH_2$, CN, Me, $CH_2F$, $CHF_2$, CF3, Et, and

4. The compound, isomer thereof, or pharmaceutically acceptable salt thereof according to claim 1, wherein the ring A is selected from the group consisting of phenyl, thienyl, 5,6-dihydro-4H-cyclopenta[c]thienyl, 1,3-dihydrothieno[3,4-c]furanyl, 4,5,6,7-tetrahydrobenzo[c]thiophene, and 1,2,3,4-tetrahydronaphthyl, wherein the phenyl, thienyl, 5,6-dihydro-4H-cyclopenta[c]thienyl, 1,3-dihydrothieno[3,4-c]furanyl, 4,5,6,7-tetrahydrobenzo[c]thiophene, or 1,2,3,4-tetrahydronaphthyl is optionally substituted with 1, 2, or 3 R.

5. The compound, isomer thereof, or pharmaceutically acceptable salt thereof according to claim 1, wherein ring A is selected from the group consisting of

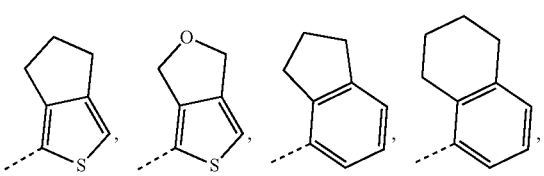

-continued

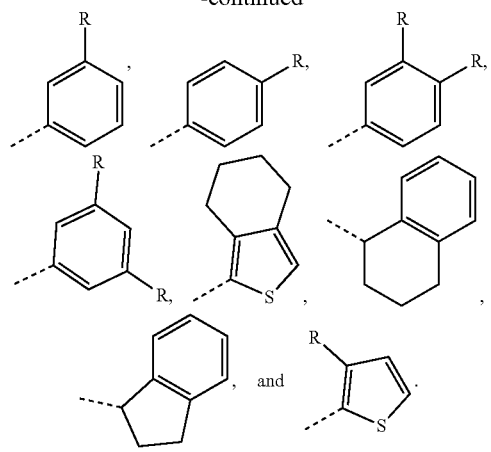

6. The compound, isomer thereof, or pharmaceutically acceptable salt thereof according to claim 5, wherein the ring A is selected from the group consisting of

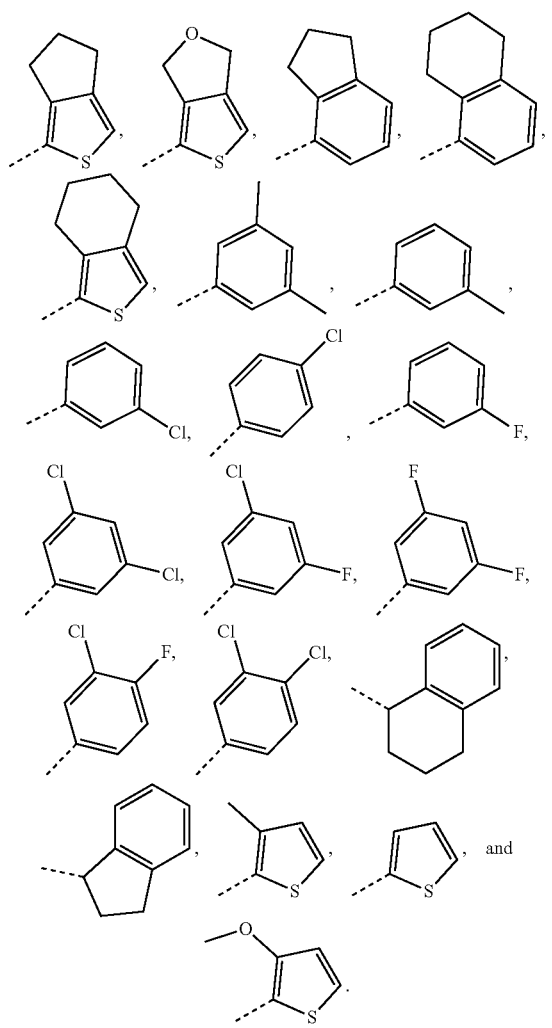

7. The compound, isomer thereof, or pharmaceutically acceptable salt thereof according to claim 1, wherein the ring B is selected from the group consisting of

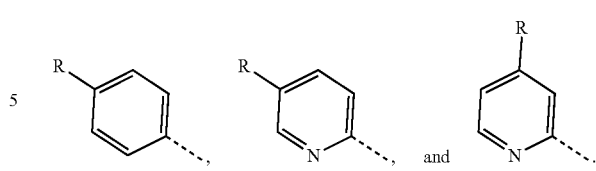

8. The compound, isomer thereof, or pharmaceutically acceptable salt thereof according to claim 7, wherein the firm B is selected from the group consisting of

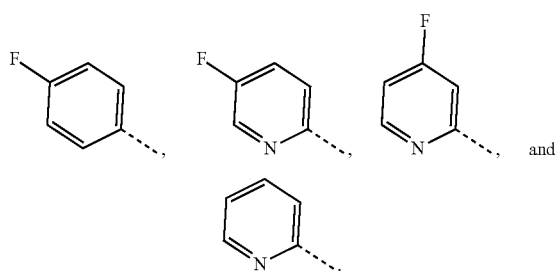

9. The compound, isomer thereof, or pharmaceutically acceptable salt thereof according to claim 1, which is selected from the group consisting of

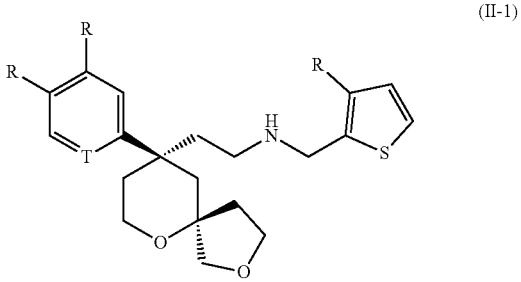

(II-1)

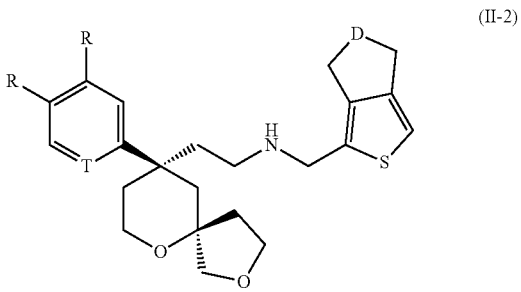

(II-2)

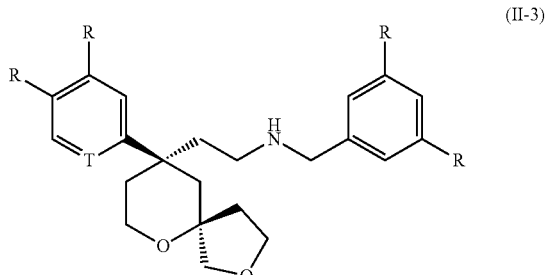

(II-3)

-continued

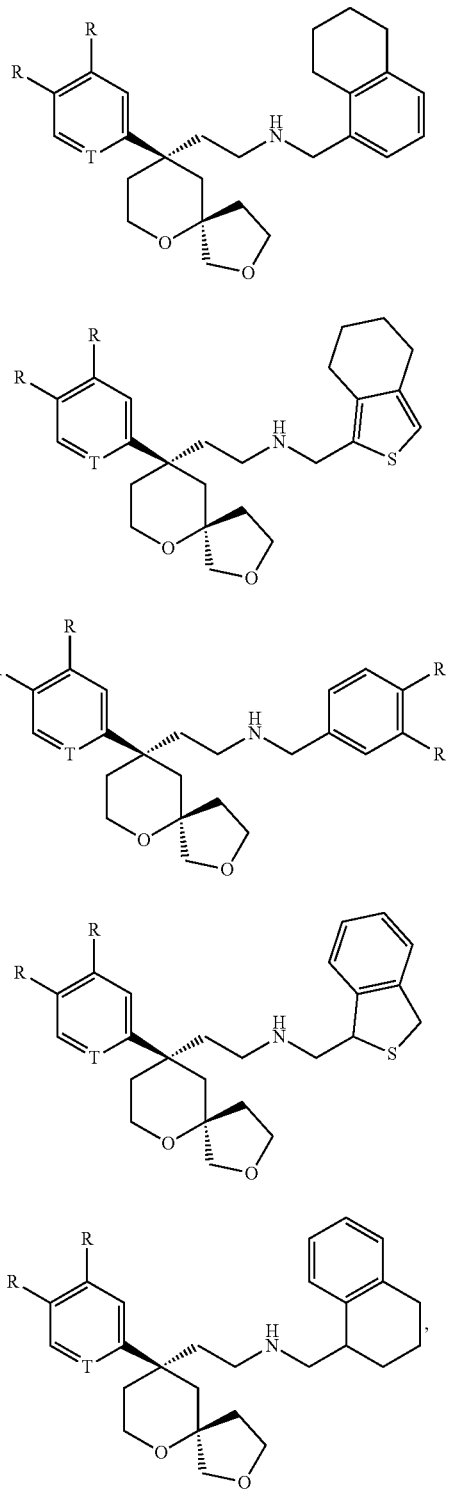

(II-4)

(II-5)

(II-6)

(II-7)

(II-8)

wherein

T is selected from the group consisting of N and CH;

D is selected from the group consisting of O and $CH_2$; and each R is independently selected from the group consisting of H, F, Cl, Br, I, OH, $NH_2$, $C_{1-3}$ alkyl and $C_{1-3}$ alkoxyl, wherein the $C_{1-3}$ alkyl or $C_{1-3}$ alkoxy optionally substituted with 1, 2, or 3 R' is selected from the group consisting of F, Cl, Br, I, OH, and $NH_2$.

10. The compound, isomer thereof, or pharmaceutically acceptable salt thereof according to claim 9, which is selected from the group consisting of

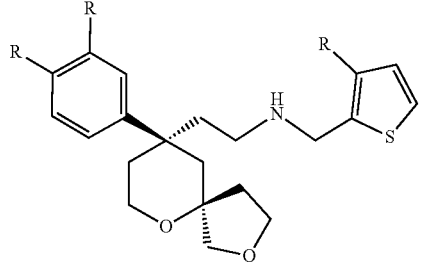

(II-1a)

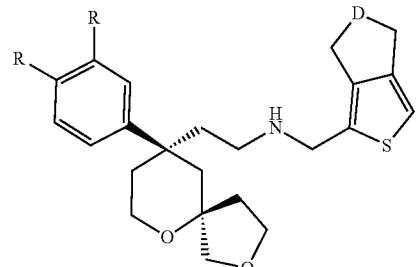

(II-2a)

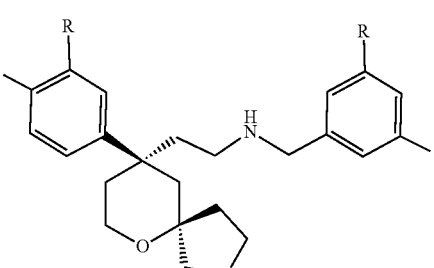

(II-3a)

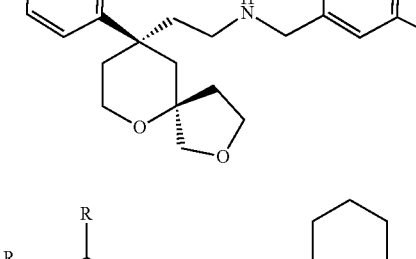

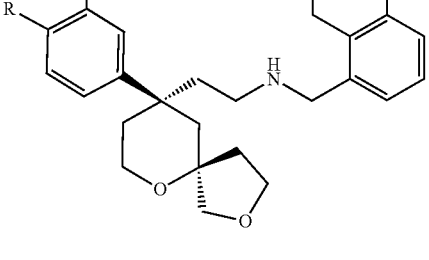

(II-4a)

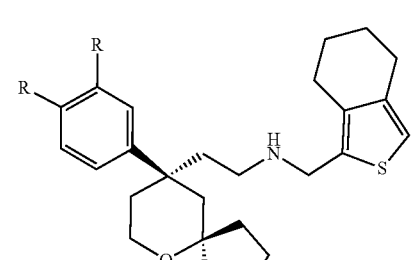

(II-5a)

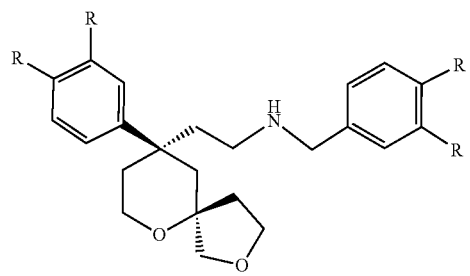
(II-6a)
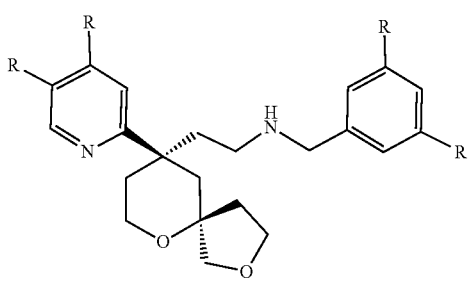
(II-3b)
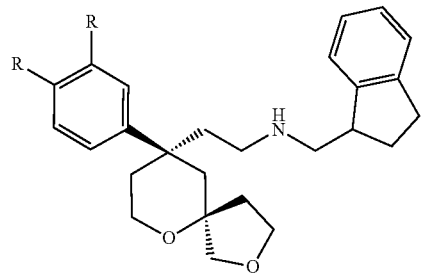
(II-7a)
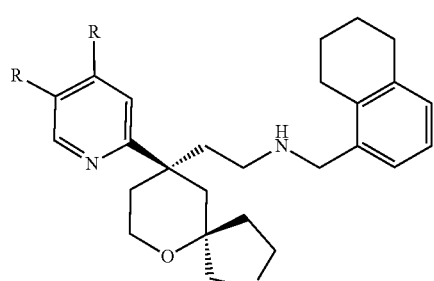
(II-4b)
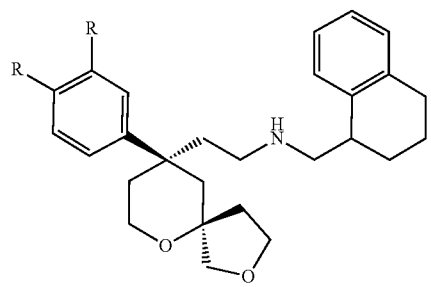
(II-8a)
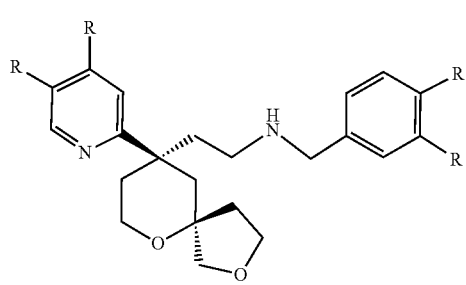
(II-5b)
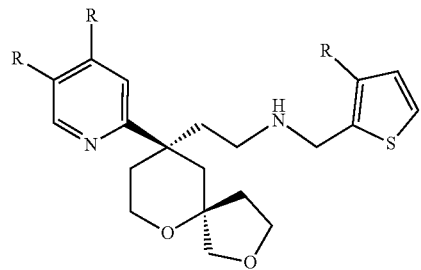
(II-1b)
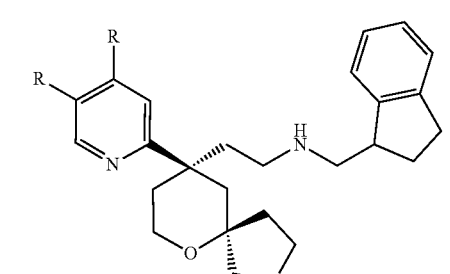
(II-6b)
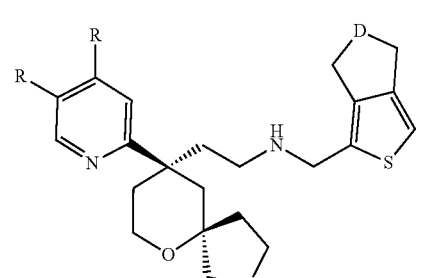
(II-2b)
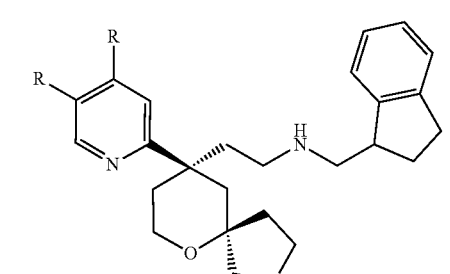
(II-7b)

(II-8b)

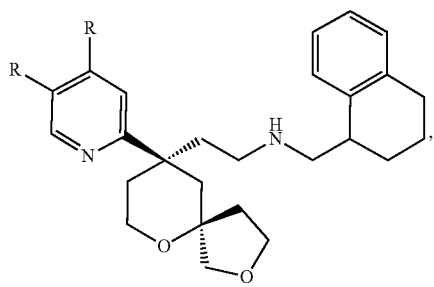

wherein
D is selected from the group consisting of O and CH$_2$; and
each R is independently selected from the group consisting of H, F, Cl, Br, I, OH, NH$_2$, C$_{1-3}$ alkyl and C$_{1-3}$ alkoxyl, wherein the C$_{1-3}$ alkyl or C$_{1-3}$ alkoxy os optionally substituted with 1, 2, or 3 R' is selected from the group consisting of F, Cl, Br, I, OH, and NH$_2$.

11. A compound represented by following formulas, an isomer thereof, or a pharmaceutically acceptable salt thereof, wherein the compound is selected from the group consisting of

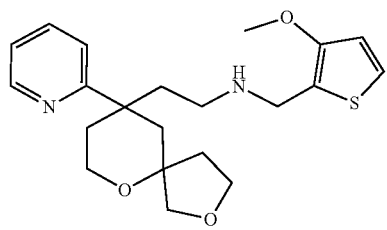

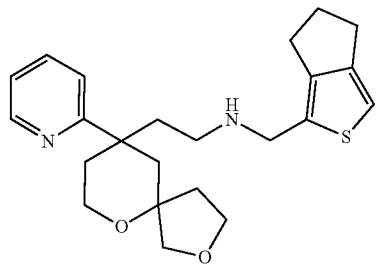

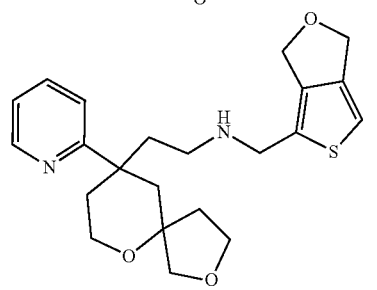

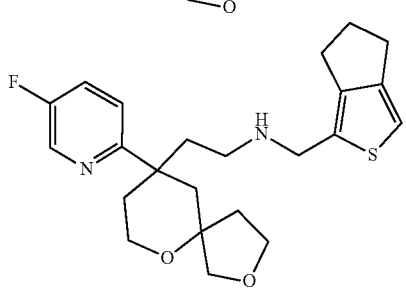

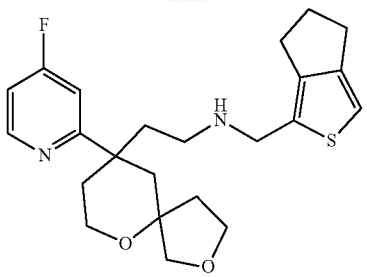

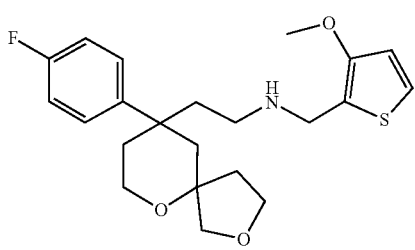

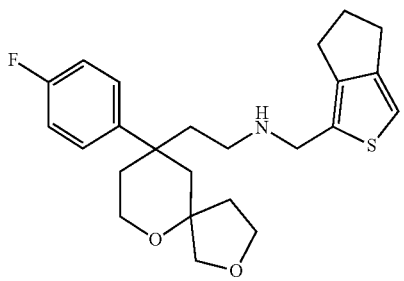

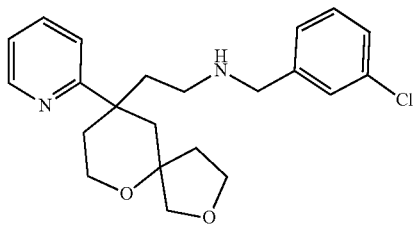

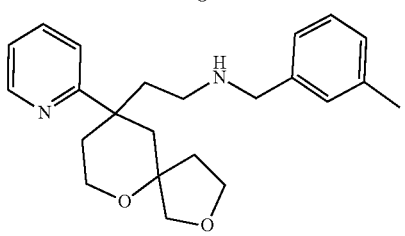

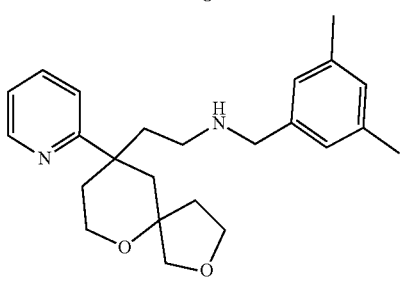

-continued
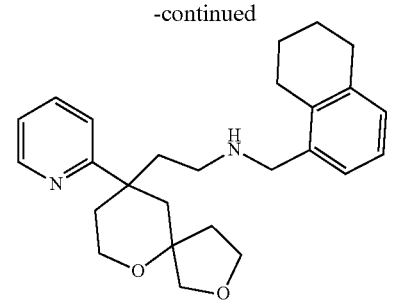
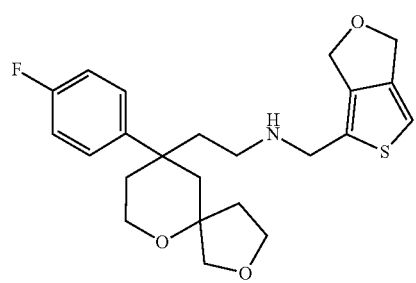
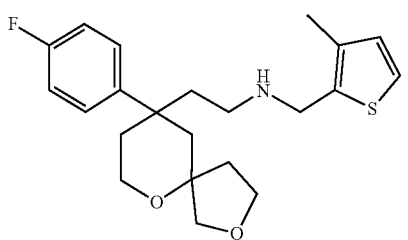
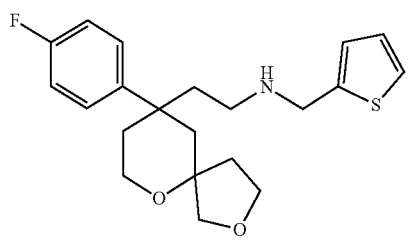
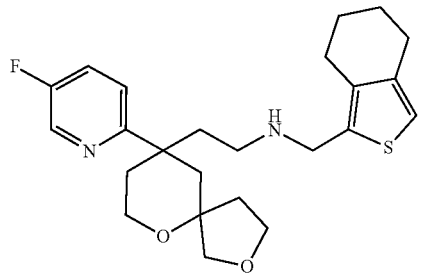
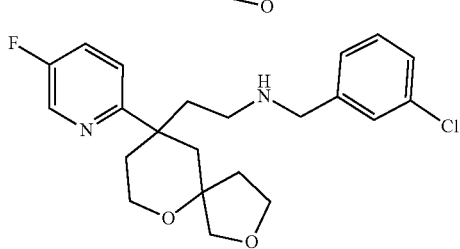
-continued
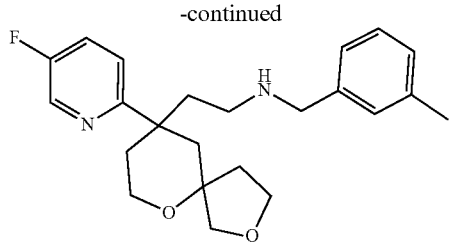
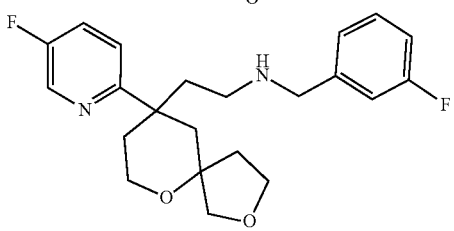
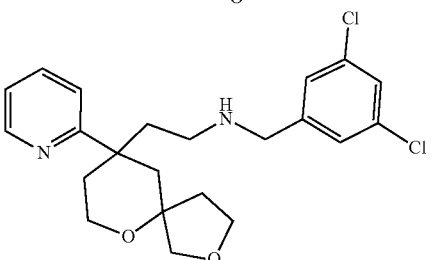
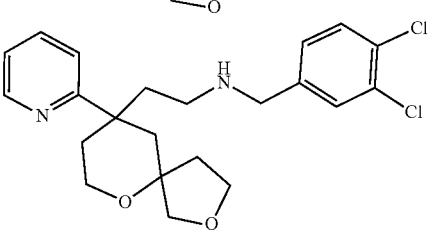
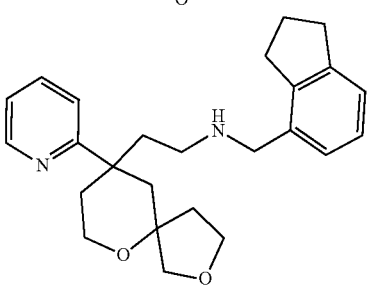
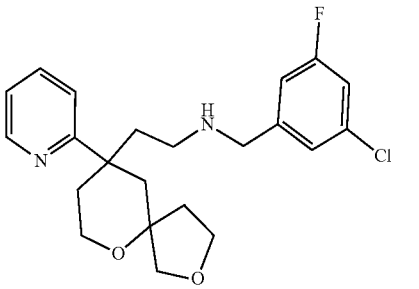
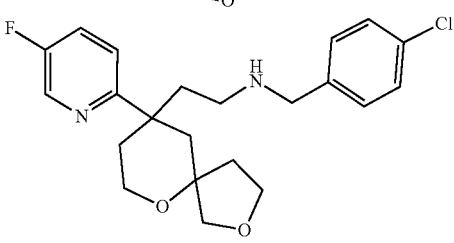

12. The compound, isomer thereof, or pharmaceutically acceptable salt thereof according to claim 11, which is selected from the group consisting of -continued
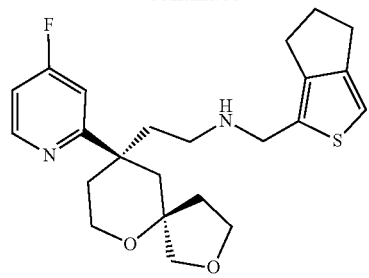
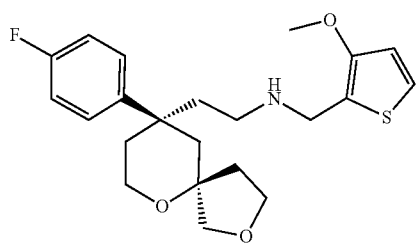
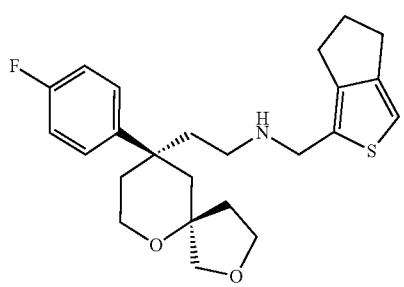
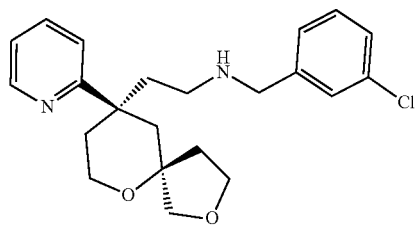
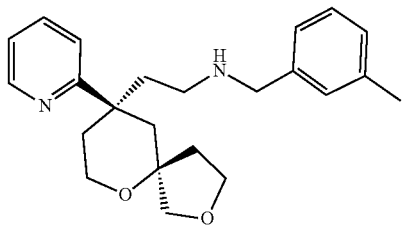
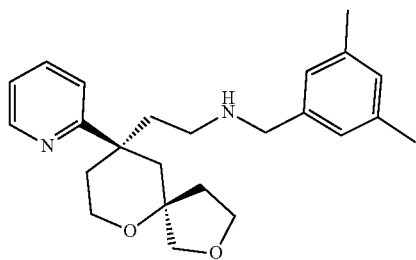
-continued
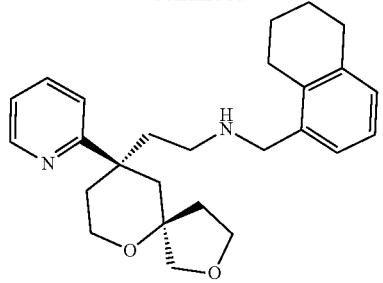
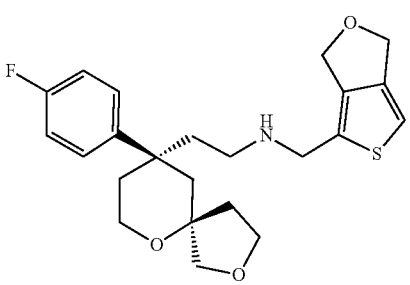
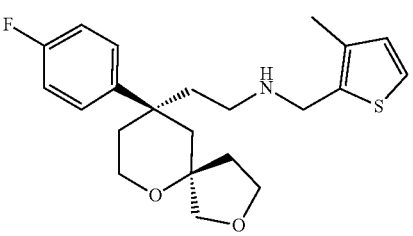
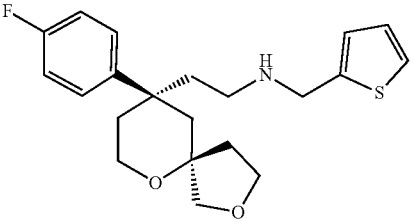
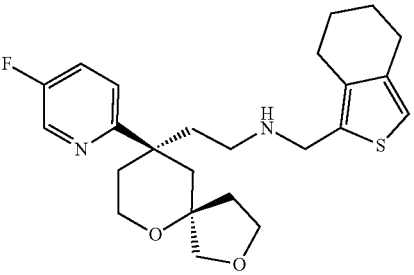
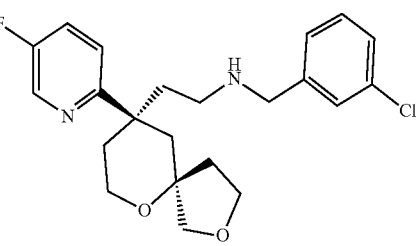

105
-continued

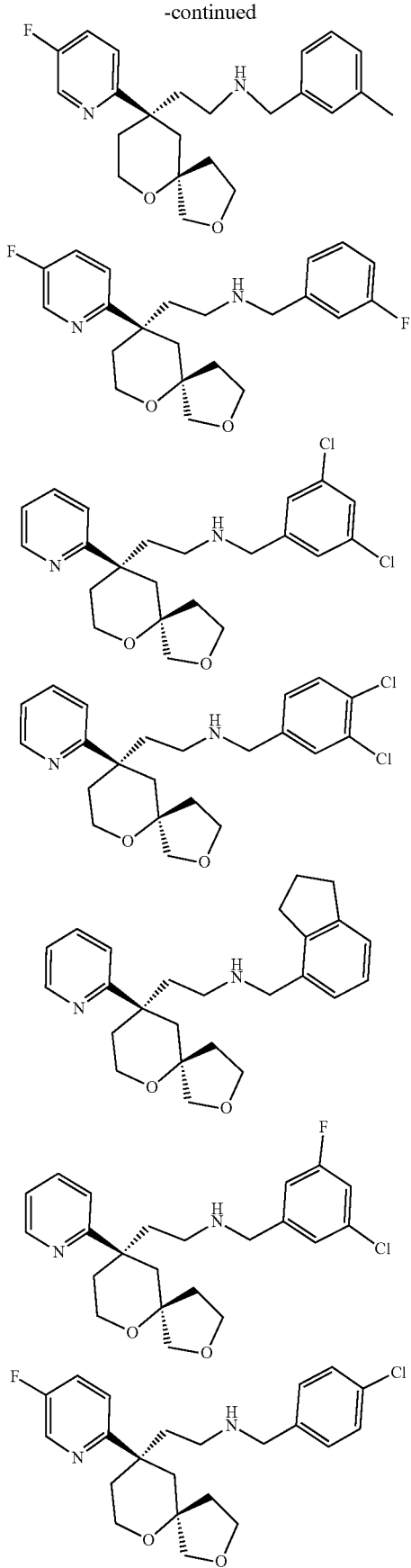

106
-continued

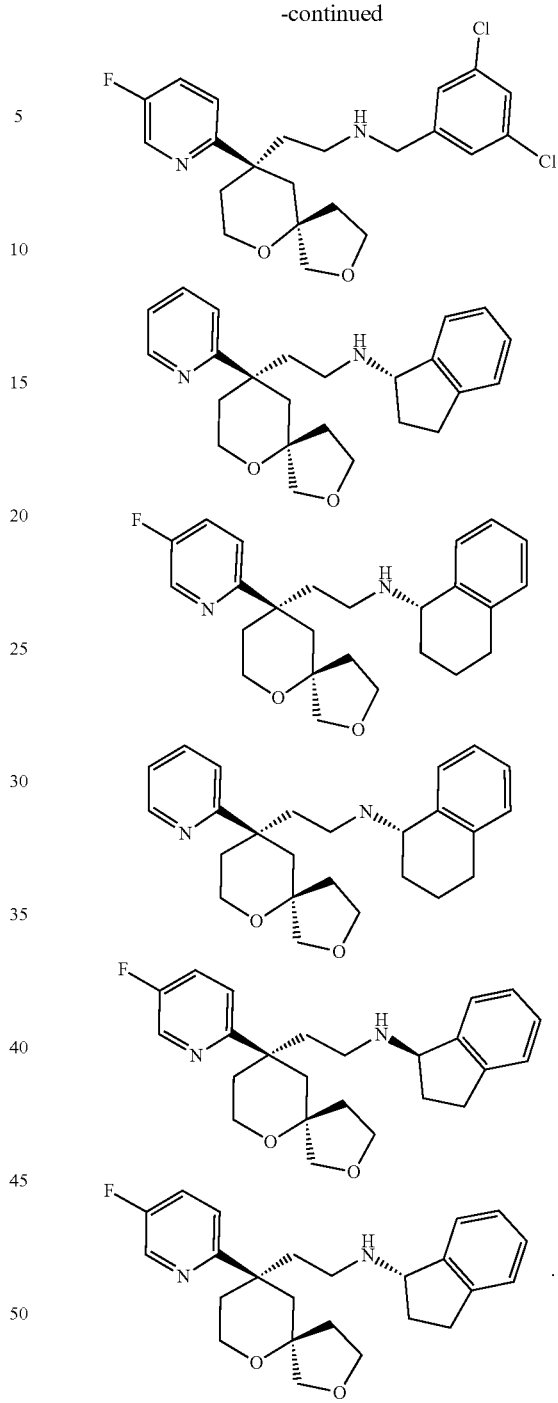

13. A pharmaceutical composition, comprising a therapeutically effective amount of the compound or pharmaceutically acceptable salt thereof according to claim 1 and a pharmaceutically acceptable carrier, with the compound or pharmaceutically acceptable salt thereof acting as an active ingredient.

14. A method for treating a subject having a disease or disorder associated with an agonist for receptor which is an opioid receptor, wherein the disease or disorder includes pain or pain-related disorders, the method comprising administering to the subject a compound of claim 1 or pharmaceutically acceptable salt thereof.

15. The compound, isomer thereof, or pharmaceutically acceptable salt thereof according to claim 9, wherein each R is independently selected from the group consisting of H, F, Cl, Br, I, OH, NH$_2$, Me, Et, and

wherein the Me, Et, or

is optionally substituted with 1, 2, or 3 R'.

16. The compound, isomer thereof, or pharmaceutically acceptable salt thereof according to claim 9, wherein each R is independently selected from the group consisting of H, F, Cl, Br, I, OH, NH$_2$, CN, Me, CH$_2$F, CHF$_2$, CF$_3$, Et, and

17. The compound, isomer thereof, or pharmaceutically acceptable salt thereof according to claim 10, wherein each R is independently selected from the group consisting of H, F, Cl, Br, I, OH, NH$_2$, Me, Et, and

wherein the Me, Et, or

is optionally substituted with 1, 2, or 3 R'.

18. The compound, isomer thereof, or pharmaceutically acceptable salt thereof according to claim 10, wherein each R is independently selected from the group consisting of H, F, Cl, Br, I, OH, NH$_2$, CN, Me, CH$_2$F, CHF$_2$, CF$_3$, Et, and

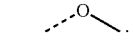

* * * * *

UNITED STATES PATENT AND TRADEMARK OFFICE
CERTIFICATE OF CORRECTION

PATENT NO. : 11,124,523 B2
APPLICATION NO. : 16/755551
DATED : September 21, 2021
INVENTOR(S) : Yang Zhang et al.

It is certified that error appears in the above-identified patent and that said Letters Patent is hereby corrected as shown below:

In the Claims

Column 90, Claim 2, Line 36:
"is optionally substitutes with" should read: --is optionally substituted with--.

Column 93, Claim 9, Line 40:

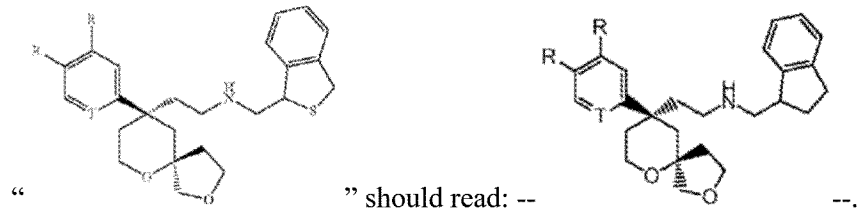

Signed and Sealed this
Thirteenth Day of December, 2022

Katherine Kelly Vidal
*Director of the United States Patent and Trademark Office*